(12) United States Patent
Polodna et al.

(10) Patent No.: US 12,377,203 B2
(45) Date of Patent: *Aug. 5, 2025

(54) FILLER FOR AN APHERESIS SYSTEM

(71) Applicant: Terumo BCT, Inc., Lakewood, CO (US)

(72) Inventors: Taylor Polodna, Golden, CO (US); Brian M. Holmes, Evergreen, CO (US)

(73) Assignee: Terumo BCT, Inc., Lakewood, CO (US)

( * ) Notice: Subject to any disclaimer, the term of this patent is extended or adjusted under 35 U.S.C. 154(b) by 862 days.

This patent is subject to a terminal disclaimer.

(21) Appl. No.: 17/393,116

(22) Filed: Aug. 3, 2021

(65) Prior Publication Data

US 2021/0361849 A1    Nov. 25, 2021

Related U.S. Application Data

(62) Division of application No. 15/958,924, filed on Apr. 20, 2018, now Pat. No. 11,103,629.

(Continued)

(51) Int. Cl.
*A61M 1/36*       (2006.01)
*A61M 1/02*       (2006.01)
(Continued)

(52) U.S. Cl.
CPC .......... *A61M 1/3696* (2014.02); *A61M 1/024* (2013.01); *A61M 1/0272* (2013.01);
(Continued)

(58) Field of Classification Search
CPC .. A61M 1/3696; A61M 1/304; A61M 1/3601; A61M 1/3646; A61M 1/024;
(Continued)

(56) References Cited

U.S. PATENT DOCUMENTS

| | | |
|---|---|---|
| 4,007,871 A | 2/1977 | Jones et al. |
| 4,010,894 A | 3/1977 | Kellogg et al. |

(Continued)

FOREIGN PATENT DOCUMENTS

| | | |
|---|---|---|
| EP | 0134436 A1 | 3/1985 |
| EP | 1749546 A1 | 2/2007 |

(Continued)

OTHER PUBLICATIONS

International Searching Authority, Invitation to Pay Additional Fees and, Where Applicable, Protest Fee, PCT/US2018/028695, Jul. 9, 2018, 18 pages.

(Continued)

*Primary Examiner* — Philip R Wiest
(74) *Attorney, Agent, or Firm* — Harness, Dickey & Pierce, P.L.C.

(57) ABSTRACT

Described are embodiments that include methods and devices for separating components from multi-component fluids. Embodiments may involve use of separation vessels and movement of components into and out of separation vessels through ports. Embodiments may involve the separation of plasma from whole blood. Also described are embodiments that include methods and devices for positioning portions, e.g., loops, of disposables in medical devices. Embodiments may involve use of surfaces for automatically guiding loops to position them into a predetermined position.

5 Claims, 50 Drawing Sheets

Related U.S. Application Data

(60) Provisional application No. 62/539,053, filed on Jul. 31, 2017, provisional application No. 62/488,404, filed on Apr. 21, 2017.

(51) Int. Cl.
*A61M 1/30* (2006.01)
*A61M 1/34* (2006.01)
*A61M 1/38* (2006.01)

(52) U.S. Cl.
CPC .......... *A61M 1/304* (2014.02); *A61M 1/3496* (2013.01); *A61M 1/3601* (2014.02); *A61M 1/36224* (2022.05); *A61M 1/362261* (2022.05); *A61M 1/362262* (2022.05); *A61M 1/362265* (2022.05); *A61M 1/3627* (2013.01); *A61M 1/3646* (2014.02); *A61M 1/3693* (2013.01); *A61M 1/382* (2013.01); *A61M 1/30* (2013.01); *A61M 1/3403* (2014.02); *A61M 1/36222* (2022.05); *A61M 1/3639* (2013.01); *A61M 2202/0415* (2013.01); *A61M 2205/12* (2013.01); *A61M 2205/123* (2013.01); *A61M 2205/331* (2013.01); *A61M 2205/3334* (2013.01); *A61M 2205/3379* (2013.01); *A61M 2205/50* (2013.01)

(58) Field of Classification Search
CPC .............. A61M 1/0272; A61M 1/3496; A61M 1/3627; A61M 1/3693; A61M 1/382; A61M 1/3403; A61M 1/30; A61M 1/3639; A61M 2202/0415; A61M 2205/12; A61M 2205/123; A61M 2205/331; A61M 2205/3334; A61M 2205/3379; A61M 2205/50
See application file for complete search history.

(56) References Cited

U.S. PATENT DOCUMENTS

| | | |
|---|---|---|
| 4,094,461 A | 6/1978 | Kellogg et al. |
| 4,108,353 A | 8/1978 | Brown |
| 4,109,854 A | 8/1978 | Brown |
| 4,109,855 A | 8/1978 | Brown et al. |
| 4,113,173 A | 9/1978 | Lolachi |
| 4,379,452 A | 4/1983 | DeVries |
| 4,387,848 A | 6/1983 | Kellogg et al. |
| 4,419,089 A | 12/1983 | Kolobow et al. |
| 4,425,112 A | 1/1984 | Ito |
| 4,447,221 A | 5/1984 | Mulzet |
| 4,530,691 A | 7/1985 | Brown |
| 4,531,932 A | 7/1985 | Luppi et al. |
| 4,647,279 A | 3/1987 | Mulzet et al. |
| 4,724,317 A | 2/1988 | Brown et al. |
| 5,345,070 A | 9/1994 | Hlavinka et al. |
| 5,520,218 A | 5/1996 | Hlavinka et al. |
| 5,674,173 A | 10/1997 | Hlavinka et al. |
| 5,904,645 A | 5/1999 | Hlavinka |
| 5,913,768 A | 6/1999 | Langley et al. |
| 5,954,971 A | 9/1999 | Pages et al. |
| 11,103,629 B2 * | 8/2021 | Polodna .............. A61M 1/3646 |
| 2004/0058794 A1 * | 3/2004 | Dolecek ................ B04B 5/0428 494/45 |
| 2007/0012623 A1 * | 1/2007 | Robinson ............ A61M 1/3693 210/512.1 |
| 2009/0008306 A1 | 1/2009 | Cicchello et al. |

FOREIGN PATENT DOCUMENTS

| | | |
|---|---|---|
| WO | 88/05691 A1 | 8/1988 |
| WO | 95/17597 A1 | 6/1995 |
| WO | 96/29104 A1 | 9/1996 |
| WO | 03/000026 A2 | 1/2003 |
| WO | 2018/195508 A3 | 10/2018 |

OTHER PUBLICATIONS

International Searching Authority, International Search Report and Written Opinion, PCT/US2018/028695, Nov. 6, 2018, 31 pages.

\* cited by examiner

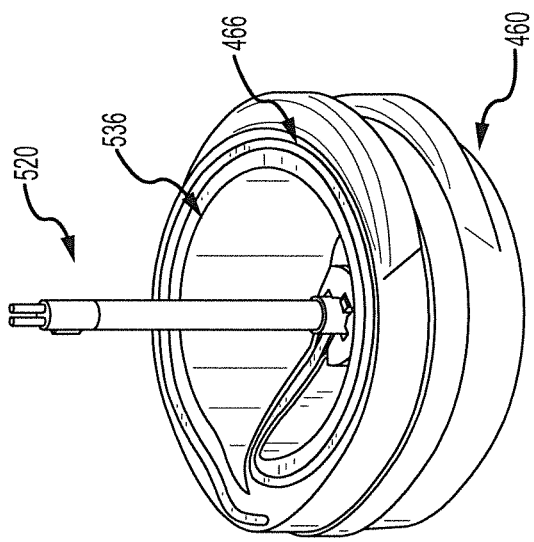
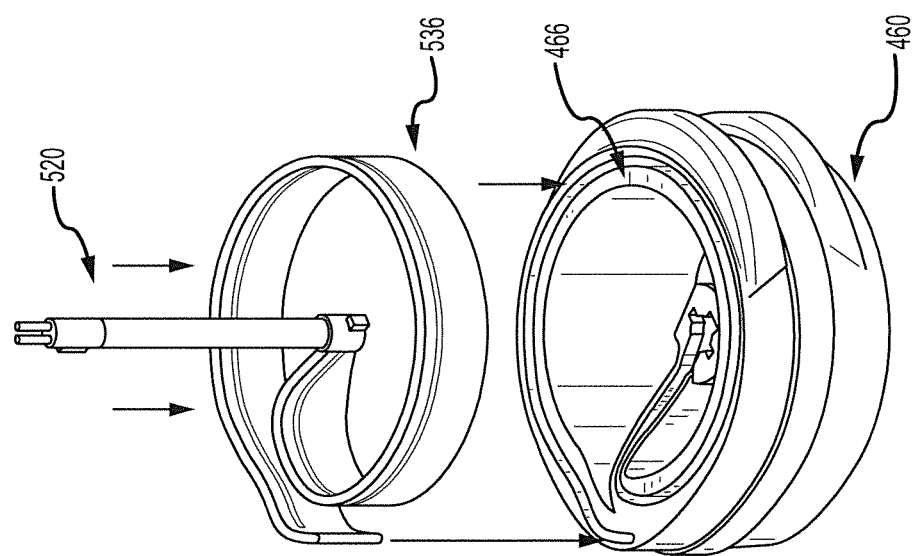

FILLER FOR AN APHERESIS SYSTEM

CROSS REFERENCE TO RELATED APPLICATIONS

The present application is a divisional application of and claims priority to, U.S. patent application Ser. No. 15/958,924, entitled "Filler for an Apheresis System," filed on Apr. 20, 2018 and U.S. patent application Ser. No. 15/958,924 claims the benefit of and priority, under 35 U.S.C. § 119 (e), to U.S. Provisional Application Ser. No. 62/488,404, filed Apr. 21, 2017, entitled "Disposable Loading;" and 62/539,053, filed Jul. 31, 2017, entitled "Component Collection." The entire disclosures of the applications listed above are hereby incorporated by reference, in their entirety as if set forth herein in full, for all that they teach and for all purposes.

FIELD

The present disclosure is generally directed to separating components from multi-component fluids, in particular, toward apheresis methods and systems.

BACKGROUND

There are two common methods for blood donation/collection. The first is whole blood donation from a donor, followed by a centrifugal process that separates blood components from the whole blood based on the density of the blood component. The desired component can be manually, semi-automatically, or automatically moved to a collection container during, or possibly, after the whole blood is under the effect of the forces produced by the centrifuge. The other method may be an apheresis collection that requires a specialized machine.

The apheresis method extracts whole blood from a donor while the donor is connected to the specialized machine. The whole blood can again be centrifuged to collect only the blood component (e.g., plasma) that is desired and can return all other blood components not desired back to the donor during the same donation. The donor is connected to the apheresis machine during the separation and collection of the blood component. Unfortunately, the apheresis process can be lengthy and uncomfortable. Often, the donor must remain connected to the machine for an hour to obtain a blood component donation. Thus, making the donation procedure more efficient is an ongoing desire for apheresis collection sites.

SUMMARY

There is a need for a plasma or other blood component system that can reduce the donation time and increase the comfort of the donor. Embodiments presented herein can increase the efficiency of the donation process by using the separated blood component to push or drive the non-desired blood components back to the donor without stopping and restarting the centrifuge. Thus, the embodiments herein make the donation process more efficient and faster for the donor.

Embodiments may also provide methods and apparatuses for positioning portions, e.g., loops, of disposables in medical devices. Embodiments may involve use of surfaces for automatically guiding loops. In some embodiments, the medical devices may be blood separation machines, such as apheresis machines.

The previously mentioned and other needs are addressed by the various aspects, embodiments, and/or configurations of the present disclosure. Also, while the disclosure is presented in terms of exemplary embodiments, it should be appreciated that individual aspects of the disclosure can be separately claimed.

Embodiments include an assembly for separating a component from a multi-component fluid, the assembly comprising: a filler comprising a channel for holding a separation bladder of a disposable, wherein the channel comprises two opposing walls; and a loop rotational position guide comprising a plurality of bearings, the loop rotational position guide holding a flexible loop of a disposable when the separation bladder is loaded in the channel.

Aspects of the above assembly include wherein the loop rotational position guide comprises a stop plate. Aspects of the above assembly include wherein the flexible loop contacts the stop plate when held in the loop rotational position guide. Aspects of the above assembly include wherein the assembly is part of an apheresis machine. Aspects of the above assembly include wherein the assembly is connected to a rotor that rotates the loop rotational position guide around an axis of rotation. Aspects of the above assembly include wherein the plurality of bearings comprises a plurality of pairs of roller bearings.

Embodiments include a centrifuge assembly, comprising: a centrifuge housing having an outer surface and an internal cavity, wherein the centrifuge housing rotates about a rotation axis of the centrifuge assembly; a fluid separating body disposed at least partially within the internal cavity of the centrifuge housing and configured to rotate relative to the centrifuge housing about the rotation axis; and a fluid line loop arm attached to a portion of the centrifuge housing and running along a length of the outer surface of the centrifuge housing, the fluid line loop arm including a bearing set disposed at a point along the length of the outer surface, wherein the bearing set is configured to contact a tubing portion of an interconnected fluid line loop and maintain the fluid line loop in an engaged position relative to the centrifuge housing while allowing the fluid line loop to rotate in the engaged position.

Aspects of the above centrifuge assembly include wherein the bearing set comprises a pair of roller bearings. Aspects of the above centrifuge assembly include wherein the bearing set comprises a plurality of pairs of roller bearings. Aspects of the above centrifuge assembly include wherein the centrifuge assembly is part of an apheresis machine. Aspects of the above centrifuge assembly include wherein the fluid line loop is affixed to a static nonrotating portion of the apheresis machine at a first end of the fluid line loop via a first positively-located connector, and wherein the fluid line loop is interconnected to the fluid separating body within the internal cavity at a second end of the fluid line loop via a second positively-located connector. Aspects of the above centrifuge assembly include wherein the second end of the fluid line loop rotates with the fluid separating body. Aspects of the above centrifuge assembly include wherein the fluid line loop is physically and fluidly attached to a disposable fluid separation bladder at the second positively-located connector. Aspects of the above centrifuge assembly include wherein the fluid line loop comprises a plurality of lumens, and wherein the fluid separation bladder comprises a first flexible sheet attached to a second flexible sheet forming a fluid pathway, wherein a first portion of the fluid pathway is narrow compared to a second portion of the fluid pathway.

Embodiments include a method for automatically loading a fluid line loop into a centrifuge assembly, the method comprising: attaching the fluid line loop at a first end to a fluid separating body of the centrifuge assembly; and rotating the fluid separating body in a first rotational direction relative to a housing of the centrifuge assembly, wherein rotating the fluid separating body causes the fluid line loop to rotate relative to the housing and guide into a channel of a loop arm attached to a portion of the housing, wherein the channel includes bearings disposed in a bearing set attached to the loop arm, wherein the bearings hold the fluid line loop in a position relative to the housing as the centrifuge assembly rotates.

Aspects of the above method include wherein the bearings contact a portion of the fluid line loop as the fluid line loop rotates inside the channel in the position relative to the housing. Aspects of the above method include wherein centrifuge housing rotates in the first rotational direction at a first angular velocity about a rotation axis and the fluid separating body is caused to rotate at a different second angular velocity about the rotation axis via a twisting force provided by the fluid line loop. Aspects of the above method include wherein the second angular velocity is substantially two times the first angular velocity. Aspects of the above method include wherein the fluid line loop is physically and fluidly attached to a disposable fluid separation bladder disposed at least partially within the fluid separating body. Aspects of the above method further comprising: attaching a second end of the fluid line loop to a rotationally fixed point of an apheresis machine; and rotating, via a rotor and motor assembly of the apheresis machine, the centrifuge assembly about the rotation axis relative to the rotationally fixed point of the apheresis machine.

Embodiments include a method for collecting a blood component through apheresis, the method comprising: drawing whole blood into a centrifuge from a donor; spinning the centrifuge to cause centrifugal force to act on the whole blood to separate the whole blood into a least a first blood component and red blood cells; separating a first blood component from the whole blood; extracting the first blood component into a container; detecting when a second blood component is being extracted; and after the second blood component is detected and while the centrifuge continues to spin, forcing the separated first blood component back towards the centrifuge to move at least the red bloods cells from the centrifuge and back into the donor.

Aspects of the above method include wherein the first blood component is one or more of plasma, platelets, red blood cells and/or high hematocrit blood. Aspects of the above method include wherein the second blood component is one or more of plasma, platelets, red blood cells and/or high hematocrit blood. Aspects of the above method include wherein the first blood component is two or more of plasma, platelets, red blood cells and/or high hematocrit blood. Aspects of the above method include wherein the centrifuge spins at a first speed when separating the first blood component from the whole blood. Aspects of the above method include wherein the centrifuge continues to spin at the first speed when forcing the separated first blood component back towards the centrifuge. Aspects of the above method include wherein the centrifuge spins at a second speed when drawing whole blood into the centrifuge from the donor. Aspects of the above method include wherein the second speed is slower than the first speed. Aspects of the above method include wherein the first blood component is separated from the whole blood in a blood component collection set that is inserted into the centrifuge. Aspects of the above method include wherein the centrifuge includes a filler that spins a blood component collection bladder associated with the blood component collection set. Aspects of the above method include wherein the blood component collection bladder is inserted into a collection insert channel formed in the filler to hold the blood component collection bladder.

Embodiments include an apheresis system comprising: a needle inserted into a blood vessel of a donor to draw whole blood from the donor; a first tube having a lumen, fluidly associated with the needle, that moves the whole blood through the lumen; a draw pump engaged with the first tube that draws the whole blood into a centrifuge from the donor; the centrifuge that spins to cause centrifugal force to act on the whole blood to separate the whole blood into a least a first blood component and red blood cells; a blood component collection bladder, inserted into the centrifuge and fluidly associated with the first tube, that separates the first blood component from the whole blood; a second tube, fluidly associated the blood collection bladder, that moves the first blood component from the blood component collection bladder; a collection bottle, fluidly associated with the second tube, that extracts the first blood component from the apheresis system; a sensor positioned in physical proximity to the second tube to detect when a second blood component is being extracted from the whole blood; and after the second blood component is detected by the sensor and while the centrifuge continues to spin, a return pump, engaged with the second tube, that forces the separated first blood component back towards the blood component collection bladder through the second tube to move at least the red bloods cells from the blood component collection bladder and back into the donor.

Aspects of the above apheresis system include wherein the first blood component is plasma and the second blood component is platelets, red blood cells, and/or high hematocrit blood. Aspects of the above apheresis system further comprises an anticoagulant pump to draw anticoagulant from an anticoagulant bag and mix the anticoagulant with whole blood at a manifold or junction fluidly associated with the first tube. Aspects of the above apheresis system include wherein the centrifuge includes a filler that spins the blood component collection bladder. Aspects of the above apheresis system include wherein the blood component collection bladder is inserted into a collection insert channel formed in the filler to hold the blood component collection bladder.

Embodiments include a blood component collection set associated with an apheresis system comprising: a needle inserted into a blood vessel of a donor to draw whole blood from the donor; a first tube having a lumen, fluidly associated with the needle, that moves the whole blood through the lumen, wherein a draw pump engaged with the first tube draws the whole blood from a donor; a blood component collection bladder, inserted into a centrifuge and fluidly associated with the first tube, that separates the first blood component from the whole blood; a second tube, fluidly associated with the blood collection bladder, that moves the first blood component from the blood component collection bladder; and a collection bottle fluidly associated with the second tube that extracts the first blood component from the apheresis system, wherein a sensor is positioned in physical proximity to the second tube to detect when a second blood component is being extracted from the whole blood; and wherein, after the second blood component is detected by the sensor and while the centrifuge continues to spin, a return pump engaged with the second tube forces the separated first blood component back towards the blood component collection bladder through the second tube to move at least the red bloods cells from the blood component collection bladder and back into the donor.

Aspects of the above blood component collection set include wherein the first blood component is plasma and the second blood component is platelets. Aspects of the above blood component collection set include wherein the draw pump is disengaged when the return pump forces the separated first blood component back towards the blood component collection bladder through the second tube to move at least the red bloods cells from the blood component collection bladder and back into the donor. Aspects of the above blood component collection set include wherein the blood component collection bladder is inserted and held in a filler, in the centrifuge, that spins the blood component collection bladder. Aspects of the above blood component collection set include wherein the blood component collection bladder is inserted into a collection insert channel formed in the filler to hold the blood component collection bladder.

Embodiments include a filler for holding a separation bladder in which a component is separated from a composite fluid, the filler comprising: a channel for holding a separation bladder during separation of the component from the composite fluid, the channel comprising: a first wall; and a second wall opposite the first wall; and wherein a first end of the channel is adjacent a central portion of the filler and the channel spirals toward an outside perimeter of the filler.

Aspects of the above filler include wherein a top portion of the channel is narrower than a middle portion of the channel. Aspects of the above filler include wherein at least a portion of the second wall has a concave surface. Aspects of the above filler include wherein the second end of the channel is located so that it experiences a higher gravitational force during separation than the first end. Aspects of the above filler include wherein the top portion of the channel provides reinforcement to the separation bladder during separation.

Embodiments include a fluid separation filler, comprising: a body having a rotation axis substantially disposed at a mass center of the body; and a fluid collection insert channel disposed in the body and following a substantially spiral path running from a first point adjacent to the rotation axis spirally outward to a second point disposed adjacent to a periphery of the body, wherein the fluid collection insert channel jogs outwardly toward the periphery of the body near an end of the substantially spiral path defining a third point of the fluid collection insert channel disposed furthest from the rotation axis.

Aspects of the above fluid separation filler further comprise: a fluid collection chamber disposed within the body and following a portion of the substantially spiral path, wherein the fluid collection insert channel connects to the fluid collection chamber defining access area between an interior of the fluid collection chamber and an exterior of the body. Aspects of the above fluid separation filler include wherein the fluid collection chamber is configured to receive a disposable fluid collection bladder. Aspects of the above fluid separation filler include wherein a dimension from the rotation axis to the third point of the substantially spiral path is greater than a dimension from the rotation axis to the second point of the substantially spiral path. Aspects of the above fluid separation filler include wherein a width of the fluid collection chamber at a point along the substantially spiral path is greater than a width of the fluid collection insert channel at the point along the substantially spiral path. Aspects of the above fluid separation filler include wherein the fluid collection chamber further comprises a first wall following an innermost portion of the substantially spiral path and a second wall substantially parallel to the first wall and following an outer most portion of the substantially spiral path. Aspects of the above fluid separation filler include wherein the fluid collection chamber further comprises one or more tapered walls disposed between the first wall and the second wall, and wherein the one or more tapered walls are configured to guide the disposable fluid collection bladder into a seated position within the fluid collection chamber. Aspects of the above fluid separation filler include wherein a fluid inlet for the disposable fluid collection bladder when installed in the fluid collection chamber is disposed adjacent to the rotation axis and a first fluid path in the disposable fluid collection bladder follows the substantially spiral path outwardly toward an end of the disposable fluid collection bladder disposed adjacent to the third point of the fluid collection insert channel disposed furthest from the rotation axis, and fluidly interconnects with a second fluid path separated from the first fluid path in the disposable fluid collection bladder running in a direction from the third point following the substantially spiral path inwardly toward a fluid outlet for the disposable fluid collection bladder disposed adjacent to the rotation axis. Aspects of the above fluid separation filler include wherein the fluid inlet and the fluid outlet are part of a connector attached to the disposable fluid collection bladder, and wherein the body of the fluid separation filler includes a connection point that engages with the connector. Aspects of the above fluid separation filler include wherein the connector includes at least one key feature, wherein the connection point includes at least one mating key feature, and wherein the key features positively locate the connector relative to the connection point.

Embodiments include a centrifuge assembly, comprising: a centrifuge housing having an internal cavity, wherein the centrifuge housing rotates about a rotation axis of the centrifuge assembly; and a fluid separating body disposed at least partially within the internal cavity of the centrifuge housing and configured to rotate relative to the centrifuge housing about the rotation axis, wherein the fluid separating body includes a fluid collection insert channel disposed in the fluid separating body following a substantially spiral path running from a first point adjacent to the rotation axis spirally outward to a second point disposed adjacent to a periphery of the fluid separating body, wherein the fluid collection insert channel jogs outwardly toward the periphery of the body near an end of the substantially spiral path defining a third point of the fluid collection insert channel disposed furthest from the rotation axis.

Aspects of the above centrifuge assembly include wherein the fluid separating body further comprises a fluid collection chamber disposed within the body and following a portion of the substantially spiral path, wherein the fluid collection insert channel connects to the fluid collection chamber defining an access area between an interior of the fluid collection chamber and an exterior of the fluid separating body. Aspects of the above centrifuge assembly further comprise a disposable fluid collection bladder disposed within the fluid collection chamber following the substantially spiral path, wherein the disposable fluid collection bladder includes a fluid inlet disposed adjacent to the rotation axis and a first fluid path in the disposable fluid collection bladder follows the substantially spiral path outwardly toward an end of the disposable fluid collection bladder disposed adjacent to the third point of the fluid collection insert channel disposed furthest from the rotation axis, and fluidly interconnects with a second fluid path separated from the first fluid path in the disposable fluid collection bladder running in a direction from the third point following the substantially spiral path inwardly toward a fluid outlet for the disposable fluid collection bladder disposed adjacent to the rotation axis. Aspects of the above centrifuge assembly include wherein the centrifuge assembly is part of an apheresis machine. Aspects of the above centrifuge assembly include wherein the centrifuge housing is split into an upper housing and a lower housing, wherein the upper housing includes the internal cavity, wherein the upper housing is rotatable between an open state and a closed state about a pivot axis that is offset and substantially perpendicular to the rotation axis, and wherein the fluid collection insert channel of the fluid separating body is accessible in the open state and inaccessible in the closed state.

Embodiments include a blood component collection loop comprising: a flexible loop; a system static loop connector disposed at a first end of the flexible loop, wherein the system static loop connector is connected to the fixed loop connection of a centrifuge to fix the first end of the flexible loop to rotate in unison with the centrifuge; a filler loop connector disposed at a second end, opposite the first end, of the flexible loop, wherein the filler loop connector is connected to a loop connection area of a filler, and wherein torsional forces based on twist in the flexible loop are imparted to the filler through the filler loop connector; and wherein flexible loop is rotationally moved to be captured by a loop rotational position guide positioned on the centrifuge.

Aspects of the above blood component collection loop include wherein the blood component collection loop is part of a blood component collection set, and wherein the blood component collection set is associated with an apheresis system. Aspects of the above blood component collection loop include wherein the loop rotational position guide is attached to a rotor that rotates the loop rotational position guide and the flexible loop around an axis of rotation. Aspects of the above blood component collection loop include wherein the blood component collection loop is at least partially positioned by a loop position stop plate. Aspects of the above blood component collection loop include wherein the flexible loop is curved around the centrifuge. Aspects of the above blood component collection loop include wherein at the flexible loops is also held in position by a loop containment bracket. Aspects of the above blood component collection loop include wherein at least a portion of the loop rotational position guide comprises a loop twist support bearing. Aspects of the above blood component collection loop include wherein the loop twist support bearing comprises a pair of roller bearings. Aspects of the above blood component collection loop include wherein the loop twist support bearing allows the flexible loop to twist. Aspects of the above blood component collection loop include wherein the twist causes the filler to rotate at a greater angular velocity than the centrifuge. Aspects of the above blood component collection loop include wherein the flexible loop can contain two or more lumens to move whole blood and/or blood components within the flexible loop.

Embodiments include an assembly for loading a flexible loop, the assembly comprising: a loop rotation position guide comprising a channel for holding a flexible loop of a blood component collection set; a loop twist support bearing, disposed in the channel and on a portion of the loop rotation position guide, to support the flexible loop; and a loop capture arm, wherein the loop capture arm is positioned adjacent the channel and connected to the loop rotation position guide, to guide the flexible loop into the channel and in contact with the loop twist support bearing.

Aspects of the above assembly include wherein the assembly is part of an apheresis machine, and wherein the loop rotation position guide is attached to centrifuge that rotates the loop rotation position guide and the flexible loop around an axis of rotation. Aspects of the above assembly include wherein the loop rotation position guide further includes a loop position stop plate to further position the flexible loop. Aspects of the above assembly further comprise a loop containment bracket, positioned in a plane with the loop rotation position guide and disposed on the centrifuge, to further capture the flexible loop.

Embodiments include a method for automatically loading a flexible loop into an assembly, the method comprising: connecting a system static loop connector, disposed at a first end of the flexible loop, to a fixed loop connection of a centrifuge to fix the first end of the flexible loop to rotate in unison with the centrifuge; connecting a filler loop connector, disposed at a second end, opposite the first end, of the flexible loop, to a loop connection area of a filler, and wherein torsional forces based on twist in the flexible loop are imparted to the filler through the filler loop connector; and rotationally moving the flexible loop into a loop rotational position guide positioned on the centrifuge.

Aspects of the above method include wherein the flexible loop engages a loop twist support bearing, disposed in a channel formed by the loop rotation position guide, wherein the loop twist support bearing supports the flexible loop. Aspects of the above method include wherein a loop capture arm contacts the flexible loop when rotating to guide the flexible loop into the channel and in contact with the loop twist support bearing. Aspects of the above method include wherein the loop rotation position guide further includes a loop position stop plate to prevent over-rotation of the flexible loop past the channel. Aspects of the above method include wherein a loop containment bracket, positioned in a plane with the loop rotation position guide and disposed on the centrifuge, further captures and holds the flexible loop.

Embodiments include a soft cassette comprising: a first cassette port; a second cassette port; a direct flow lumen fluidly connected to the first cassette port and the second cassette port; a drip chamber inter-disposed in the direct flow lumen such that the fluid passing through the direct flow lumen passes through the drip chamber; and a fluid flow bypass path both fluidly connected to the direct flow lumen adjacent the first cassette port and between the first cassette port and the drip chamber and fluidly connected to the direct flow lumen adjacent the second cassette port and between the second cassette port and the drip chamber, such that fluid flowing through the fluid flow bypass path bypasses the drip chamber.

Aspects of the above soft cassette include wherein the fluid flow bypass path is comprised of a first bypass branch fluidly connected to the direct flow lumen adjacent the first cassette port and a second bypass branch fluidly connected to the direct flow lumen adjacent the second cassette port. Aspects of the above soft cassette include wherein the fluid flow bypass path further comprises a fluid pressure annulus disposed between and fluidly connected to the first bypass branch and the second bypass branch. Aspects of the above soft cassette include wherein the direct flow lumen comprises a first compliant region, disposed between a first connection with the first bypass branch and the drip chamber, that allows a first fluid control valve to occlude the direct flow lumen. Aspects of the above soft cassette include wherein the direct flow lumen comprises a second compliant region, disposed between a second connection with the second bypass branch and the drip chamber, that allows a second fluid control valve to occlude the direct flow lumen. Aspects of the above soft cassette include wherein the direct flow lumen comprises a third compliant region, disposed in the first bypass branch, that allows a draw fluid control valve to occlude the first bypass branch. Aspects of the above soft cassette include wherein the first cassette port is fluidly connected to a cassette inlet tubing that moves fluid from a donor into the soft cassette or fluid from the soft cassette to the donor, and wherein the second cassette port is fluidly connected to a loop inlet tubing that moves fluid from a soft cassette into the centrifuge or fluid from the centrifuge to the soft cassette. Aspects of the above soft cassette include wherein, when drawing fluid from the donor, the fluid passes through the fluid flow bypass path. Aspects of the above soft cassette include wherein, when sending fluid to the donor, the fluid passes through the direct flow lumen. Aspects of the above soft cassette include wherein, when drawing fluid from the donor in a subsequent draw, a portion of the fluid previously sent to the donor through the direct flow lumen is maintained in the drip chamber when the fluid passes through the fluid flow bypass path. Aspects of the above soft cassette include wherein the soft cassette is part of a blood component collection set. Aspects of the above soft cassette include wherein the blood component collection set is part of an apheresis system.

Embodiments include a blood component collection set, the blood component collection set comprising: a centrifuge to separate blood components from whole blood; a cassette inlet tubing fluidly connected to a donor; a loop inlet tubing fluidly connected to the centrifuge; a soft cassette comprising: a first cassette port fluidly connected to the cassette inlet tubing; a second cassette port fluidly connected to the loop inlet tubing; a direct flow lumen fluidly connected to the first cassette port and the second cassette port; a drip chamber inter-disposed in the direct flow lumen such that the fluid passing through the direct flow lumen passes through the drip chamber; and a fluid flow bypass path both fluidly connected to the direct flow lumen adjacent the first cassette port and between the first cassette port and the drip chamber and fluidly connected to the direct flow lumen adjacent the second cassette port and between the second cassette port and the drip chamber, such that fluid flowing through the fluid flow bypass path bypasses the drip chamber.

Aspects of the above blood component collection set include wherein the fluid flow bypass path comprises: a first bypass branch fluidly connected to the direct flow lumen adjacent the first cassette port; a second bypass branch fluidly connected to the direct flow lumen adjacent the second cassette port; and a fluid pressure annulus disposed between and fluidly connected to the first bypass branch and the second bypass branch. Aspects of the above blood component collection set include wherein the direct flow lumen comprises a first compliant region, disposed between a first connection with the first bypass branch and the drip chamber, that allows a first fluid control valve to occlude the direct flow lumen, wherein the direct flow lumen comprises a second compliant region, disposed between a second connection with the second bypass branch and the drip chamber, that allows a second fluid control valve to occlude the direct flow lumen, and wherein the direct flow lumen comprises a third compliant region, disposed in the first bypass branch, that allows a draw fluid control valve to occlude the first bypass branch. Aspects of the above blood component collection set include wherein, when drawing fluid from the donor: the first fluid control valve and the second fluid flow control valve are closed and occlude the direct flow lumen; and the draw fluid control valve is open and allows whole blood to pass through the fluid flow bypass path. Aspects of the above blood component collection set include wherein, when sending fluid to the donor: the first fluid control valve and the second fluid flow control valve are open and allow fluid to pass through the direct flow lumen; and the draw fluid control valve is closed and occludes the fluid flow bypass path. Aspects of the above blood component collection set include wherein, when drawing fluid from the donor in a subsequent draw, a portion of the fluid previously sent to the donor through the direct flow lumen is maintained in the drip chamber when the fluid passes through the fluid flow bypass path.

Embodiments include a method for moving fluids through a soft cassette comprising: providing a soft cassette, the soft cassette comprising: a first cassette port fluidly connected to a cassette inlet tubing; a second cassette port fluidly connected to a loop inlet tubing; a direct flow lumen fluidly connected to the first cassette port and the second cassette port; a drip chamber inter-disposed in the direct flow lumen such that the fluid passing through the direct flow lumen passes through the drip chamber; and a fluid flow bypass path both fluidly connected to the direct flow lumen adjacent the first cassette port and between the first cassette port and the drip chamber and fluidly connected to the direct flow lumen adjacent the second cassette port and between the second cassette port and the drip chamber, such that fluid flowing through the fluid flow bypass path bypasses the drip chamber; when drawing whole blood from a donor: receiving whole blood from the cassette inlet tubing at a first cassette port fluidly connected to the cassette inlet tubing; moving the whole blood through the fluid flow bypass path to the second cassette port; preventing whole blood from moving through the direct lumen; when returning red blood cells to the donor: receiving red blood cells from the loop inlet tubing at a second cassette port fluidly connected to the loop inlet tubing; moving the red blood cells through the direct flow lumen and the drip chamber to the first cassette port; and preventing red blood cells from moving through the fluid flow bypass path.

Aspects of the above method include wherein, when drawing fluid from the donor in a subsequent draw, a portion of the fluid previously sent to the donor through the direct flow lumen, when returning red blood cells to the donor, is maintained in the drip chamber when the whole blood again passes through the fluid flow bypass path.

Any one or more of the aspects/embodiments as substantially disclosed herein. optionally in combination with any one or more other aspects/embodiments as substantially disclosed herein.

One or more means adapted to perform any one or more of the above aspects/embodiments as substantially disclosed herein.

The present disclosure can provide a number of advantages depending on the particular aspect, embodiment, and/or configuration. By maintaining the speed of rotation of the centrifuge while moving the unneeded blood components back to the donor, the apheresis procedure can be reduced in time, possibly by 30% or more. This increase in efficiency allows for faster and more comfortable donations. With faster donation times, a donation center can obtain more donations in a typical day, which increases productivity and revenue. Further, donors are more likely to return to donate again if the donation is faster. Having faster donations may also allow donation centers to attract donors using other donation centers with slower donation speeds.

These and other advantages will be apparent from the disclosure.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "donor," as used herein, can mean any person providing a fluid, e.g., whole blood, to the apheresis system. A donor can also be a patient that also provides a fluid to the apheresis system temporarily while the fluid is processed, treated, manipulated, etc. before being provided back to the patient.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The term "computer-readable medium" as used herein refers to any tangible storage and/or transmission medium that participate in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

The term "module" as used herein refers to any known or later developed hardware, software, firmware, artificial intelligence, fuzzy logic, or combination of hardware and software that is capable of performing the functionality associated with that element.

The terms "determine", "calculate" and "compute," and variations thereof, as used herein, are used interchangeably and include any type of methodology, process, mathematical operation or technique.

It shall be understood that the term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The preceding is a simplified summary of the disclosure to provide an understanding of some aspects of the disclosure. This summary is neither an extensive nor exhaustive overview of the disclosure and its various aspects, embodiments, and/or configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and/or configurations of the disclosure are possible utilizing, alone or in combination, one or more of the features set forth above or described in detail below

BRIEF DESCRIPTION OF THE DRAWINGS

FIG. 5G shows a perspective view of a fluid component collection loop loading into a filler in accordance with embodiments of the present disclosure;

FIG. 5H shows a perspective view of a fluid component collection loop loaded in a filler in accordance with embodiments of the present disclosure;

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

DETAILED DESCRIPTION

Embodiments of the present disclosure will be described in connection with apheresis methods and systems. Embodiments below may be described with respect to separating blood components from whole blood. However, this example procedure is provided simply for illustrative purposes. It is noted that the embodiments are not limited to the description below. The embodiments are intended for use in products, processes, devices, and systems for separating any composite liquid. Accordingly, the present disclosure is not limited to separation of blood components from whole blood.

Figure 1:
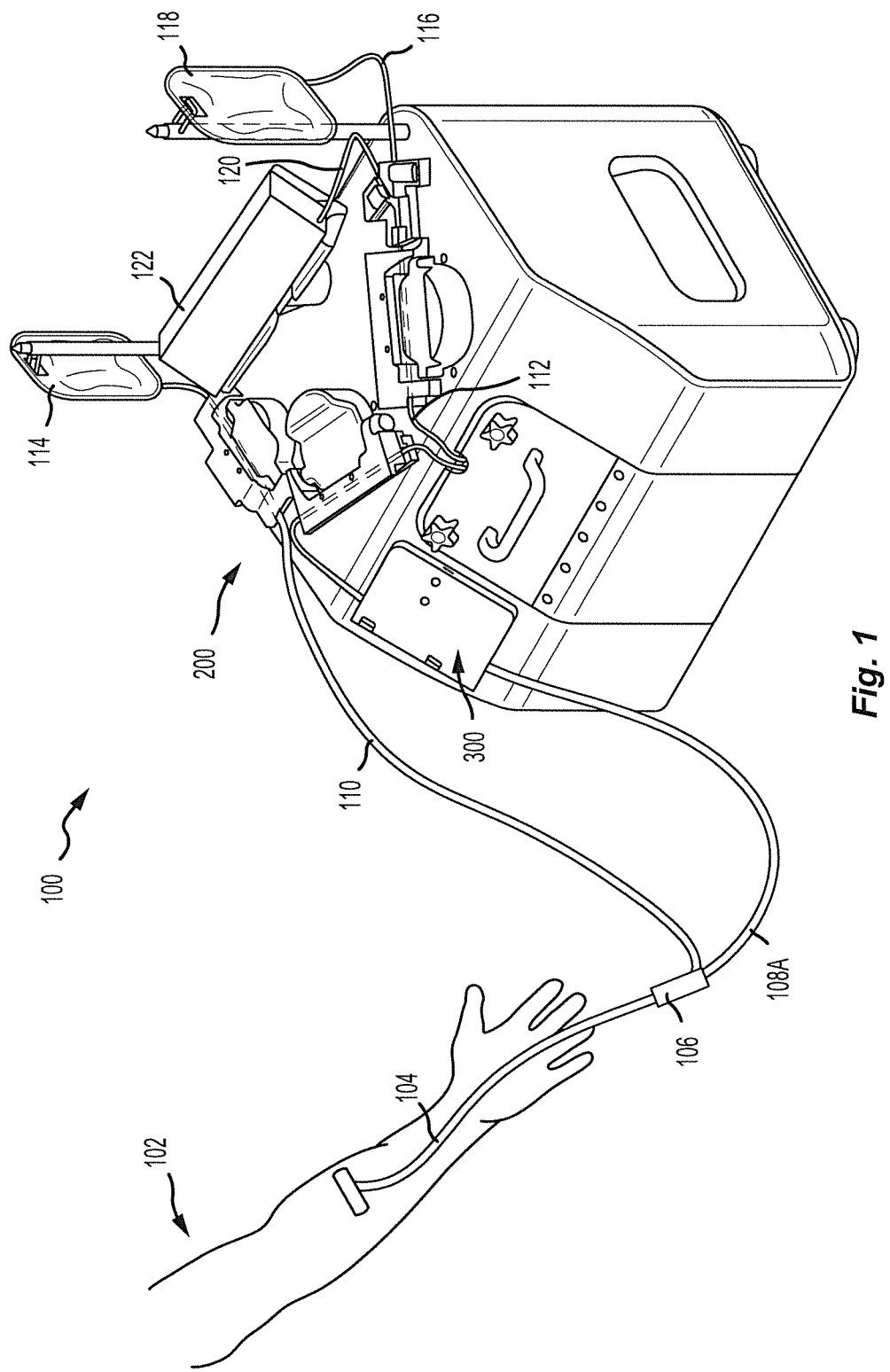
FIG. 1 shows a perspective view of an operating environment of an apheresis system in accordance with embodiments of the present disclosure.

Referring to FIG. 1, a perspective view of an operating environment 100 of an apheresis system 200 is shown in accordance with embodiments of the present disclosure. The operating environment 100 may include an apheresis system 200, a donor 102, and one or more connections (e.g., donor feed tubing 104, cassette inlet tubing 108A, anticoagulant tubing 110, etc.) running from the donor 102 to the apheresis system 200, and/or vice versa. As shown in FIG. 1, donor feed tubing 104 may be fluidly connected with at least one blood vessel, for example, a vein, of a donor 102 via venipuncture. For example, a cannula connected to an end of the donor feed tubing 104 may be inserted through the skin of the donor 102 and into a target site, or vein. This connection may provide an intravenous path for blood to flow from the donor 102 to the apheresis system 200, and/or for blood components to flow back to the donor 102. In some embodiments, the fluid paths and connections may form an extracorporeal tubing circuit of the apheresis system 200.

Blood supplied from the donor 102 may flow along the donor feed tubing 104 through a tubing connector 106 and along a cassette inlet tubing 108A into a soft cassette assembly 300. The soft cassette assembly 300 may include one or more fluid control paths and valves for selectively controlling the flow of blood to and/or from the donor 102. The apheresis system 200 may include an anticoagulant supply contained in an anticoagulant (AC) bag 114. The anticoagulant may be pumped at least through anticoagulant tubing 110 and the tubing connector 106 preventing the coagulation of blood in the apheresis system 200.

Anticoagulants can include one or more of, but are not limited to, citrate and/or unfractionated heparin. The AC bag and other bags or bottles described herein can be made from, for example, one or more of, but not limited to: polyvinyl chloride (PVC), plasticized-PVC, polyethylene, ethylene with vinyl acetate (EVA), rubber, silicone, thermoplastics, thermoplastic elastomer, polymers, copolymers, and/or combinations thereof. The volume of AC in the AC bag 114 may vary based on the various factors, including the mass of the donor 102, the volumetric flow of blood from the donor, etc. In one example, the volume in the AC bag 114 may be 250 to 500 mL, although the volume in the AC bag 114 may be more or less than this volume.

Figure 2A:
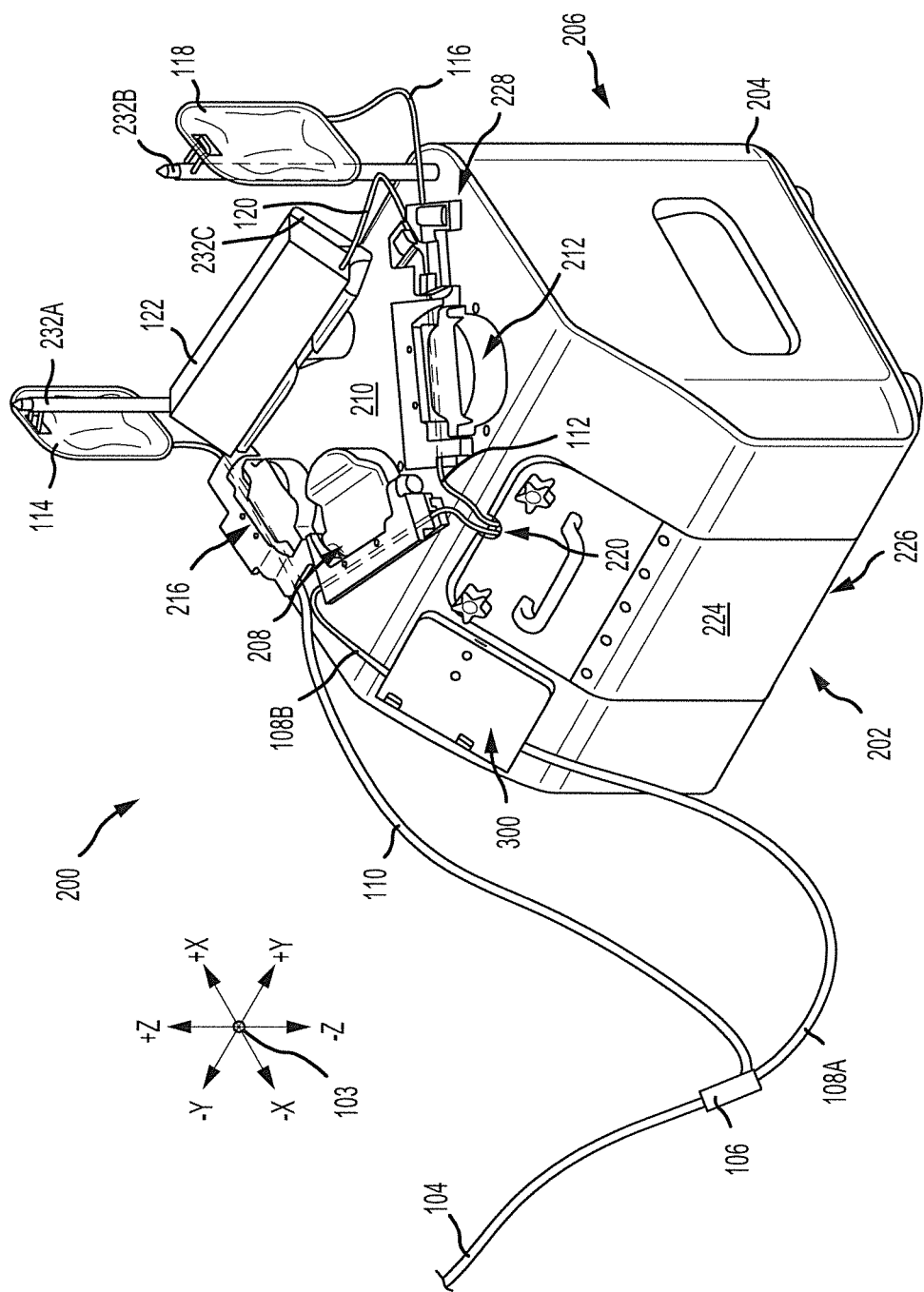
FIG. 2A is a perspective view of the apheresis system shown in FIG. 1.

In some embodiments, the apheresis system 200 may include a plasma collection bottle 122, or container, a saline fluid contained in a saline bag 118, and one or more lines or tubes 116, 120 (e.g., fluid conveying tubing, etc.) connecting the saline bag 118 and the plasma collection bottle 122 with the extracorporeal tubing circuit of the apheresis system 200. The amount of saline provided in the saline bag 118 can be 500 to 800 mL, although the volume in the saline bag 118 may be more or less than this volume. An example donation of a blood component, e.g., plasma, may be 880 mL. Thus, the plasma collection bottle 122 may hold at least this amount of plasma. In some embodiments, the plasma collection bottle 122 may include a connection point disposed at, adjacent to, or in physical proximity to, a substantially bottommost portion of the plasma collection bottle 122 (e.g., when the plasma collection bottle 122 is installed in the plasma collection cradle 232C, as shown in FIG. 2A). The connection point may include one or more connectors that are configured to interconnect with the plasma tubing 120 to receive and/or convey plasma. The disposition of the connection point at the bottom of the plasma collection bottle 122 can allow plasma contained in the plasma collection bottle 122 to move out of the plasma tubing 120 back through the lines, as described herein, without trapping air bubbles, etc. In some embodiments, the plasma collection bottle 122 may be configured as a flexible bag, rigid container, and/or other container, and thus, the plasma collection bottle 122 is not limited to bottles or bottle-like containers.

FIG. 2A shows a perspective view of the apheresis system 200 described in FIG. 1. The apheresis system 200 may provide for a continuous whole blood separation process. In one embodiment, whole blood may be withdrawn from a donor 102 and substantially continuously provided to a blood component separation device of the apheresis system 200 where the blood may be separated into various components and at least one of these blood components may be collected from the apheresis system 200. In some embodiments, one or more of the separated blood components may be either collected, for subsequent use, or returned to the donor 102. The blood may be withdrawn from the donor 102 and directed into a centrifuge of the apheresis system 200 through an opening 220 in an access panel 224 of the apheresis system 200. In one embodiment, the tubing 104, 108A, 108B, 112, 116, 120, used in the extracorporeal tubing circuit may together define a closed, sterile, and disposable system, or blood component collection set, which may be further described hereinafter.

Examples of apheresis, plasmapheresis, and other separation systems that may be used with embodiments of the present disclosure, e.g., as apheresis system 200, include, but are not limited to, the SPECTRA OPTIA® apheresis system, COBE® spectra apheresis system, and the TRIMA ACCEL® automated blood collection system, all manufactured by Terumo BCT, of Lakewood, Colorado.

Operation of the various pumps, valves, and blood component separation device, or centrifuge, may be controlled by one or more processors included in the apheresis system 200, and may advantageously comprise a plurality of embedded computer processors that are part of a computer system. The computer system may also include components that allow a user to interface with the computer system, including for example, memory and storage devices (RAM, ROM (e.g., CD-ROM, DVD), magnetic drives, optical drives, flash memory, etc.); communication/networking devices (e.g., wired such as modems/network cards, or wireless such as Wi-Fi); input devices such as keyboard(s), touch screen(s), camera(s), and/or microphone(s); and output device(s) such as display(s), and audio system(s), etc. To assist the operator of the apheresis system 200 with various aspects of its operation, the embodiment of the blood component separation device, or centrifuge, may include a graphical user interface with a display that includes an interactive touch screen.

The apheresis system 200 may include a housing 204 and/or structural frame, a cover 210, an access panel 224 disposed at a front 202 and/or rear 206 of the apheresis system 200, and one or more supports 232A-C including hooks, rests, cradles, arms, protrusions, plates, and/or other support features for holding, cradling, and/or otherwise supporting a bag or container 114, 118, 122. In some embodiments, the features of the apheresis system 200 may be described with reference to a coordinate system 103 and/or one or more axes thereof. The housing 204 may include a machine frame (e.g., made of welded, bolted, and/or connected structural elements, extruded material, beams, etc.) to which one or more panels, covers 210, doors, subassemblies, and/or components are attached. In one embodiment, at least one panel of the apheresis system 200 may include a mounting surface for the soft cassette assembly 300, one or more pumps 208, 212, 216, and/or a fluid valve control system 228 (e.g., plasma and saline valve control, etc.).

The access panel 224 may include one or more handles, locks, and a pivoting or hinged axis 226 (e.g., a door hinge, piano hinge, continuous hinge, cleanroom hinge, etc.). In any event, the access panel 224 may be selectively opened to provide access to an interior of the apheresis system 200, and more specifically to a blood separation assembly, or centrifuge. In one embodiment, the access panel 224 may provide access to load and/or unload the centrifuge with one or more components in the blood component collection set. Details of the centrifuge are described in greater detail at least with respect to FIGS. 4A-4L herein.

The inside of the apheresis system 200 may be separated into at least a centrifuge portion and a controls portion. For instance, the centrifuge portion may include a cavity configured to receive the centrifuge, rotation motor, and associated hardware. This area may be physically separated from the controls portion via one or more walls of the cavity. In some embodiments, access to the controls portion (e.g., configured to house or otherwise contain the motor controller, CPU or processor(s), electronics, wiring, etc.) may be provided via a securely fastened panel of the housing 204, and/or panel separate from the access panel 224.

In some embodiments, the apheresis system 200 may include a number of pumps 208, 212, 216 configured to control the flow of fluid (e.g., blood and/or blood components, anticoagulant, saline, etc.) through the apheresis system 200. For instance, the apheresis system 200 may include a draw pump 208 that controls blood flow to and/or from the donor 102 into the centrifuge of the apheresis system 200. The draw pump 208 may engage with a portion of the loop inlet tubing 108B disposed between the soft cassette assembly 300 and the centrifuge of the apheresis system 200. In some embodiments, the apheresis system 200 may include a return pump 212 configured to control a flow of separated blood components (e.g., plasma, etc.) from the centrifuge to a plasma collection bottle 122 and/or vice versa. Additionally or alternatively, the return pump 212 may control a flow of saline (e.g., supplied from a saline bag 118) throughout the blood component collection set and/or apheresis system 200. The anticoagulant pump 216 may engage with a portion of the anticoagulant tubing 110 to selectively control the flow of anticoagulant throughout the blood component collection set of the apheresis system 200. As shown in FIG. 2A, the pumps 208, 212, 216 can be disposed at least partially on a top cover 210 of the apheresis system 200.

Figure 2C:
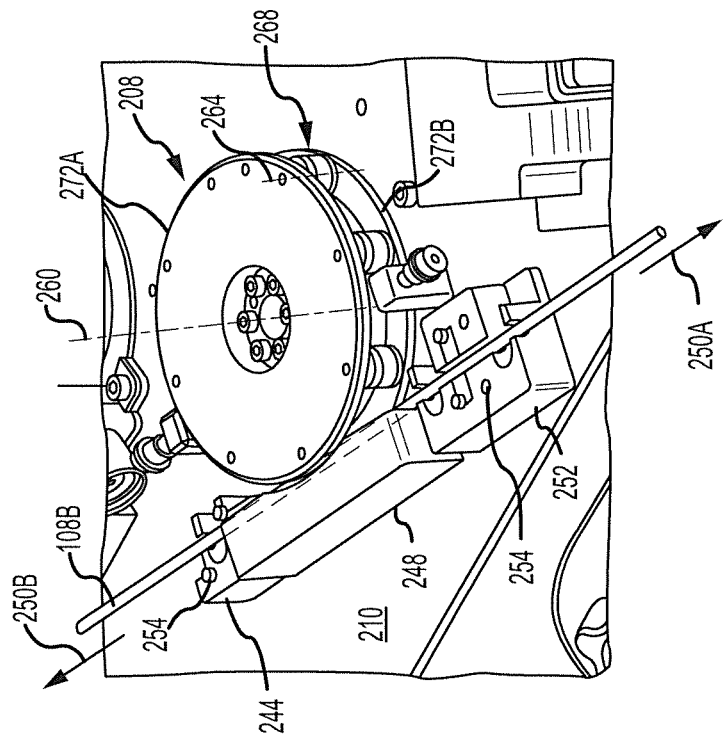
FIG. 2C is a second detail perspective view of a pump of an apheresis system in accordance with embodiments of the present disclosure.
Figure 2B:
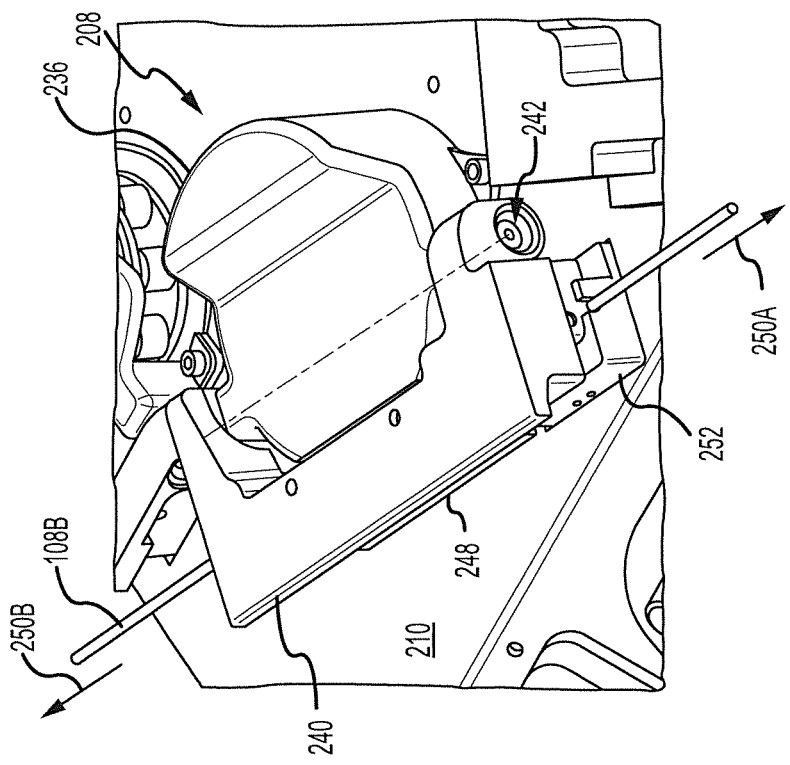
FIG. 2B is a first detail perspective view of a pump of an apheresis system in accordance with embodiments of the present disclosure.

FIGS. 2B and 2C show various perspective views of a pump 208, 212, 216 of the apheresis system 200 in accordance with embodiments of the present disclosure. Although the draw pump 208 is shown and described in conjunction with FIGS. 2B and 2C, it should be appreciated that the other pump assemblies of the apheresis system 200, i.e., the return pump 212 and the anticoagulant pump 216, may include a substantially similar, if not identical, construction to the draw pump 208 described.

The draw pump 208 may include a pump cover 236 or housing configured to at least partially enclose the moving elements of the draw pump 208. In some embodiments, the pump cover 236 may include a hinged tubing guard 240 that is configured to open and close about a tubing guard pivot axis 242. In one embodiment, the tubing guard 240 may be attached to the pump cover 236 via one or more fasteners disposed along the tubing guard pivot axis 242. As shown in FIGS. 2B and 2C, blood provided by a donor 102 may be conveyed, or drawn, by the draw pump 208 into a centrifuge in a first draw or centrifuge direction 250A. Additionally or alternatively, blood or other fluid may be conveyed, or drawn, by the draw pump 208 toward the donor 102 in a donor direction 250B, opposite the centrifuge direction 250A.

In some embodiments, the draw pump 208 and/or other pumps 212, 216 may be a tubing pump, peristaltic pump, diaphragm pump, and/or other pump configured to manipulate the flow of fluid (e.g., blood, blood components, anticoagulant, saline, etc.) in at least a portion of tubing. For example, the pumps 208, 212, 216 may include a motor operatively interconnected with a rotating tubing contact assembly. In operation, the tubing (e.g., loop inlet tubing 108B, loop exit tubing 112, anticoagulant tubing 110, etc.) may be inserted into a lead tubing guide 244, a tubing pressure block 248, and an end tubing guide 252 adjacent to the rotating tubing contact head. In one embodiment, the tubing pressure block 248 may be moved in a direction away from the rotating tubing contact head or pump 208, 212, 216 providing a loading clearance area, or vice versa. The rotating tubing contact head may comprise a number of rotary pressure rollers 268 configured to rotate about respective pressure roller rotation axes 264. Each of the rotary pressure rollers 268 may be disposed between a first rotary pump plate 272A and a second rotary pump plate 272B, where the plates 272A, 272B are configured to rotate about a pump rotation axis 260. In some embodiments, the rotary pressure rollers 268 may be disposed at a periphery of the rotating pump plates 272A, 272B.

The one or more of the pumps 208, 212, 216 may include, or operate similarly to, the Pulsafeeder® model UX-74130 peristaltic pump, Pulsafeeder® MEC-O-MATIC series of pumps, all manufactured by Pulsafeeder Inc., of Punta Gorda, Florida, without limitation. Other examples of pumps 208, 212, 216 may include, but are in no way limited to, the INTEGRA DOSE IT laboratory peristaltic pump manufactured by INTEGRA Biosciences AG, of Switzerland, and WELCO WP1200, WP1100, WP1000, WPX1, and/or WPM series of peristaltic pumps all manufactured by WELCO Co., Ltd., of Tokyo, Japan.

Once the tubing is loaded into the lead tubing guide 244, the tubing pressure block 248, and/or the end tubing guide 252, at least some of the rotary pressure rollers 268 may be caused to engage with, contact, or otherwise compress the tubing disposed between the rotating tubing contact head and the tubing pressure block 248. As the rotary pump plates 272A, 272B rotate about the pump rotation axis 260 the rotary pressure rollers 268 may compress a portion of the tubing between the pump 208, 212, 216 and the tubing pressure block 248 positively displacing fluid inside the portion of the tubing in a particular direction 250A, 250B as the rotary pressure rollers 268 move. For instance, as the rotary pump plates 272A, 272B rotate in a counterclockwise direction about the pump rotation axis 260, the rotation of the rotary pressure rollers 268 compressing the tubing between the rotary pressure rollers 268 and the tubing pressure block 248 may displace, or pump, fluid in the centrifuge direction 250A. As another example, as the rotary pump plates 272A, 272B rotate in a clockwise direction about the pump rotation axis 260, the rotation of the rotary pressure rollers 268 compressing the tubing between the rotary pressure rollers 268 and the tubing pressure block 248 may displace, or pump, fluid in the donor direction 250B. When not actively pumping, the pump 208 can be maintained in a state where at least one rotary pressure roller 268 continues to occlude the tubing 108B or in a state where no rotary pressure roller 268 occludes the tubing 108B. Thus, the pump 208, based on the state when motionless, can also act as a "valve" to prevent or allow fluid movement. This ability may also be available with pumps 212 and 216.

The tubing guard 240 and the pump cover 236 may serve to protect an operator (e.g., phlebotomist, apheresis technician, etc.) and/or donor 102 from incidental contact with one or more moving parts of the pumps 208, 212, 216. In one embodiment, the tubing guard 240 may be held in a closed position via one or more guard closure features 254 disposed in the tubing guard 240, the lead tubing guide 244, tubing pressure block 248, and/or the end tubing guide 252. In some cases, these guard closure features 254 may be magnets contained in the tubing guard 240, the lead tubing guide 244, tubing pressure block 248, and/or the end tubing guide 252. In some embodiments, the pump 208, 212, 216 may be stopped or prevented from moving/operating when the tubing guard 240 is open. In this embodiment, a guard closed sensor may be included in the guard closure feature 254, the guides 244, 252, and/or the tubing pressure block 248.

One or more fluid control valves may be used to control the routing or flow direction of fluid conveyed throughout the tubing of the apheresis system 200. In some embodiments, the apheresis system 200 may include a plasma and saline valve control system 228 disposed adjacent to the saline bag 118 and/or the plasma collection bottle 122. The plasma and saline valve control system 228 is shown in the detail perspective view of FIG. 2D.

Figure 2D:
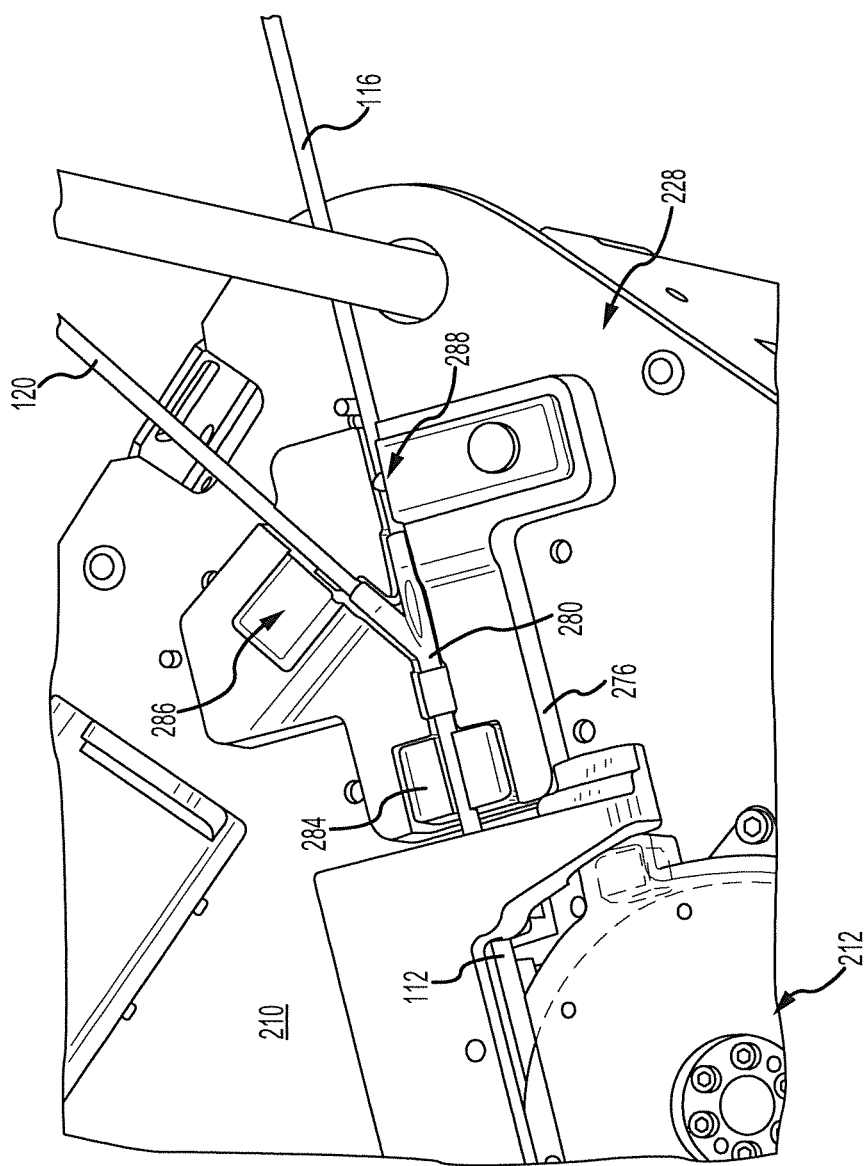
FIG. 2D is a detail perspective view of a fluid valve control system in accordance with embodiments of the present disclosure.

As shown in FIG. 2D, the loop exit tubing 112 may pass through the return pump 212 and interconnect with a saline and plasma tubing y-connector 280. The saline and plasma tubing y-connector 280 may allow connection of the loop exit tubing 112 to a saline tubing 116 line and a plasma tubing 120 line. The plasma and saline valve control system 228 may include an air detection sensor 284 disposed at a first end of the saline and plasma valve housing 276 and surrounding a portion of the loop exit tubing 112. The air detection sensor 284 can be any light, ultrasonic, or other type of sensor that can detect the presence of fluid or air in the loop exit tubing 112 and provide that signal to a controller of the apheresis system 200. Types of air detection sensors 284 can include, for example, the SONOCHECK ABD05, made by SONOTEC US Inc., or another similar sensor.

The saline and plasma valve housing 276 may include a number of receiving features (e.g., grooves, channels, receptacles, etc.) that receive a portion of tubing 112, 116, 120, and/or the saline and plasma tubing y-connector 280. Upon detecting air in the loop exit tubing 112, the plasma and saline valve control system 228 may selectively actuate one or more of the fluid control valves 286, 288. In some embodiments, the detection of air via the air detection sensor 284 may be used to signal an operation step and/or trigger a step in a control method as described herein.

The plasma flow control valve 286 and/or the saline flow control valve 288 may be a solenoid valve, linear actuator, pinch valve, clamp valve, tubing valve, and/or other actuatable valve configured to selectively alter, e.g., occlude, a fluid passage associated with a particular portion of tubing 112, 116, 120. As shown in FIG. 2D, the plasma flow control valve 286 may be configured to pinch a portion of the plasma tubing 120 at least partially contained in a receiving feature of the saline and plasma valve housing 276. The saline flow control valve 288 may be configured to pinch a portion of the saline tubing 116 at least partially contained in a receiving feature of the saline and plasma valve housing 276. In any event, the control valves 286, 288 may include an actuatable extendable finger that moves from a retracted, or partially retracted, position to an extended, or partially extended, position to pinch the portion of tubing contained in the saline and plasma valve housing 276. While the control valves 286, 288 may completely pinch the tubing (e.g., completely restricting fluid flow therethrough), it should be appreciated that the control valves 286, 288 may be partially actuated to a position that partially restricts fluid flow through a portion of the tubing.

Figure 3A:
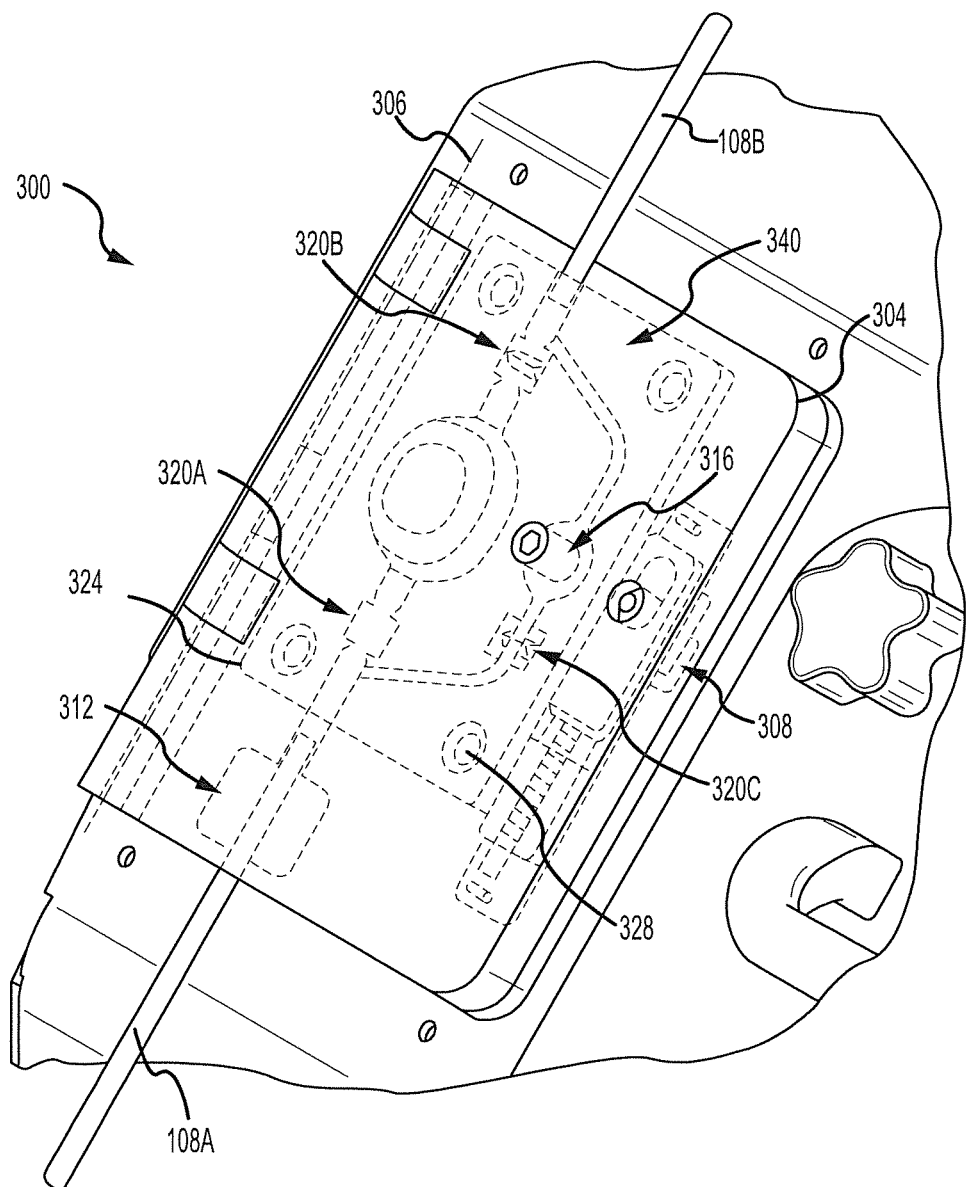
FIG. 3A is a detail perspective view of a disposable soft cassette assembly in accordance with embodiments of the present disclosure.

Referring now to FIG. 3A, a detail perspective view of a disposable soft cassette assembly 300 is shown in accordance with embodiments of the present disclosure. The soft cassette assembly 300 may include a baseplate and a cassette access door 304 that is attached to the baseplate via at least one hinge and/or cassette access door latch 308. In some embodiments, the cassette access door 304 may be unlocked via actuating the cassette access door latch 308 and pivoted about a cassette access door hinge axis 306. The soft cassette assembly 300 may be configured with one or more soft cassette receiving features 324 for at least partially containing and/or locating a soft cassette 340 therein. The soft cassette 340 may be a part of the blood component collection set described herein. For instance, the soft cassette 340 may be disposed between the cassette inlet tubing 108A and the loop inlet tubing 108B of the extracorporeal tubing circuit. In some embodiments, the soft cassette 340 may provide one or more features for controlling the flow of blood and/or blood components from a donor 102 to the apheresis system 200, and/or vice versa.

The soft cassette assembly 300 may include an air detection sensor 312, a fluid sensor 316, and one or more fluid control valves 320A-C configured to control a routing or flow direction of fluid through the soft cassette 340. In some embodiments, these components may be embedded in the cassette access door 304, the baseplate, and/or a portion of the housing 204 of the apheresis system 200. Similar to the guard closure feature 254 described in conjunction with FIGS. 2B-2C, the soft cassette assembly 300 may include one or more door closure features 328. These features 328 may include, but are not limited to, magnetic catches, protrusions, tabs and slots, and/or other connections. In one embodiment, the door closure features 328 may include pressure contact surfaces configured to hold or at least partially position a soft cassette 340 inside the soft cassette assembly 300.

Examples of the valves 320A-C may include, but are in no way limited to, a solenoid valve, linear actuator, pinch valve, clamp valve, tubing valve, and/or other actuatable valve configured to selectively alter, e.g., occlude, a fluid passage (e.g., cross-sectional area, etc.) associated with a particular portion of the soft cassette 340. The soft cassette assembly 300 may include a first fluid control valve 320A configured to pinch a portion of the soft cassette 340 adjacent to a cassette inlet tubing 108A. The second fluid control valve 320B may be configured to pinch a portion of the soft cassette 340 adjacent to the loop inlet tubing 108B. A draw fluid control valve 320C may be configured to pinch a portion of the soft cassette 340 along a branch tubing extending from a point adjacent to the cassette inlet tubing 108A to a point adjacent to the loop inlet tubing 108B. In any event, the valves 320A-C may include an actuatable extendable finger that moves from a retracted, or partially retracted, position to an extended, or partially extended, position to pinch the portion of the soft cassette 340 contained in the soft cassette assembly 300. While the valves 320A-C may completely pinch flow paths in the soft cassette 340 (e.g., completely restricting fluid flow therethrough), it should be appreciated that the valves 320A-C may be partially actuated to a position that partially restricts fluid flow through a portion of the soft cassette 340.

The sensors 312, 316 may be one or more of an ultrasonic detector, pressure sensor, magnetic position sensor, and/or the like. In some cases, the fluid sensor 316 may determine whether fluid is present in the soft cassette 340 based on a position of a magnet relative to a portion of the soft cassette 340. For instance, when the portion of the soft cassette 340 is filled with a fluid, the magnet may be disposed at a first position from a surface of the soft cassette 340. On the other hand, when the portion of the soft cassette 340 is filled with air, the force from the magnet may compress the portion of the soft cassette 340 to a second position closer to the surface of the soft cassette 340 than the first position. In any event, the detection of air or fluid via the air detection sensor 312 and the fluid sensor 316, respectively, may be used to signal an operation step and/or trigger a step in a control method as described herein.

Figure 3B:
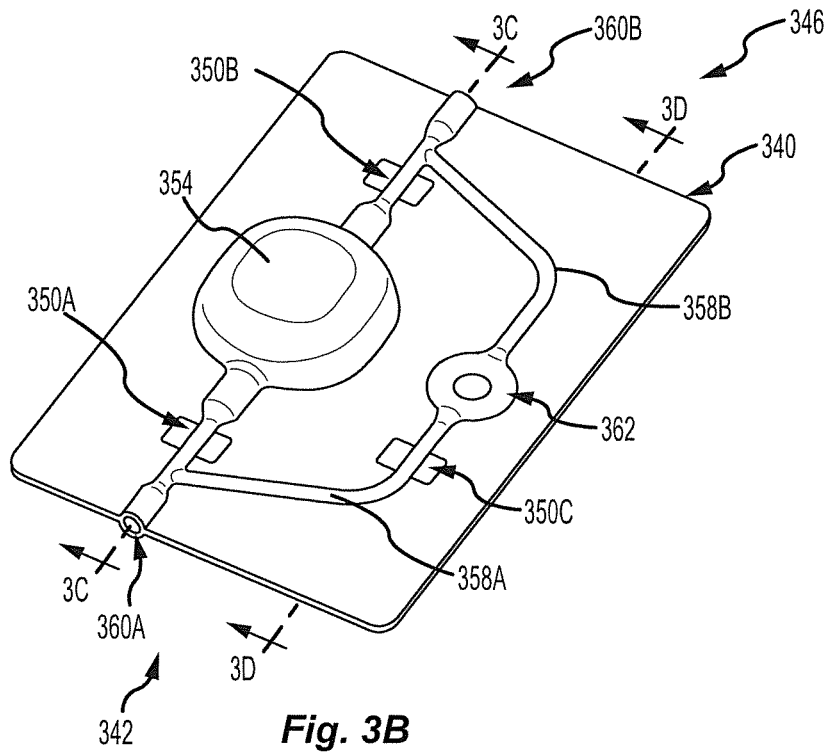
FIG. 3B is a perspective view of a disposable soft cassette in accordance with embodiments of the present disclosure.
Figure 3C:
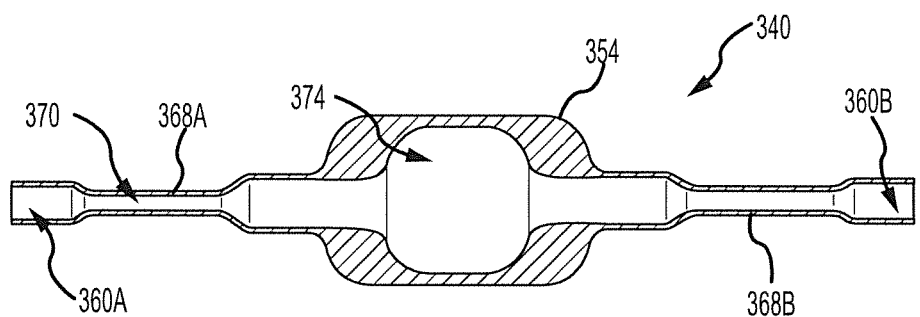
FIG. 3C is an elevation section view taken through line 3C of FIG. 3B.
Figure 3D:
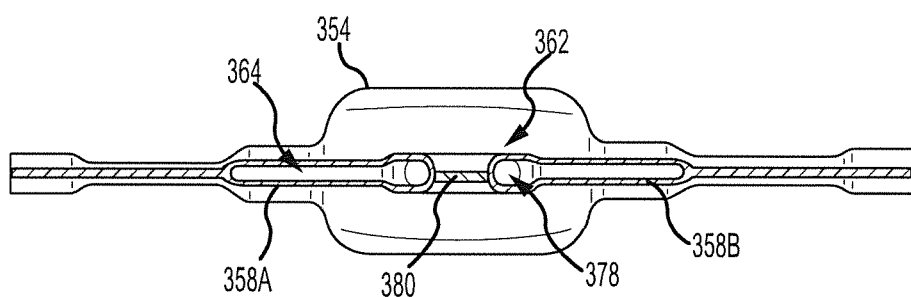
FIG. 3D is an elevation section view taken through line 3D of FIG. 3B.

FIGS. 3B-3D show various views of a soft cassette 340 in accordance with embodiments of the present disclosure. As provided above, the soft cassette 340 may be part of the blood component collection set. For instance, the soft cassette 340 may be a disposable component used in the blood separation methods described herein. In some embodiments, the soft cassette 340 may be made from a substantially compliant and/or flexible material. The compliant material may be chemically inert and/or be capable of withstanding sterilization and cleaning operations, temperatures, and/or treatments. The soft cassette 340 may be made from polyvinyl chloride (PVC), plasticized-PVC, polyethylene, ethylene with vinyl acetate (EVA), rubber, silicone, thermoplastics, thermoplastic elastomer, polymers, copolymers, and/or combinations thereof. In some embodiments, the soft cassette 340 may be molded, rotomolded, cast, injection molded, or otherwise formed from one or more of the materials described above.

The soft cassette 340 may include a first cassette port 360A, a second cassette port 360B, and a direct flow lumen 370 running between the first and second cassette ports 360A-B. In some embodiments, the first and/or second cassette ports 360A-B may be configured to receive and/or fluidly couple with one or more tubes of the blood component collection set. For example, the first cassette port 360A may couple with the cassette inlet tubing 108A and the second cassette port 360B may couple with the loop inlet tubing 108B. These couplings may be air and/or fluid tight. In one embodiment, the first and/or second cassette ports 360A-B may include an aperture disposed within the soft cassette 340 that is configured to elastically stretch around an end of the tubing (e.g., cassette inlet tubing 108A, loop inlet tubing 108B, etc.).

Blood supplied by the donor 102 may be directed along one or more fluid paths disposed within the soft cassette 340. In one embodiment, the blood may be directed along the direct flow lumen 370 from the first cassette port 360A to the second cassette port 360B. In some embodiments, this flow path may direct the blood through the drip chamber 354 of the soft cassette 340. In some embodiments, blood and/or other fluids returned to the donor 102 may be directed along the direct flow lumen 370 from the second cassette port 360B to the first cassette port 360A.

The soft cassette 340 may include a fluid flow bypass path provided by a first bypass branch 358A having a bypass flow lumen 364 that is fluidly connected to a portion of the direct flow lumen 370 adjacent to the first cassette port 360A or as part of the first cassette port 360A. In some embodiments, the bypass flow lumen 364 may run from a point of the direct flow lumen 370 adjacent to the first cassette port 360A, along the first bypass branch 358A, through a fluid pressure annulus 362 to a second bypass branch 358B, and then reconnect to the direct flow lumen 370 at a point adjacent to the second cassette port 360B or as part of the second cassette port 360B. As the name suggests, the bypass flow lumen 364 provides a flow path within the soft cassette 340 that bypasses the drip chamber 354.

Controlling the flow path, or directing fluid, within the soft cassette 340 may include actuating the fluid control valves 320A-C of the soft cassette assembly 300 to interact with various compliant regions 350A-C blocking and/or opening portions of the direct flow lumen 370 and/or bypass flow lumen 364. The first compliant region 350A provides a pinch valve area at a point along the direct flow lumen 370 between the first cassette port 360A and the drip chamber 354 near a first cassette end 342 of the soft cassette 340. When the first fluid control valve 320A is actuated, the valve 320A may pinch the direct flow lumen 370 closed at this first compliant region 350A, restricting or completely preventing the flow of fluid at this point in the soft cassette 340. The second compliant region 350B provides a pinch valve area at a point along the direct flow lumen 370 between the second cassette port 360B and the drip chamber 354 near a second cassette end 346 (e.g., opposite the first cassette end 342). When the second fluid control valve 320B is actuated, the valve 320B may pinch the direct flow lumen 370 closed at this second compliant region 350B, restricting or completely preventing the flow of fluid at this point in the soft cassette 340. As can be appreciated, the third compliant region 350C disposed along the first bypass branch 358A adjacent to the fluid pressure annulus 362 may provide a pinch valve area at a point along the bypass flow lumen 364. When the draw fluid control valve 320C is actuated, the valve 320C may pinch the bypass flow lumen 364 closed at this third compliant region 350C, restricting or completely preventing the flow of fluid through the bypass flow lumen 364.

As shown in the elevation section view of FIG. 3C, taken through a plane running through the direct flow lumen 370 and drip chamber 354, the direct flow lumen 370 runs from the first cassette port 360A through the inner chamber volume 374 of the drip chamber 354 to the second cassette port 360B. The direct flow lumen 370 may be formed as a fluid passage running inside the first tubing section 368A, the inner chamber volume 374, and the second tubing section 368B of the soft cassette 340.

In some embodiments, the bypass path of the soft cassette 340 may include a fluid pressure annulus 362 through which fluid can flow from the first bypass branch 358A to the second bypass branch 358B, and/or vice versa. In one embodiment, a pressure diaphragm 380 may be formed in the material of the soft cassette 340 an area within, or adjacent to, the fluid pressure annulus 362. The fluid pressure annulus 362 and pressure diaphragm 380 are illustrated in the elevation section view of FIG. 3D taken through a plane running through the fluid pressure annulus 362 and a portion of the first and second bypass branches 358A-B. The pressure diaphragm 380 may provide a contact, or measurement, surface for the fluid sensor 316 to detect whether the fluid pressure annulus 362 and/or the bypass flow lumen 364 includes an amount of fluid, air, and/or combinations thereof. As provided above, as fluid fills a portion of the fluid pressure annulus 362, the fluid may provide greater resistance to movement than when the fluid pressure annulus 362 is filled with air. This difference in resistance may be measured via the fluid sensor 316 to determine, among other things, an amount and/or type of fluid (e.g., air, blood, etc.) in the bypass flow lumen 364 and/or the fluid pressure annulus 362.

Figure 4A:
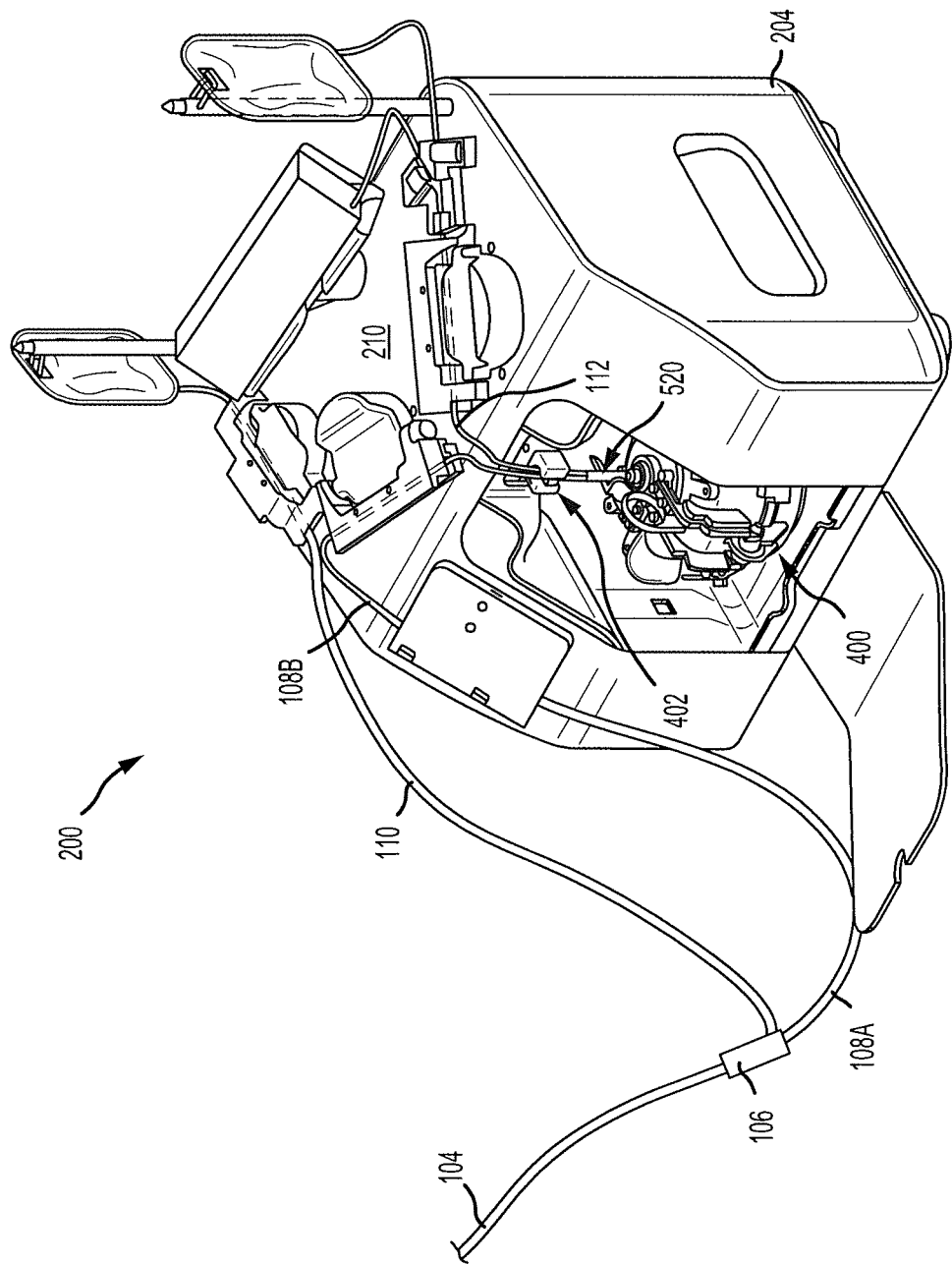
FIG. 4A shows a perspective view of a centrifuge assembly in an apheresis system in accordance with embodiments of the present disclosure.

FIG. 4A shows a perspective view of a centrifuge assembly 400 of the apheresis system 200 in accordance with embodiments of the present disclosure. The centrifuge assembly 400 may be disposed in an interior space of the apheresis system 200. The interior space may be at least partially enclosed with one or more elements of the housing 204 and/or centrifuge chamber. Access to the interior space and the centrifuge assembly 400 may be provided via the access panel 224 disposed at the front 202 of the apheresis system 200. For example, the access panel 224 of FIG. 4A is shown in an open position, opened along hinged axis 226. As provided above, the hinged axis 226 may correspond to a door hinge, continuous hinge, cleanroom hinge, and/or some other panel hinge.

The centrifuge assembly 400 may be operatively mounted inside the apheresis system 200 such that the assembly 400 is capable of rotating relative to the housing 204 and/or other elements of the apheresis system 200. The centrifuge assembly 400 may be loaded with one or more portions of the blood component collection set by routing tubing (e.g., loop inlet tubing 108B and loop exit tubing 112, etc.) into the interior space of the apheresis system 200 (e.g., via the opening 220 shown in FIG. 2A), connecting a portion of the blood component collection loop 520 to the fixed loop connection 402 and inserting the blood component collection bladder 536 into a filler 460. The fixed loop connection 402 maintains the loop inlet tubing 108B and the loop exit tubing 112 in a fixed position and may prevent twisting of the tubing 108B, 112 outside of the apheresis system 200. In some embodiments, the blood component collection loop 520 may be interconnected to the fixed loop connection 402 via one or more keyed features or positive location features.

Figure 4B:
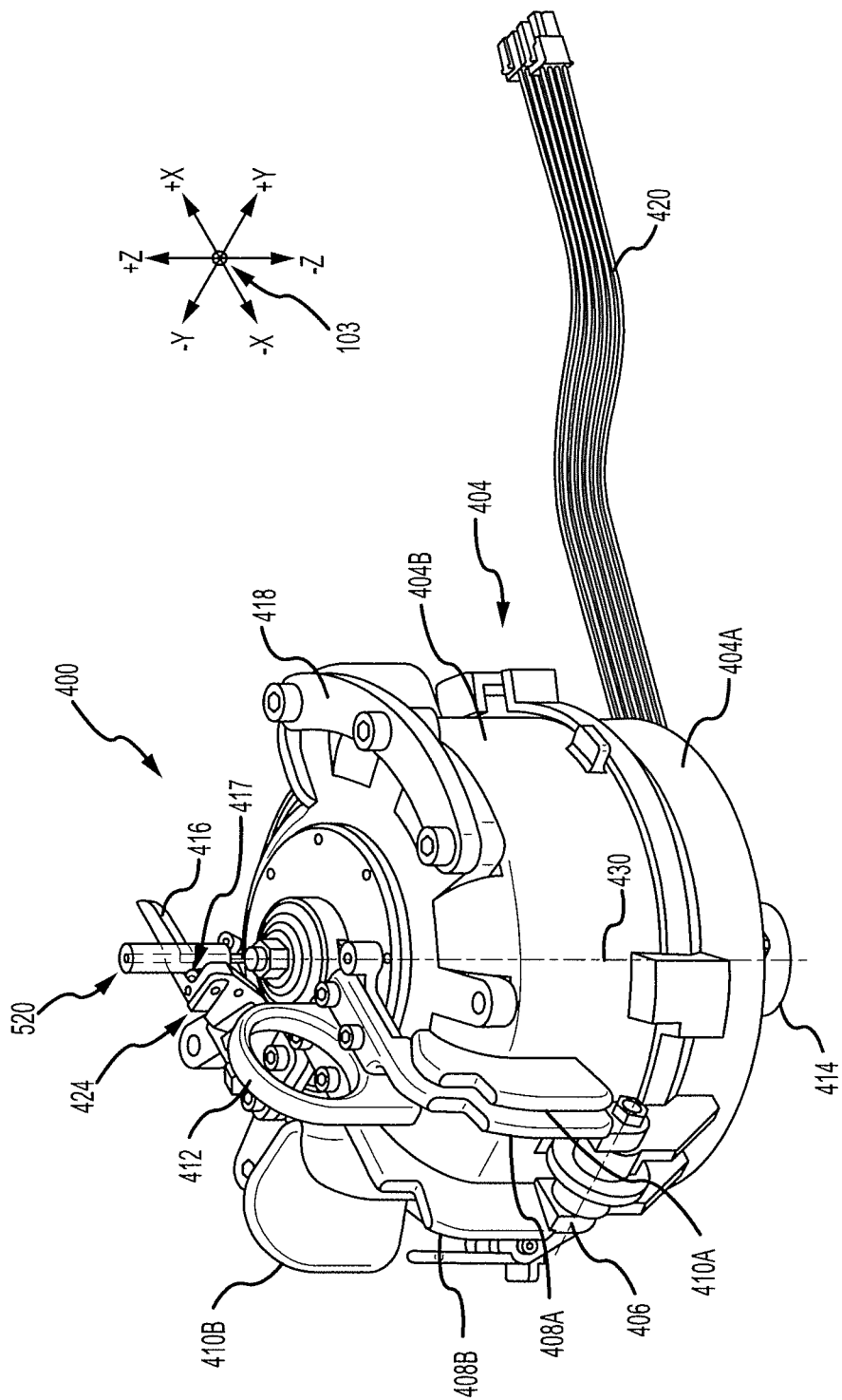
FIG. 4B shows a front perspective view of the centrifuge assembly shown in FIG. 4A.
Figure 4C:
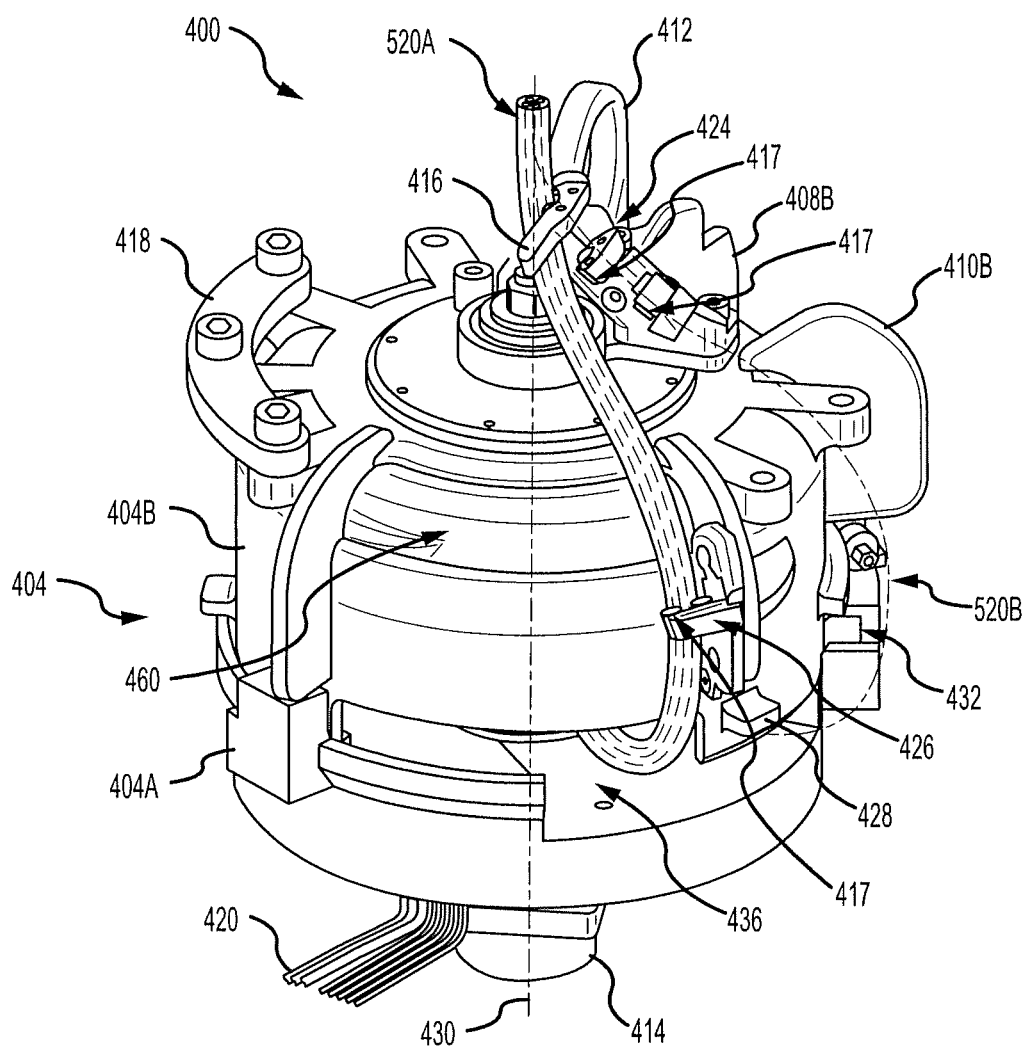
FIG. 4C shows a rear perspective view of the centrifuge assembly shown in FIG. 4A.

FIGS. 4B-4C show various perspective views of the centrifuge assembly 400 separate from the apheresis system 200 for the sake of clarity in description. The centrifuge assembly 400 may include a centrifuge split-housing 404 comprising a lower housing 404A pivotally connected to an upper housing 404B. The upper housing 404B may open to provide access for loading a blood component collection bladder or other component of the blood component collection set into the centrifuge assembly 400. In some embodiments, the upper housing 404B may pivot about the split-housing pivot axis 406 (e.g., configured as a hinge, pin, fastener, shoulder bolt, etc.).

The different halves (e.g., the lower housing 404A and upper housing 404B) of the centrifuge split-housing 404 may be configured to lock and/or unlock together. Unlocking the upper housing 404B from the lower housing 404A may provide access to an interior of the centrifuge assembly 400. This selective locking may be achieved by rotating the upper housing 404B relative to the lower housing 404A about the centrifuge rotation axis 430. Although the centrifuge split-housing 404 is shown in FIGS. 4B-4C in an unlocked state, it should be appreciated that the upper housing 404B can be rotated (e.g., in a counterclockwise direction) about the centrifuge rotation axis 430 to engage one or more locking tabs 428 or elements of the upper housing 404B with locking slots 432 disposed in the lower housing 404A (as shown in FIG. 4C). When in the unlocked position, the upper housing 404B may be opened, or pivoted, about the split-housing pivot axis 406 to load the centrifuge assembly 400 with a blood component collection loop 520 and/or a blood component collection bladder 536. When in the locked position, the upper housing 404B is rotationally locked relative to the lower housing 404A, and the two halves of the centrifuge split-housing 404 may spin together, locked in unison, during a centrifuge or blood separation operation.

The centrifuge assembly 400 may include at least one clockwise rotation stop 408A, counterclockwise rotation stop 408B, upper housing clockwise rotation flag 410A, and/or upper housing counterclockwise rotation flag 410B. In some embodiments, the rotation stops 408A, 408B may be rotationally fixed relative to the centrifuge rotation axis 430 of the lower housing 404A. The rotation flags 410A, 410B may be attached, or formed in, the upper housing 404B and configured to contact respective rotation stops 408A, 408B to prevent over-rotation of the upper housing 404B relative to the lower housing 404A when locking and/or unlocking the two halves of the centrifuge split-housing 404 together. For instance, upon rotating the upper housing 404B in a clockwise, or unlocking, direction about the centrifuge rotation axis 430, a portion of the upper housing clockwise rotation flag 410A may contact the clockwise rotation stop 408A preventing further rotation in the clockwise direction. Additionally or alternatively, upon rotating the upper housing 404B in a counterclockwise, or locking, direction about the centrifuge rotation axis 430, a portion of the upper housing counterclockwise rotation flag 410B may contact the counterclockwise rotation stop 408B preventing further rotation in the counterclockwise direction. In some embodiments, the centrifuge split-housing 404 may include one or more locking elements configured to maintain the halves of the centrifuge split-housing 404 in a locked state, while the locking elements are engaged.

In one embodiment, the centrifuge split-housing 404 may include a pull ring 412 attached to a portion of the upper housing 404B to pivot the upper housing 404B relative to the lower housing 404A about the split-housing pivot axis 406.

The pull ring 412 may provide an aperture, through which a user may insert a finger and apply a pull force to a rotationally unlocked upper housing 404B.

The centrifuge assembly 400 may include a rotor and motor assembly 414 that is controlled and/or powered via electrically interconnected electrical cabling 420. The electrical cabling 420 may include a connector that attaches to a controller, processor, and/or power supply. This electrical cabling 420 may convey power and/or data signals between the rotor and motor assembly 414 and one or more controllers/processors of the apheresis system 200. The rotor and motor assembly 414 may be configured as an electric motor and/or portions of an electric motor that rotate the complete centrifuge assembly 400 relative to the apheresis system 200 (e.g., relative to a portion of the housing 204 and/or base of the apheresis system 200). In other words, the rotor and motor assembly 414 may include one or more components that cause the centrifuge assembly 400 (e.g., both halves of the centrifuge split-housing 404 together) to rotate inside the apheresis system 200.

As described herein, the centrifuge assembly 400 may include one or more features to guide, contain, and/or position elements of the blood component collection set relative to the centrifuge split-housing 404. For instance, in FIG. 4B, the blood component collection loop 520 is shown captured in an operational position in a loop rotational position guide 424 comprising a loop capture arm 416. The loop rotational position guide 424 may include a number of bearings 417, and/or bearing surfaces, arranged to at least partially support the blood component collection loop 520 in an operational position. In the operational position, the blood component collection loop 520 may twist along its length within the support provided by the bearings 417 of the loop rotational position guide 424. For example, the blood component collection loop 520 may be fixedly attached at one end to the fixed loop connection 402 of the apheresis system 200 while the other end of the blood component collection loop 520 may be attached to a filler 460 (e.g., the inner rotating component of the centrifuge assembly 400. As the centrifuge assembly 400 spins during a centrifuge operation, the twisting of the blood component collection loop 520 between the fixed loop connection 402 and the connection at the filler 460 may cause the filler 460 to rotate relative to the centrifuge split-housing 404 of the centrifuge assembly 400. In one embodiment, the low inertia of the filler 460 coupled with the twisting of the blood component collection loop 520 as the centrifuge assembly 400 rotates in the apheresis system 200, may cause the filler 460 to rotate at two times the angular velocity of the centrifuge split-housing 404 in the same direction of spin. In this example, when the centrifuge split-housing 404 spins in a counter-clockwise direction about the centrifuge rotation axis 430 at a first angular velocity, $1\omega$, the filler 460 may spin inside the centrifuge split-housing 404 in the counterclockwise direction at a second angular velocity, $2\omega$ (e.g., substantially two times the first angular velocity, etc.).

The centrifuge assembly 400 may include one or more balancing features, elements, and/or structures disposed about the centrifuge rotation axis 430 of the centrifuge assembly 400. These balancing features may provide an axially balanced centrifuge assembly 400, such that when spun on the centrifuge rotation axis 430, the centrifuge assembly 400 may impart substantially no vibration to the apheresis system 200. In one embodiment, a centrifuge balance weight 418 may be attached to a portion of the centrifuge split-housing 404 (e.g., the lower housing 404A and/or the upper housing 404B, etc.). This centrifuge balance weight 418 may be custom tuned for the centrifuge assembly 400 and as such may be selectively attached and removed from the centrifuge assembly 400. The tuning of the centrifuge balance weight 418 may be calculated and/or empirically derived to produce a completely balanced centrifuge assembly 400, especially when loaded with one or more elements of the blood component collection set.

FIG. 4C shows a rear perspective view of the centrifuge assembly 400 in accordance with embodiments of the present disclosure. A portion of the filler 460 is visible through an aperture in the upper housing 404B. The blood component collection loop 520 is shown in an initial loop loading position 520A, where a first end is interconnected with the filler 460 and a second end is fixedly attached to the fixed loop connection 402 (not shown). The blood component collection loop 520 is shown passing through a loop access clearance 436 in the centrifuge split-housing 404. When the blood component collection loop 520 is loaded in the loop loading position 520A a portion of the blood component collection loop 520 may be partially contained, held, and/or supported by a loop containment bracket 426. The loop containment bracket 426 may include one or more bearings 417 (e.g., roller bearings, ball bearings, needle bearings, etc., and/or assemblies thereof, etc.), or bearing surfaces, arranged to at least partially support the blood component collection loop 520 as it twists relative to the centrifuge assembly 400. In some embodiments, the blood component collection loop 520 may rotate about an axis running along the length of the flexible loop 524 (e.g., in a installed or mounted condition and/or state, etc.) allowing for relative rotational motion of the flexible loop 524 to the loop rotational position guide 424. For instance, the loop does not "twist up" but actually rotates, or rolls, relative to the loop rotational position guide 424 (e.g., support structure) in between one or more bearings 417. This rotation or torsion, without binding or twisting up the flexible loop 524, may be referred to herein as a twist. The twist allows the flexible loop 524 to transmit rotational force to the filler 460 without a substantial reduction in the inside diameter of the lumen of the flexible loop 524. In some cases, there is no reduction in the inside diameter of the lumen of the flexible loop 524.

As described above, when the upper housing 404B is rotated from the rotationally unlocked position shown in FIGS. 4B-4C, to a rotationally locked position, the locking tab 428 of the upper housing 404B may engage with the locking slot 432 in the lower housing 404A. Additionally or alternatively, when moved into the rotationally locked position, the loop containment bracket 426 may rotate, along with the blood component collection loop 520 and the upper housing 404B, to a position in-line with the loop rotational position guide 424 along the loop engaged position 520B. In some embodiments, the loop capture arm 416 may guide the blood component collection loop 520 into the bearings 417 and/or bearing surfaces of the loop rotational position guide 424 as the upper housing 404B and the blood component collection loop 520 rotate into the loop engaged position 520B. Further details regarding the loading of the blood component collection loop 520 are described in conjunction with FIGS. 6A-7B.

Figure 4D:
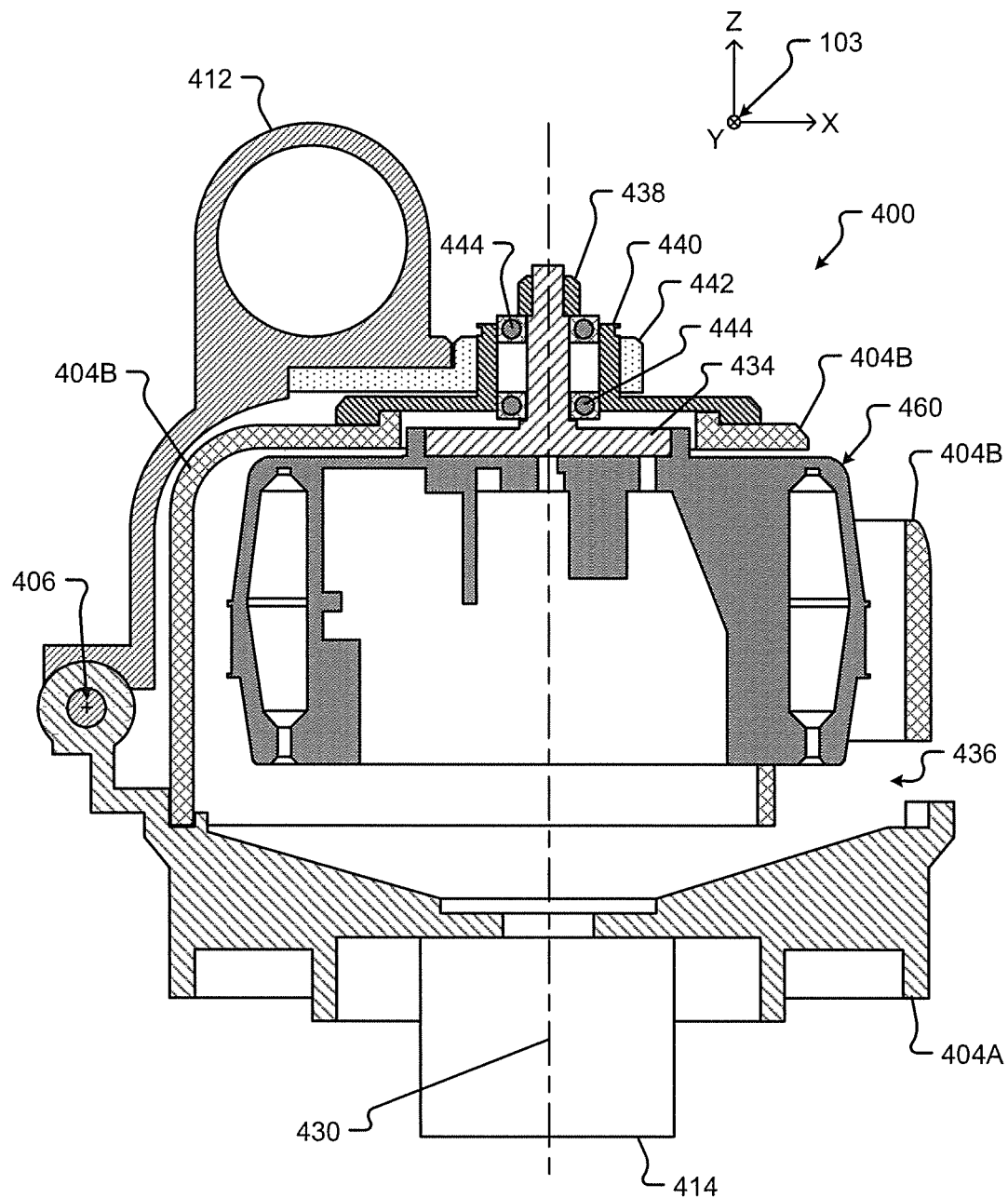
FIG. 4D is a schematic section view of a centrifuge assembly in a closed state in accordance with embodiments of the present disclosure.
Figure 4E:
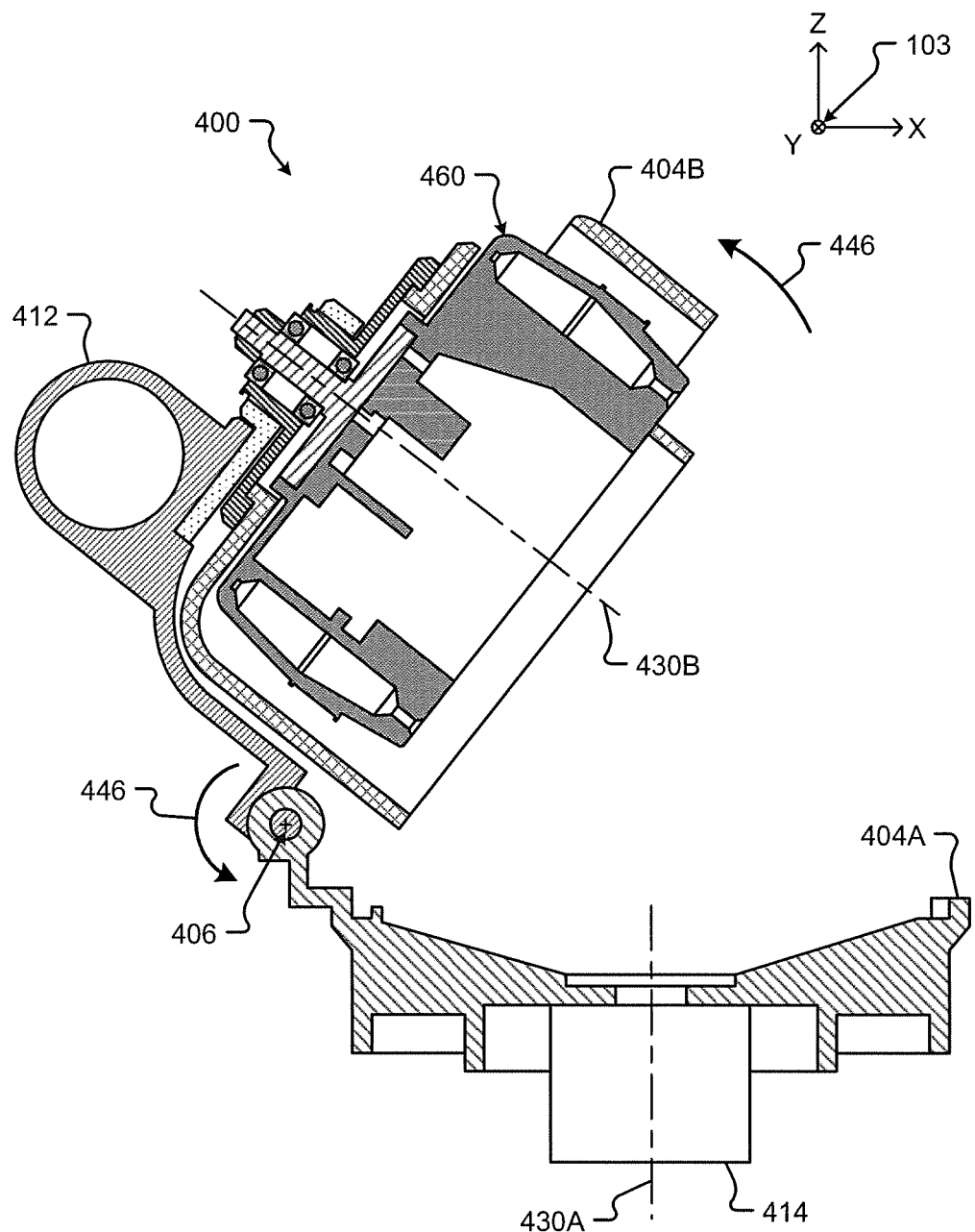
FIG. 4E is a schematic section view of a centrifuge assembly in a partially open state in accordance with embodiments of the present disclosure.
Figure 4F:
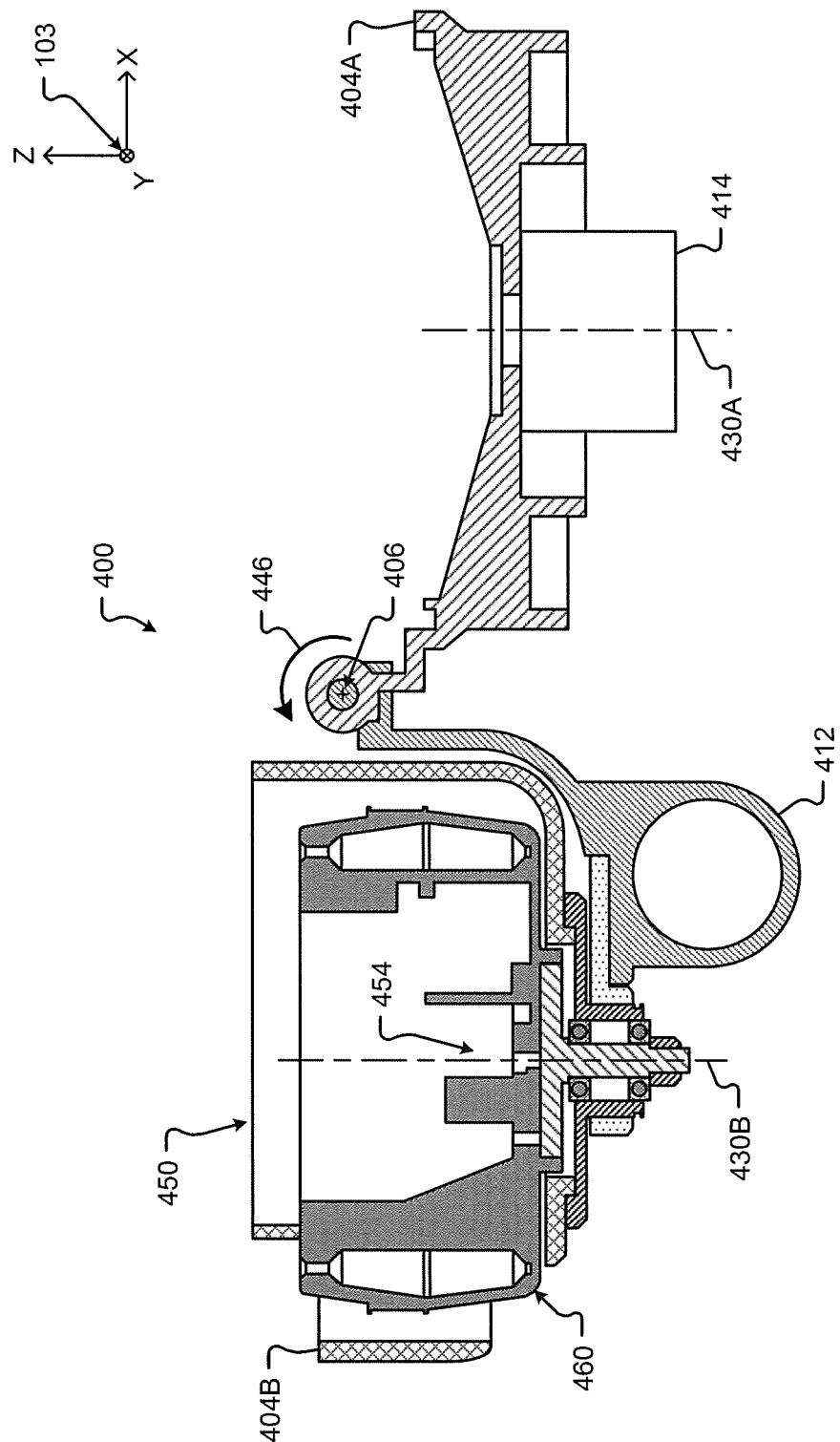
FIG. 4F is a schematic section view of a centrifuge assembly in an open state in accordance with embodiments of the present disclosure.

FIGS. 4D-4F show various schematic section views taken through the center of the centrifuge assembly 400 (e.g., bisecting the centrifuge assembly 400 through the centrifuge rotation axis 430, etc.). As described above, the centrifuge assembly 400 may include a lower housing 404A that is pivotally attached to an upper housing 404B by a split-housing pivot axis 406, or hinge. The upper housing 404B may be attached to an upper housing adapter 440 that is rotationally interconnected to the upper housing bushing block 442 attached to the pull ring 412. In one embodiment, a bearing 417, bushing, or bearing surface may be disposed between the upper housing adapter 440 and the upper housing bushing block 442 allowing the upper housing 404B to rotate along centrifuge rotation axis 430 from a locked position into an unlocked position, and vice versa. The pull ring 412 may be rotationally fixed about centrifuge rotation axis 430 relative to the lower housing 404A. In some embodiments, the upper housing adapter 440 and the upper housing 404B may be formed from an integral structure.

The filler 460 may be fixedly attached to a filler mandrel 434 that is configured to rotate relative to the upper housing 404B about centrifuge rotation axis 430. In one embodiment, the filler mandrel 434 may be formed from a portion of the filler 460. In any event, one or more mandrel support bearings 444 may be disposed between the filler mandrel 434 and the upper housing adapter 440 allowing the filler 460 to rotate inside the centrifuge split-housing 404 and centrifuge assembly 400 about the centrifuge rotation axis 430. In some embodiments, the filler mandrel 434 may be retained in an operative position via at least one retaining nut 438. The filler 460 and filler mandrel 434 may spin together relative to the centrifuge split-housing 404

FIG. 4D shows a schematic section view of the centrifuge assembly 400 in a closed state, e.g., prior to loading the blood component collection loop 520, in accordance with embodiments of the present disclosure. Upon unlocking the upper housing 404B relative to the lower housing 404A, an operator may pull on the pull ring 412 to pivot the entire upper housing 404B and filler 460 about the split-housing pivot axis 406. In one embodiment, the upper housing 404B and the filler 460 may be partially opened by pivoting the components about the split-housing pivot axis 406 in an opening direction 446 as shown in FIG. 4E. As illustrated in FIG. 4E, where the centrifuge assembly 400 is shown in a partially opened state, the upper housing 404B and filler 460 are rotated out of axis from the lower housing rotation axis 430A. In this position, the filler 460 may be allowed to rotate about the filler rotation axis 430B. When the lower housing 404A and upper housing 404B are in a closed state, the lower housing rotation axis 430A and the filler rotation axis 430B align (coincidentally, or substantially coincidentally) to form the centrifuge rotation axis 430.

Continuing to rotate the upper housing 404B and the filler 460 about the Y-axis of the split-housing pivot axis 406 in the opening direction 446 (e.g., by continuing to pull the pull ring 412) may cause the upper housing 404B and the filler 460 to pivot substantially 180 degrees from the closed position shown in FIG. 4D. As shown in FIG. 4F, the centrifuge assembly 400 is in an open, or loading, state. In this position, the upper housing 404B and the filler 460 may be pivoted outside of the interior space of the apheresis system 200. For example, at least a portion of the upper housing 404B and/or the filler 460 may be positioned through an open space of the opened access panel 224. In this position, a loading access area 450 may be provided to the loop connection area 454 of the filler 460. As can be appreciated, orienting the upper housing 404B in the open position provides easy access to the interior of the upper housing 404B and the filler 460. Among other things, this arrangement may provide ample clearance for an operator to attach the blood component collection loop 520 to the filler 460 at the loop connection area 454.

Figure 4G:
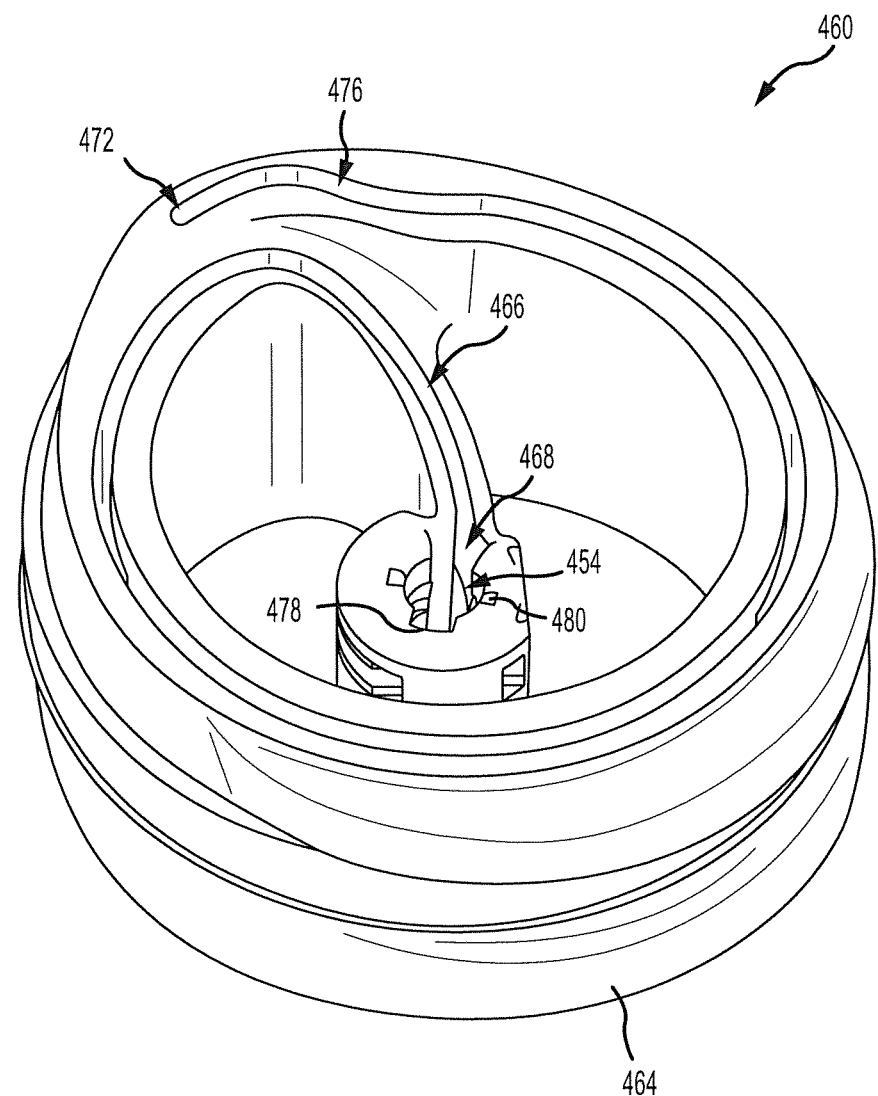
FIG. 4G shows a perspective view of a filler for a centrifuge in accordance with embodiments of the present disclosure.

Referring to FIG. 4G, a perspective view of a filler 460 for the centrifuge assembly 400 is shown in accordance with embodiments of the present disclosure. In some embodi- ments, the filler 460 may be made from a lightweight material such as plastic, carbon fiber, aluminum, etc. In one embodiment, the filler 460 may be three-dimensionally (3D) printed via a 3D printing machine. For instance, the filler 460 may be produced via an additive manufacturing technique or system such as fused deposition modeling (FDM), selective laser sintering (SLS), stereolithography (SLA), and/or other additive manufacturing machines. Among other things, these additive rapid prototyping manufacturing techniques can allow for more complex geometries of the filler 460 that may not be possible through the use of conventional machining or manufacturing processes. In some embodiments, the material of the filler 460 may be selected based on a desired mass of the filler 460, the desired physical strength of the manufactured filler 460, and/or suitable material for use in manufacturing.

The filler 460 may include a loop connection area 454 disposed substantially at the center of the filler 460. The loop connection area 454 may include one or more keying, or positive location, features for a portion of the blood component collection loop 520 to engage. As shown in FIG. 4G, the loop connection area 454 includes a first positive location feature 478 disposed along a portion of the center axis of the filler 460. The first positive location feature 478 may be a keyway, groove, slot, or other feature for engaging with a mating feature disposed on the blood component collection loop 520. In some embodiments, the filler 460 may include a second positive location feature 480 in the loop connection area 454. The location features 478, 480 may prevent rotation of the blood component collection loop 520 at the loop connection area 454 and/or prevent the blood component collection loop 520 from disengaging from the loop connection area 454 of the filler 460.

Figure 4H:
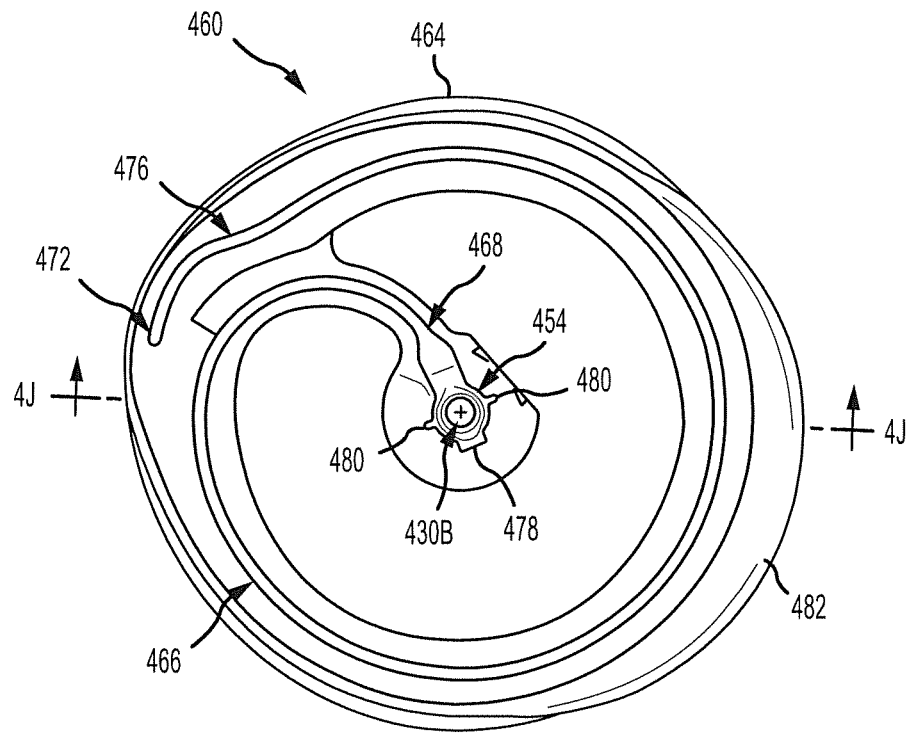
FIG. 4H is a plan view of a filler for a centrifuge in accordance with embodiments of the present disclosure.
Figure 4I:
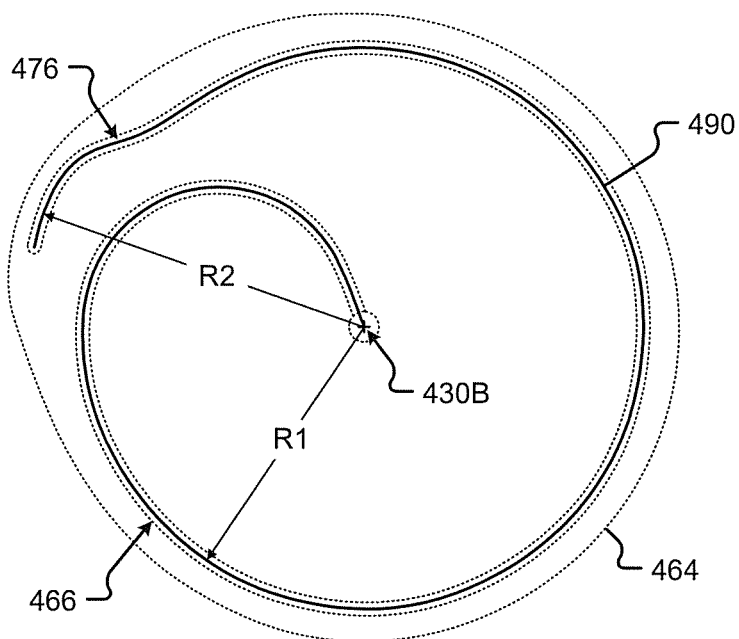
FIG. 4I is a schematic plan view of a substantially spiral-shaped receiving channel for a filler in accordance with embodiments of the present disclosure.

In some embodiments, the filler 460 may include a collection insert channel 466 configured to receive, and at least partially contain, a blood component collection bladder of the blood component collection set and, more specifically, the blood component collection loop 520. The collection insert channel 466 may be configured as a groove, slot, extending outwardly, in a substantially spiral fashion, from a center of the filler 460. In some embodiments, the collection insert channel 466 may follow a substantially spiral shaped path that may include a first spiral path portion extending outwardly from the center of the filler 460 to a substantially constant radius (e.g., about the center of the filler 460) along a length of the collection insert channel 466 periphery. In any event, the path may be referred to herein as a spiral path or a substantially spiral path. The collection insert channel 466 may start at a channel entrance 468 adjacent to the center of the filler body 464 and terminate at a channel end 472 adjacent at a point furthest from the center of the filler body 464. As shown in FIGS. 4G-4I, the collection insert channel 466 may extend along a substantially spiral path 490 running from a point adjacent to the filler rotation axis 430B to the channel end 472. The substantially spiral path 490 may include a channel path jog 476 at a point near, or adjacent to, the channel end 472. This channel path jog 476 may extend the distance of the collection insert channel 466 from the center of the filler body 464 thereby increasing the centripetal and centrifugal forces at the channel end 472 of the collection insert channel 466. In one embodiment, this channel path jog 476 may correspond to a critical inlet and exit port at a radial maximum within a blood component collection bladder 536 that is inserted or disposed, at least partially, within the collection insert channel 466 of the filler 460. In some embodiments, the filler 460 may include one or more filler balance protrusions 482 disposed on, in, or about a portion of the filler body 464. These filler balance protrusions 482 may provide an axially balanced (e.g., about the filler rotation axis 430B) filler 460, especially when the collection insert channel 466 includes a blood component collection bladder and fluid (e.g., blood, blood components, etc.).

FIG. 4I is a schematic plan view of a substantially spiral-shaped receiving channel, or collection insert channel 466, for a filler 460 in accordance with embodiments of the present disclosure. The schematic plan view shows a first distance, R1, of the collection insert channel 466 from a center of the filler body 464 (e.g., adjacent to the filler rotation axis 430B, etc.) at a first point along the substantially spiral path 490 and a second distance, R2, of the collection insert channel 466 from the center of the filler body 464 past a point adjacent to the channel path jog 476. As illustrated in FIG. 4I, the second distance, R2, is further from the center of the filler body 464 than the first distance, R1. This increase in distance may provide higher centripetal and centrifugal forces in the channel at a point near, or at, the channel end 472 than at any other point along the substantially spiral path 490. In some embodiments, the end of the blood collection bladder may substantially coincide with the channel end 472, providing the greatest blood separation forces at the end of the bladder.

Figure 4J:
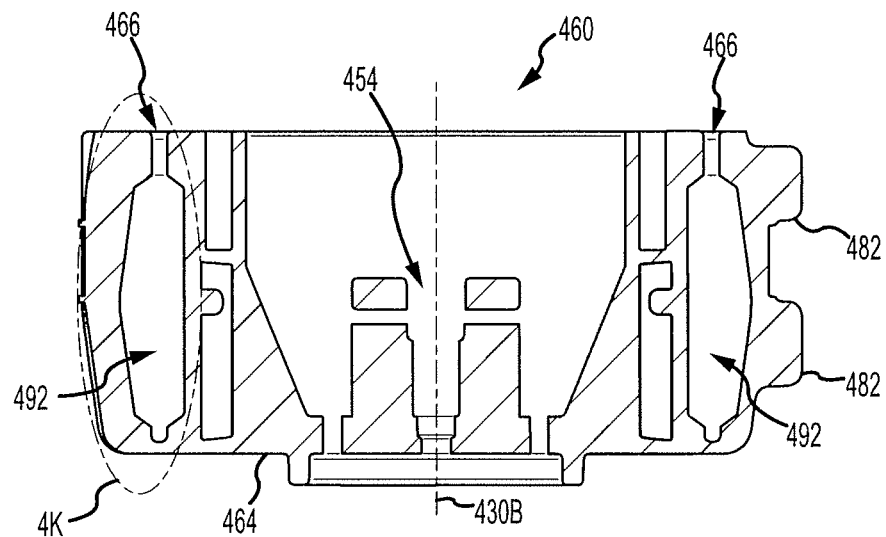
FIG. 4J is an elevation section view taken through line 4J of FIG. 4H.
Figure 4K:
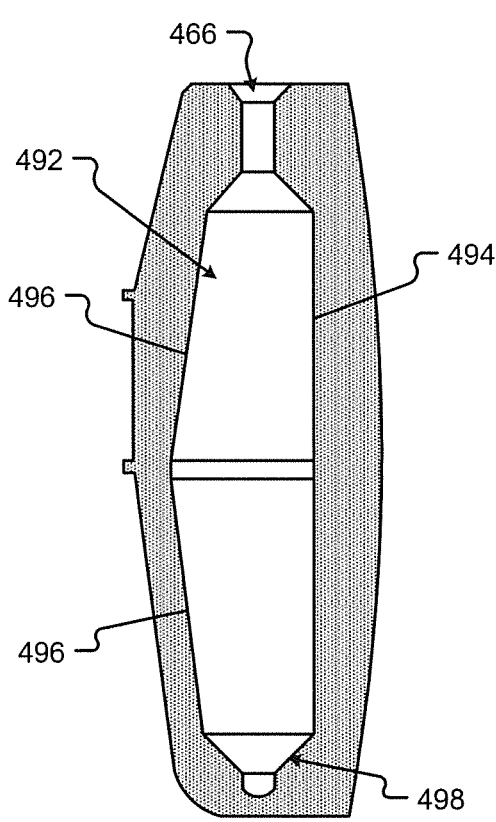
FIG. 4K is a detail section view of a portion of a channel in the filler in accordance with embodiments of the present disclosure.
Figure 4L:
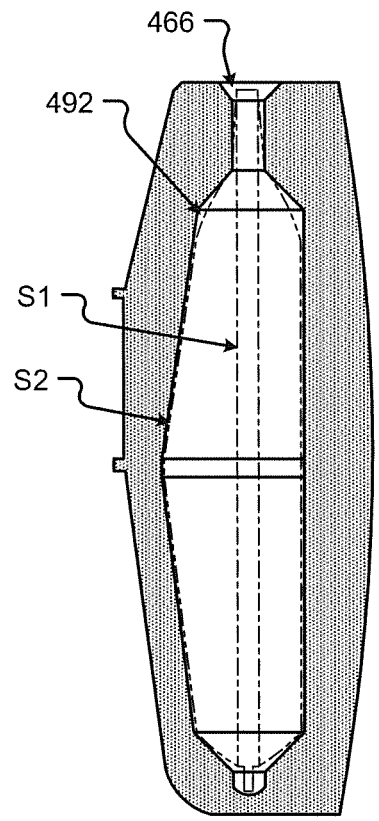
FIG. 4L shows different states of fluid collection bladders disposed inside the channel in the filler of FIG. 4K.

FIGS. 4J-4L show various elevation section of the filler 460 and, more specifically of, the collection insert channel 466 and filler insert chamber 492 disposed inside the filler body 464. In some embodiments, the collection insert channel 466 may include a cross-section, or shape, that substantially follows the substantially spiral path 490 in the filler body 464. The collection insert channel 466 may include an insert groove configured to receive a substantially flat, or unfilled, blood component collection bladder. The blood component collection bladder may be inserted into the collection insert channel 466 and a filler insert chamber 492 formed in the filler body 464 along the substantially spiral path 490. The filler insert chamber 492 may be defined by one or more sidewalls 494, 496 forming a cavity that follows the substantially spiral path 490. As shown in FIG. 4K, the filler insert chamber 492 includes an inner chamber wall 494 separated a distance from at least one outer chamber wall 496. The filler insert chamber 492 may be formed in the filler 460 by 3D printing the filler 460 and/or by some other metal or plastic forming operation, or operations (e.g., casting, molding, forming, etc.). In some embodiments, the filler insert chamber 492 may include one or more insert guide features 498. These insert guide features 498 may be configured to guide, locate, and/or seat a blood component collection bladder inside the filler insert chamber 492 of the filler 460. Although shown as a chamfered, or lead-in, feature of the filler insert chamber 492, the insert guide feature 498 may include one or more radius, chamfer, slope, taper, draft angle, receptacle, groove, and/or other shaped material configured to direct and/or orient a portion of an inserted blood component collection bladder.

FIG. 4L shows different states of fluid collection bladders (e.g., blood component collection bladders, etc.) disposed inside the collection insert channel 466 and the filler insert chamber 492 of the filler 460. As described above, a blood component collection bladder may be inserted into the collection insert channel 466 in a substantially flat, or unfilled, state, S1. In the substantially flat state, S1, the blood component collection bladder may be sized to enter the upper opening of the collection insert channel 466 and be maintained in a pre-fill condition inside the filler insert chamber 492. When the filler 460 begins to spin and separate blood components from blood provided by a donor 102, the blood component collection bladder may expand from the substantially flat first state, S1, to an expanded, or filled, state, S2. In some embodiments, the blood component collection bladder may expand with blood and/or blood components until the walls of the blood component collection bladder contact the walls 494, 496 of the filler insert chamber 492. In one embodiment, the shape of the filler insert chamber 492 may be designed to optimize the amount of fluid (e.g., maximize the volume of fluid while minimizing the amount of material for the filler 460) capable of being collected and/or separated in the filler insert chamber 492.

Figure 5A:
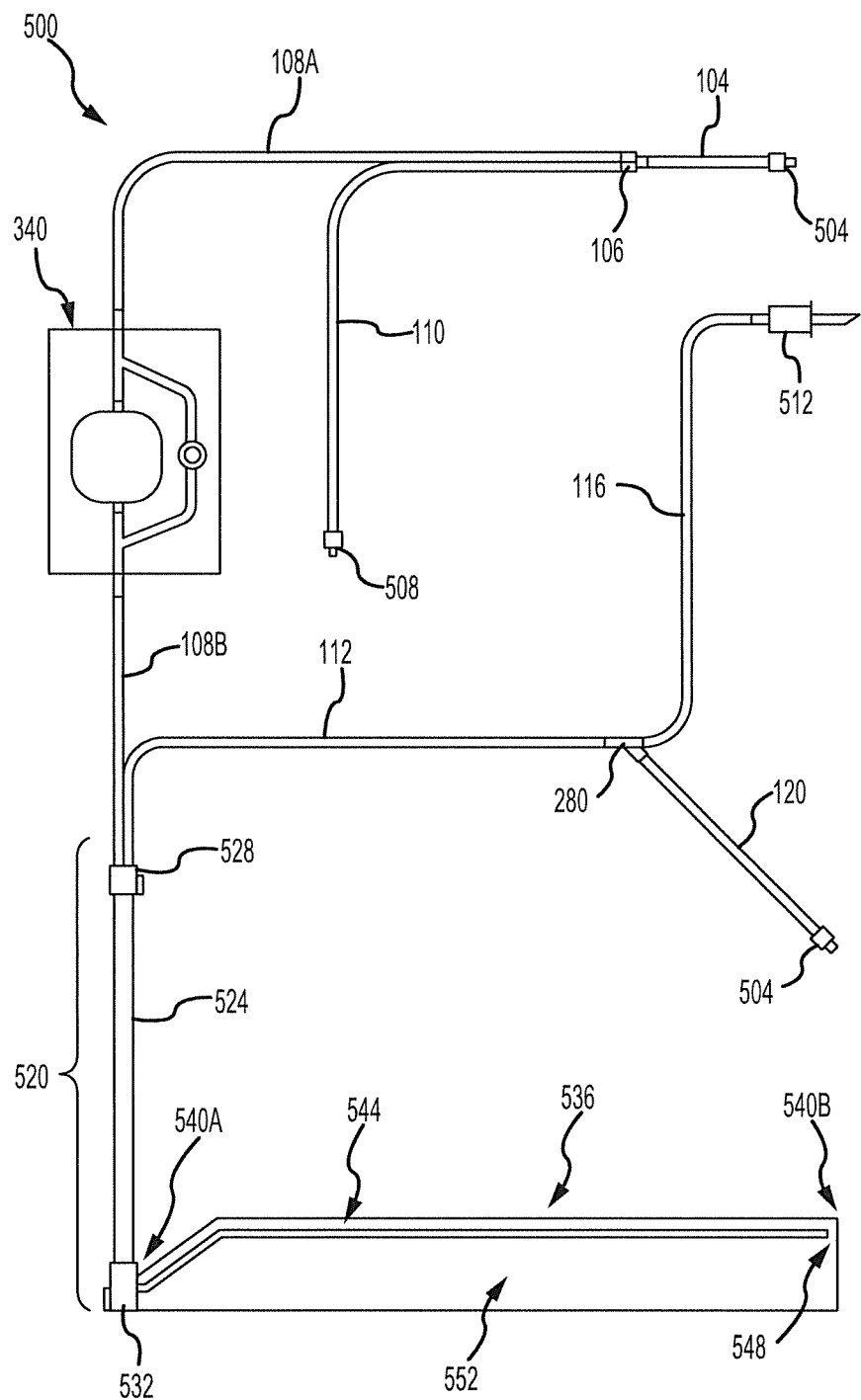
FIG. 5A shows a schematic view of a fluid component collection set in accordance with embodiments of the present disclosure.

FIG. 5A shows a schematic view of a blood component collection set 500 in accordance with embodiments of the present disclosure. The blood component collection set 500 may include the tubing (e.g., one or more of the donor feed tubing 104, cassette inlet tubing 108A, loop inlet tubing 108B, anticoagulant tubing 110, loop exit tubing 112, saline tubing 116, plasma tubing 120, etc.), the connectors (e.g., one or more of the tubing connector 106, saline and plasma tubing y-connector 280, tubing fittings 504, tubing fitting 508, bag spike fitting 512, etc.), soft cassette 340, and the blood component collection loop 520.

The tubing may include any tubing having a central lumen configured to convey fluid therethrough. The tubing may be made from polyvinyl chloride (PVC), plasticized-PVC, polyethylene, ethylene with vinyl acetate (EVA), rubber, polymers, copolymers, and/or combinations thereof. The connectors may be configured to fluidly interconnect with the tubing (e.g., at one or more ends of the tubing, etc.). The connectors may insert into the central lumen of the tubing and/or attach to an outside of the tubing. In some embodiments, the connectors may be configured with various fittings (e.g., Luer fitting, twist-to-connect, and/or other small-bore couplings, etc.) to provide universal and/or reliable interconnections to one or more other fittings, connectors, tubing, needles, and/or medical accessory. In one embodiment, the bag spike fitting 512 may be configured to insert into a receiving bag (e.g., saline bag 118, etc.).

The blood component collection loop 520 may comprise a flexible loop 524 disposed between a system static loop connector 528 and a filler loop connector 532. The flexible loop 524 may be configured as a hollow flexible tube configured to receive and/or contain at least a portion of the loop inlet tubing 108B and the loop exit tubing 112. In some embodiments, the flexible loop 524 may be made from a thermoplastic elastomer having enhanced flexibility for transmitting twist from one end of the flexible loop 524 to the other. These types of elastomers may provide the flexibility of rubber while maintaining the strength and torque characteristics of plastics. Examples of the thermoplastic elastomer may include, but are in no way limited to, copolyester, DuPont™ Hytrel® thermoplastic elastomers, Eastman Neostar™ elastomers, Celanese Riteflex® elastomers, TOYOBO PELPRENE®, and/or other brand elastomers offering high flexibility and strength characteristics.

In some embodiments, the blood component collection loop 520 may include a blood component collection bladder 536 having a bladder loop end 540A and a bladder free end 540B. The blood component collection bladder 536 may include a first collection flow chamber 544 connected to the flexible loop 524 at the filler loop connector 532. In particular, fluid may flow between the loop inlet tubing 108B and the first collection flow chamber 544 via the flexible loop 524 and the connectors 528, 532, and/or vice versa. Fluid flowing in a direction from the bladder loop end 540A to the bladder free end 540B along the first collection flow chamber 544 may reach a flow chamber transition 548 and enter the second collection flow chamber 552. In one embodiment, the second collection flow chamber 552 is interconnected to the flexible loop 524 at the filler loop connector 532. In particular, fluid may flow between the loop exit tubing 112 and the second collection flow chamber 552 via the flexible loop 524 and the connectors 528, 532, and/or vice versa.

Figure 5B:
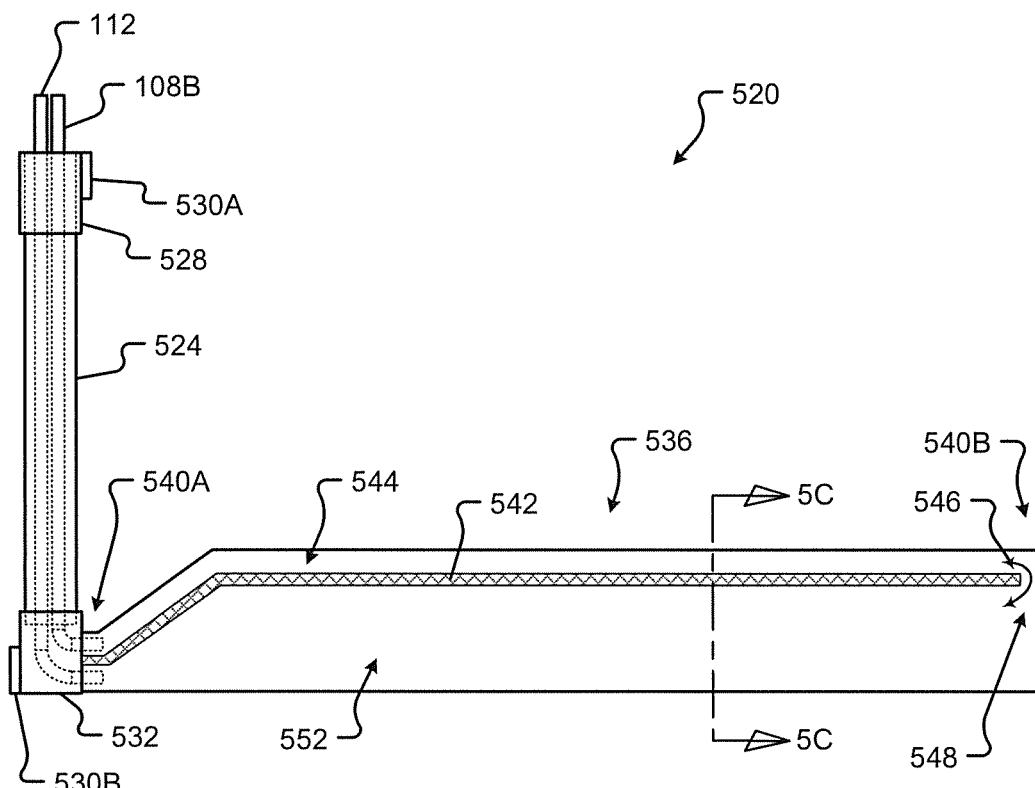
FIG. 5B shows an elevation view of a fluid component collection loop in accordance with embodiments of the present disclosure.

Details of the blood component collection loop 520 are illustrated in conjunction with the elevation view of FIG. 5B. The blood component collection loop 520 may include a flexible loop 524 configured as a tube including a first pathway for the loop inlet tubing 108B and a second pathway for the loop exit tubing 112. In some embodiments, the loop inlet tubing 108B may pass through the flexible loop 524 and interconnect with the first collection flow chamber 544 at the bladder loop end 540A via the filler loop connector 532. Additionally or alternatively, the loop exit tubing 112 may pass through the flexible loop 524 and interconnect with the second collection flow chamber 552 at the bladder loop end 540A via the filler loop connector 532. The first pathway is separate from the second pathway. This configuration allows blood to enter the flexible loop 524 and the blood component collection bladder 536 via the first collection flow chamber 544 and separate into one or more blood components, which can then be conveyed along the second collection flow chamber 552 to the loop exit tubing 112 in the flexible loop 524.

The first collection flow chamber 544 may be separated from the second collection flow chamber 552 via a flow chamber separator 542. The flow chamber separator 542 may be a heat sealed portion of the blood component collection bladder 536. For example, the blood component collection bladder 536 may be made from layers of material overlapping one another along a length of the blood component collection bladder 536. The layers of material may be shaped (e.g., cut or otherwise shaped, etc.) and heat sealed along one or more edges forming a fluid container. The flow chamber separator 542 may be formed in the fluid container by heat sealing one layer of material to the other layer of material along a path as substantially illustrated. The flow chamber separator 542 does not extend the complete length of the blood component collection bladder 536 providing a flow chamber transition 548 for fluid (e.g., blood, blood components, etc.) to pass from the first collection flow chamber 544 to the second collection flow chamber 552, and/or vice versa. In one embodiment, fluid (e.g., blood and/or blood components, etc.) in the blood component collection bladder 536 contained in the filler insert chamber 492 of the filler 460 may travel in a direction toward the bladder free end 540B along the first collection flow chamber 544 around an end of the flow chamber separator 542 (e.g., following blood component movement direction 546) and into the second collection flow chamber 552. In this example, blood components (e.g., plasma, etc.) may be forced back along the substantially spiral path 490 toward the center of the filler body 464 along the second collection flow chamber 552 and through the loop exit tubing 112 (e.g., to a plasma collection bottle 122).

The blood component collection bladder 536 may be made from polyvinyl chloride (PVC), plasticized-PVC, polyethylene, ethylene with vinyl acetate (EVA), thermoplastics, thermoplastic elastomer, polymers, copolymers, and/or combinations thereof. In some embodiments, the blood component collection bladder 536 may be formed, heat sealed from multiple layers of material, formed from a single layer of material folded onto itself, and/or combinations thereof.

In some embodiments, the blood component collection loop 520 may include a number of positive location, or key, features 530A, 530B configured to positively locate portions of the blood component collection loop 520 relative to the apheresis system 200 and/or the filler 460. For example, the blood component collection loop 520 includes a first connector location feature 530A on the system static loop connector 528 and a second connector location feature 530B on the filler loop connector 532. The features 530A, 530B may be configured as a key, a tab, and/or other protrusion of material extending from the connector 528, 532. In some embodiments, the second connector location feature 530B may include features that interconnect, or mate, with the first positive location feature 478 and/or the second positive location feature 480 of the loop connection area 454 in the filler 460. Similar, if not identical, positive location features may be associated with, or included in, the fixed loop connection 402 of the apheresis system 200.

Figure 5C:
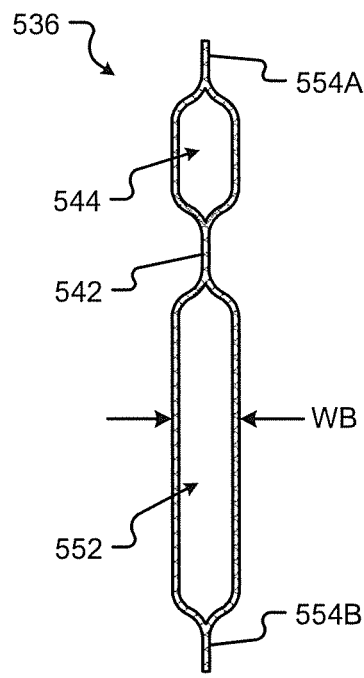
FIG. 5C shows a cross-section of a bladder of a fluid component collection loop in accordance with one embodiment of the present disclosure.
Figure 5D:
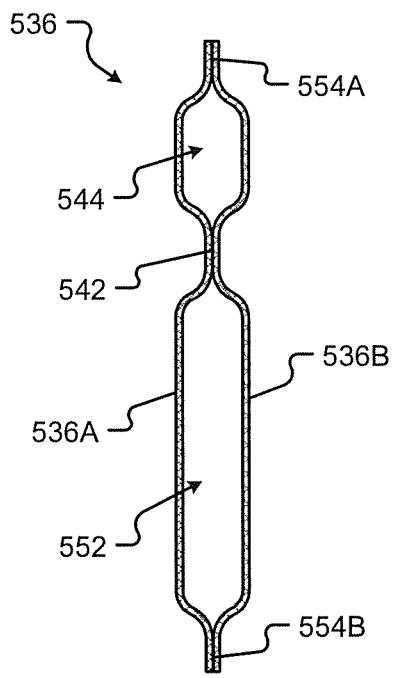
FIG. 5D shows a cross-section of a bladder of a fluid component collection loop in accordance with another embodiment of the present disclosure.

FIGS. 5C and 5D show cross-sections of the blood component collection bladder 536 of the blood component collection loop 520 in accordance with embodiments of the present disclosure. For instance, the cross-sections show the first collection flow chamber 544 separate from the second collection flow chamber 552 along a length of the blood component collection bladder 536. In some embodiments, the separation may be provided by a flow chamber separator 542 disposed between the first collection flow chamber 544 and the second collection flow chamber 552. The flow chamber separator 542 may correspond to a sealed region of the blood component collection bladder 536. The flow chamber separator 542 may be formed as a heat-sealed region of material, for instance, joining a bladder first side material 536A to a bladder second side material 536B. In some cases, the bladder first side material 536A and the bladder second side material 536B may be a single piece of material folded at an edge (e.g., adjacent to one of the upper bladder seal 554A area or the lower bladder seal 554B area).

The cross-section shown in FIG. 5D may correspond to a blood component collection bladder 536 prior to sealing, and the cross-section shown in FIG. 5C may correspond to the blood component collection bladder 536 after the upper bladder seal 554A, lower bladder seal 554B, and/or the flow chamber separator 542 are formed or sealed (e.g., welding the bladder first side material 536A to the bladder second side material 536B, etc.). Once formed, the width of the bladder, WB, may correspond to the width of the first collection flow chamber 544 and/or the second collection flow chamber 552 in an unexpanded state, S1 (see, e.g., FIG. 4L). During operation, as fluid fills at least a portion of the blood component collection bladder 536, the width of the bladder, WB, may increase in dimension from the dimension shown in FIG. 5C. For instance, the width of the bladder, WB, may increase substantially to the size of the filler insert chamber 492 of the filler 460. In some embodiments, the welds (e.g., RF, ultrasonic, etc.) made while manufacturing the blood component collection bladder 536 may be supported in the filler 460. In one embodiment, the top of the filler 460 supports the top two welds and the bottom of the filler 460 supports a final weld.

FIGS. 5E-5H show various perspective views of the blood component collection loop 520 in a flexed state (e.g., FIGS. 5E-5F) as well as views of the flexed blood component collection bladder 536 of the blood component collection loop 520 being inserting into a filler 460 (e.g., FIGS.

Figure 5E:
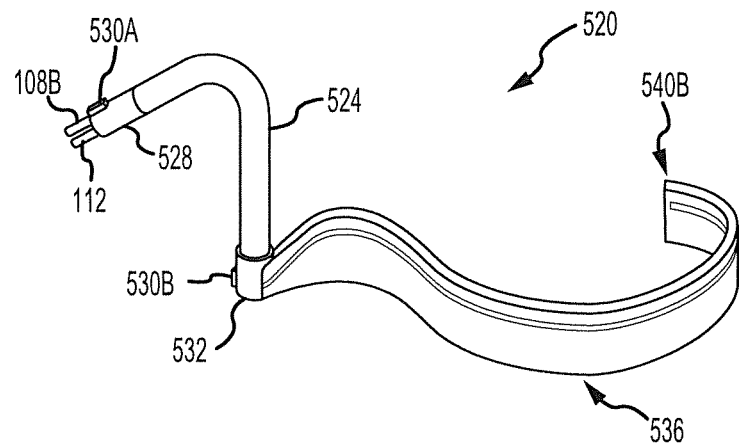
FIG. 5E shows a perspective view of a fluid component collection loop in a flexed state in accordance with embodiments of the present disclosure.

5G-5H). The various components of the blood component collection loop 520 may be flexible and/or capable of being formed or shaped by the application of force. In some embodiments, this flexibility may be elastic such that forming the various parts of the blood component collection loop 520 does not permanently deform the components. FIG. 5E shows the blood component collection loop 520 in a flexed state in accordance with embodiments of the present disclosure. For example, the flexible loop 524 is shown elastically bent along its length and the blood component collection bladder 536 is shown following a number of bends or curves along its length. The flexible loop 524 may still convey fluids provided via the loop inlet tubing 108B to the first collection flow chamber 544 of the blood component collection bladder 536, and vice versa, while the components are in a flexed state. Additionally or alternatively, the flexible loop 524 may convey fluids from the second collection flow chamber 552 of the blood component collection bladder 536 to the loop exit tubing 112, and vice versa, while the components are in the flexed state.

Figure 5F:
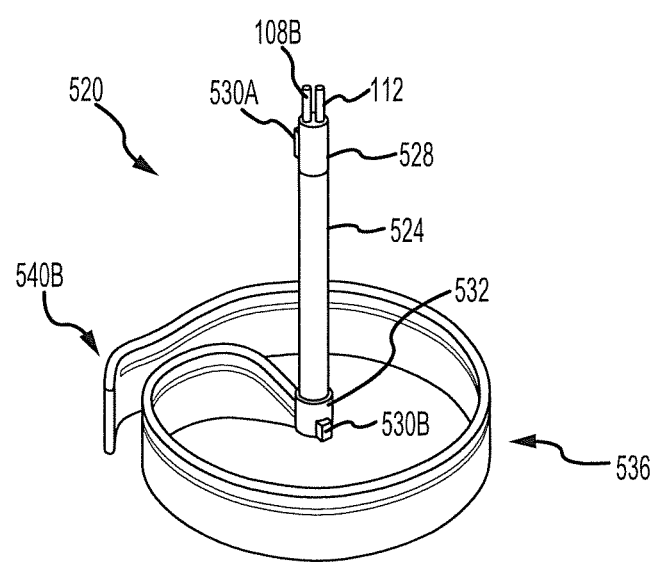
FIG. 5F shows a perspective view of a fluid component collection loop in a loading state in accordance with embodiments of the present disclosure.

In some embodiments, the blood component collection loop 520 may be pre-formed, as shown in the perspective view of FIG. 5F, to fit inside the collection insert channel 466 of a filler 460. This pre-forming may include twisting the blood component collection bladder 536 of the blood component collection loop 520 to match the substantially spiral path 490 of the collection insert channel 466. Once pre-formed, the features of the blood component collection loop 520 may be aligned with one or more features of the filler 460, as shown in FIG. 5G. In one embodiment, the filler loop connector 532 of the blood component collection loop 520 may be aligned with the loop connection area 454 of the filler 460 such that the second connector location feature 530B is aligned to engage with the first positive location feature 478. Additionally or alternatively, the blood component collection bladder 536 may be shaped, or formed (e.g., by hand, etc.), to match the substantially spiral path 490 of the collection insert channel 466 in the filler 460. In some cases, this shaping or forming may include aligning the bladder free end 540B of the blood component collection bladder 536 with the channel end 472 of the collection insert channel 466 in the filler 460. When the components are generally aligned with one another, the blood component collection loop 520 may be moved in a direction toward the collection insert channel 466 and the loop connection area 454 (as shown in FIG. 5G).

In some embodiments, when the filler loop connector 532 is moved toward and into the loop connection area 454 of the filler 460, the first positive location feature 478 may interconnect and/or retain the second connector location feature 530B of the filler loop connector 532 of the blood component collection loop 520. This interconnection may prevent the filler loop connector 532 from rotating relative to the filler 460. In some cases, the interconnection may maintain the filler loop connector 532 of the blood component collection loop 520 inside the loop connection area 454 of the filler 460. FIG. 5H shows a perspective view of the blood component collection loop 520 loaded in the filler 460 in accordance with embodiments of the present disclosure.

Figure 6A:
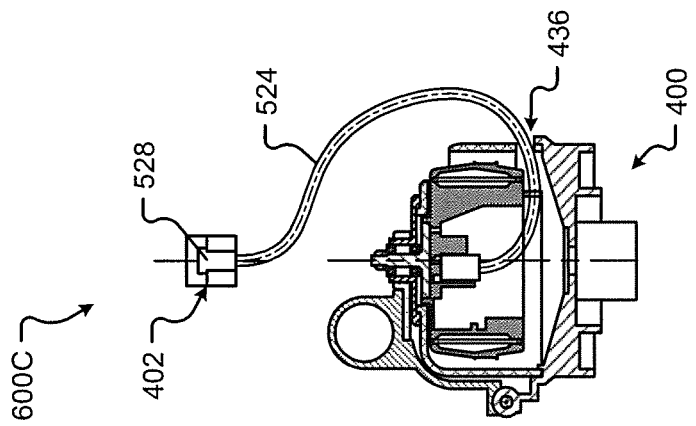
FIG. 6A shows a schematic section view of a centrifuge assembly in a first loop-loading state in accordance with embodiments of the present disclosure.
Figure 6B:
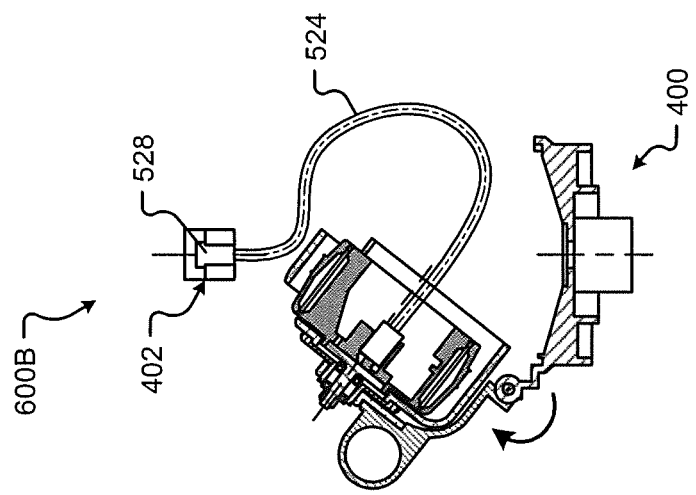
FIG. 6B shows a schematic section view of a centrifuge assembly in a second loop-loading state in accordance with embodiments of the present disclosure.
Figure 6C:
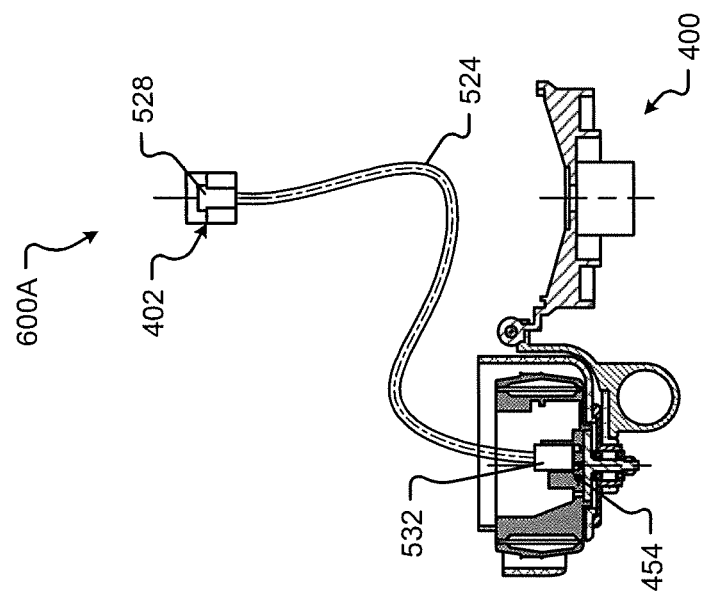
FIG. 6C shows a schematic section view of a centrifuge assembly in a third loop-loading state in accordance with embodiments of the present disclosure.

FIGS. 6A-6C show schematic section views of a centrifuge assembly 400 in various loop-loading states in accordance with embodiments of the present disclosure. The centrifuge assembly 400 shown in FIGS. 6A-6C may correspond to the centrifuge assembly 400 described above and especially in conjunction with FIGS. 4D-4F. In particular, FIG. 6A shows a schematic section view of a first loop-loading state, FIG. 6B shows a schematic section view of a second loop-loading state, and FIG. 6C shows a schematic section view of a second loop-loading state for the centrifuge assembly 400.

In FIG. 6A, the centrifuge assembly 400 is shown in an open, loop-loading, position where the upper housing 404B has been pivoted 180 degrees from a closed, or operational, position. This open position may correspond to the position of the centrifuge assembly 400 shown in FIG. 4F. However, in FIG. 6A, a blood component collection loop 520 has been inserted into the filler 460 and the filler loop connector 532 is interconnected to the loop connection area 454 of the filler body 464. The other end of the blood component collection loop 520 is connected to the fixed loop connection 402 via the system static loop connector 528. In this first loop-loading state, the flexible loop 524 is fixed from rotating at the fixed loop connection 402 but rotates, in unison, with the filler 460 at the loop connection area 454.

In FIG. 6B, the centrifuge assembly 400 is shown in a partially closed position where the upper housing 404B is being moved from the open position to a closed, or operational, position. As the upper housing 404B pivots, the flexible loop 524 may move to a resting position relative to the centrifuge assembly 400. Although the flexible loop 524 is rotationally fixed at the fixed loop connection 402, the filler 460 may be free to rotate about the filler rotation axis 430B (e.g., restricted only by the rotationally fixed flexible loop 524).

In FIG. 6C, the centrifuge assembly 400 is shown in a closed, or operational, position where the upper housing 404B may be locked to the lower housing 404A (such that the lower housing 404A and the upper housing 404B may rotate in unison about the centrifuge rotation axis 430). In this position, the flexible loop 524 may pass from the loop connection area 454 of the filler 460 through the loop access clearance 436 of the centrifuge split-housing 404 to the fixed loop connection 402. In some embodiments, the flexible loop 524 may be free to move within the loop access clearance 436 with or without contacting one or more portions of the centrifuge split-housing 404. In this position, as the centrifuge assembly 400 rotates about the centrifuge rotation axis 430, the flexible loop 524 rotationally fixed at the fixed loop connection 402 may twist along the length of the flexible loop 524 thereby rotating the filler 460 inside the centrifuge assembly 400 (e.g., along the centrifuge rotation axis 430). As provided above, the rotation of the filler 460 relative to the centrifuge assembly 400 may be at a 2:1 ratio. For instance, as the centrifuge assembly 400 rotates one revolution, the rotationally fixed flexible loop 524 (e.g., fixed at the fixed loop connection 402) twists at the loop connection area 454 (e.g., trying to unravel from being twisted by the rotation of the centrifuge assembly 400, etc.) thereby rotating the filler 460 in the same rotational direction as the centrifuge assembly 400 but at substantially two revolutions. This rotation of the filler 460, by the twisting of the flexible loop 524 along its length, requires no gearing between the centrifuge assembly 400 and the filler 460.

Figure 7B:
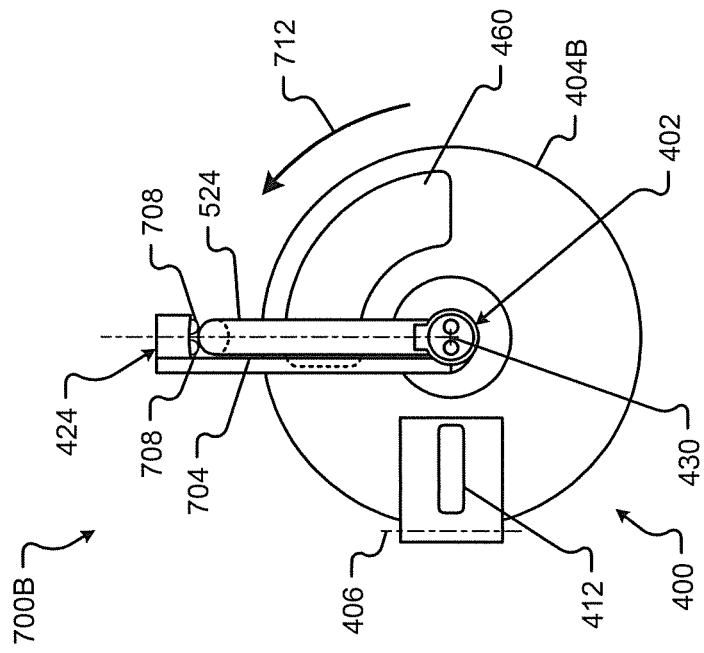
FIG. 7B shows a schematic plan view of a centrifuge assembly in an operational state in accordance with embodiments of the present disclosure.
Figure 7A:
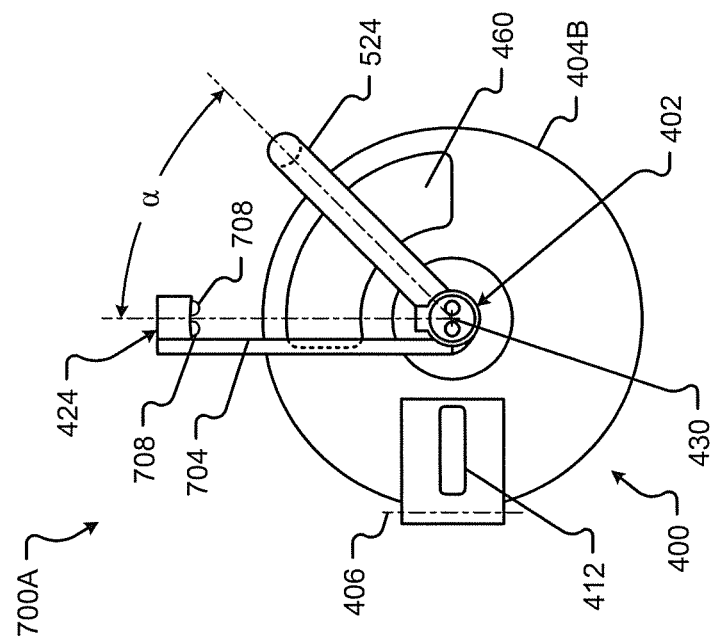
FIG. 7A shows a schematic plan view of a centrifuge assembly in a loop-loaded state in accordance with embodiments of the present disclosure.

FIGS. 7A-7B show schematic plan views of the centrifuge assembly 400 automatically loading a loop into an operational position (e.g., blood separation) for centrifuging. The centrifuge assembly 400 shown in FIGS. 7A-7B may correspond to the centrifuge assembly 400 as previously discussed and/or as described in conjunction with FIGS. 4A-4F and FIGS. 6A-6C. Once the blood component collection loop 520 has been loaded into the centrifuge assembly 400, as illustrated in FIG. 6C, the flexible loop 524 may be automatically loaded into a loop engaged position 520B as shown in FIGS. 7A-7B.

In one embodiment, when the upper housing 404B is locked to the lower housing 404A, the flexible loop 524 may run from the loop connection area 454 of the filler 460 to the fixed loop connection 402 of the apheresis system 200. Although the flexible loop 524 may be rotationally fixed to the fixed loop connection 402 at the system static loop connector 528, the flexible loop 524 passing through the loop access clearance 436 in the centrifuge split-housing 404 may not initially be held, or at least partially captured, by the loop rotational position guide 424 and/or other features of the centrifuge assembly 400. This state of the flexible loop 524 relative to the loop rotational position guide 424, or loop arm, may correspond to an uncaptured loop state 700A. In other words, the flexible loop 524 may be oriented at some angle, a, relative to the loop rotational position guide 424, loop position stop plate 704, and/or one or more loop twist support bearings 708, or bearing sets. In some embodiments, the loop twist support bearing 708 may correspond to the bearings 417 described in conjunction with FIGS. 4B-4C. A loop containment area, or channel, may be formed by the loop position stop plate 704, and/or one or more loop twist support bearings 708 disposed along a length of the upper housing 404B. In some embodiments, this orientation may be engineered to allow access and/or ease of loading during the loop-loading described in conjunction with FIGS. 6A-6C.

As the centrifuge assembly 400 is rotated in a loop and filler rotation direction 712 about centrifuge rotation axis 430, the flexible loop 524 may move from the uncaptured loop state 700A to the captured loop state 700B shown in FIG. 7B. This rotation may be caused by an operator rotating the centrifuge assembly 400 and/or the filler 460 in the loop and filler rotation direction 712 and/or by the rotor and motor assembly 414 causing the centrifuge assembly 400 to rotate about the centrifuge rotation axis 430. In some embodiments, as the flexible loop 524 rotates in the loop and filler rotation direction 712, an outer portion of the flexible loop 524 may contact a loop position stop plate 704, or other rotational stop surface, of the loop rotational position guide 424.

While the flexible loop 524 is held, or at least partially contained, in the loop rotational position guide 424, a portion of the flexible loop 524 may move within one or more of the loop twist support bearings 708. As described above, the flexible loop 524 may be rotationally fixed to the fixed loop connection 402 via the first connector location feature 530A of the system static loop connector 528 associated with the blood component collection loop 520. This rotationally fixed connection prevents the flexible loop 524 from rotating relative to the apheresis system 200 at the fixed loop connection 402. The other end of the flexible loop 524 may be interconnected at the loop connection area 454 of the filler 460 where the end can move with the filler 460 and/or centrifuge assembly 400. As the centrifuge assembly 400 continues to rotate in the loop and filler rotation direction 712, the forces from the flexible loop 524 attempting to unravel, or keep from binding, rotate the filler 460 and the end of the flexible loop 524 attached thereto.

In any event, once the fluid separation methods described herein are completed, the centrifuge assembly 400 may be stopped from rotating and the centrifuge split-housing 404 can be opened to remove the disposable elements of the blood component collection set 500 from the centrifuge assembly 400. In some cases, the flexible loop 524 may be moved from the captured loop state 700B shown in FIG. 7B to the uncaptured loop state 700A shown in FIG. 7A by rotating the centrifuge assembly 400 and/or the filler 460 in a direction opposite the loop and filler rotation direction 712.

Figure 8:
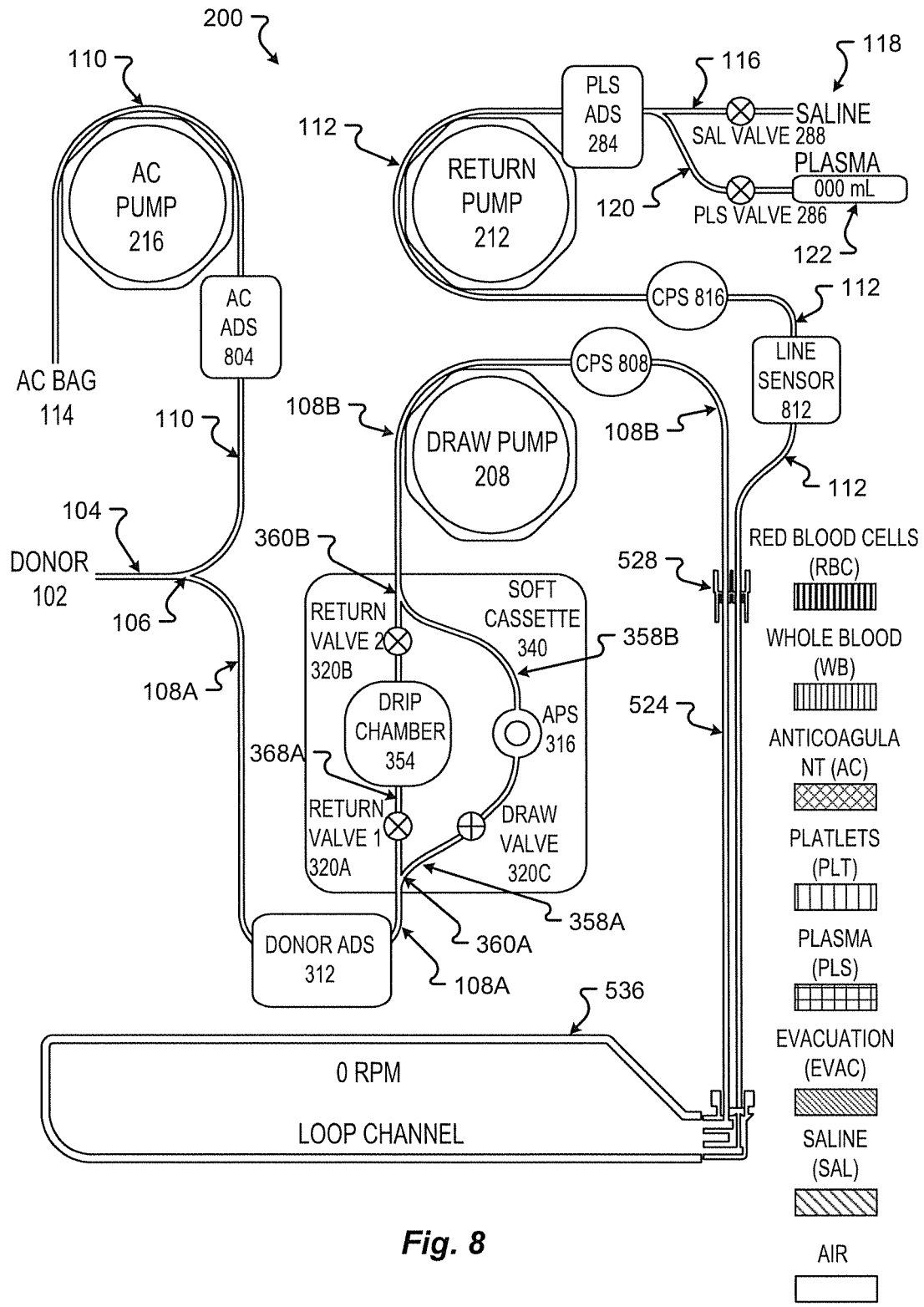
FIG. 8 is a functional diagram of an embodiment of the apheresis system in accordance with embodiments of the present disclosure.

A functional diagram of the apheresis system 200 may be as shown in FIG. 8 in accordance with embodiments of the present disclosure. The description herein shows the components previously described, in FIGS. 1-7B, in a functional diagram to describe the operation of the system 200 for extracting plasma or other blood components from the whole blood of a donor 102 during an apheresis procedure or process.

The system 200 can include an anticoagulant (AC) pump 216. The AC pump 216 pumps fluid in AC tubing 110 from the AC bag 114. The AC pump 216, the AC tubing 110, and/or the AC bag 114 may be as described previously. The AC tubing 110 may also include an AC air detection sensor (ADS) 804 to detect air or fluid within the AC tubing 110. The AC ADS 804 may be the same or similar in type and/or function to sensor 284 and/or sensor 312, described previously. AC tubing 110 can intersect with and be fluidly associated with the donor feed tubing 104 and the cassette inlet tubing 108A at tubing connector 106. The tubing connector 106 can be any type of connection between tubing 110, 104, and/or 108A, as described previously.

The donor feed tubing 104 proceeds from the donor 102, where the donor 102 may be stuck with a lumen needle or other device, allowing whole blood to flow from the donor 102 into the apheresis system 200 and allowing blood components to flow back to the donor 102. Tubing 108A may proceed to the soft cassette 340. Further, a donor air detection sensor 312 can be placed on or in tubing 108A to detect the presence of fluid and/or air within tubing 108A.

As explained previously, the soft cassette 340 can include the first cassette port 360A, which can function as, include, and/or be substantially proximate to a "Y" connector or section, or branches, that separates the tubing 108A into the first bypass branch 358A and the first tubing section 368A (the "Y" section will be designated by reference character 360A). The two tubing sections 358 and 368 can reconnect at the second cassette port 360B, which can also function as, include, and/or be substantially proximate to a second "Y" connector or section (the second "Y" section will be designated by reference character 360B). Tubing 358 is bisected by the fluid sensor 316, which separates the tubing 358 into the first bypass branch 358A and the second bypass branch 358B. Likewise, tubing 368 is bisected by the drip chamber 354 that separates tubing 368 into a first tubing section 368A and a second tubing section 368B.

The first tubing section 368A can include a first fluid control valve 320A. The second tubing second 368B can likewise include a second fluid control valve 320B. The first bypass branch 358A can similarly include a draw fluid control valve 320C. As such, the various sections of tubing 368A, 358A, 358B, and 368B can be isolated by the valves 320A, 320B, and/or 320C based on the configuration of the system 200 and depending on the operation of the system 200.

A drip chamber 354 may be disposed between the first tubing section 368A and the second tubing section 368B. The drip chamber 354 can collect a volume of whole blood and/or high hematocrit blood (blood with a high percentage of red blood cells) depending on the operation of the system 200, as described hereinafter. The fluid sensor 316, as described previously, may be disposed between the first bypass branch 358A and the second bypass branch 358B.

Loop inlet tubing 108B can connect to the second cassette port 360B and can connect the soft cassette 340 to the flexible loop 524. The loop inlet tubing 108B may also include a sensor 808, disposed on or in the tubing 108B, placed with the tubing 108B before connecting with the system static loop connector 528 of the flexible loop 524. The pressure sensor (CPS) 808 may detect one or more of, but not limited to: pressure, presence of fluid or air, and/or possibly another characteristic of the fluid in tube 108B. Further, a draw pump 208 can cause fluid to be pumped through tubing 108B either away from the soft cassette 340 or to the soft cassette 340.

Two or more different tubes can be connected to the flexible loop 524 through the system static loop connector 528 and provide fluid to, or receive fluid from, the blood component collection bladder 536. A loop exit tubing 112 exits the system static loop connector 528 from flexible loop 524. This loop exit tubing 112 can also include another line sensor 812 disposed thereon or therein to detect fluid, air, cellular concentration, color, and/or color change in the fluid coming from the flexible loop 524; the line sensor 812 can be the same or similar in type and/or function to sensors 804, 312, 320, 808, and/or 284 previously described. A second CPS sensor 816 or fluid sensor may also be disposed in or on line 112. Sensor 816 may detect one or more of, but not limited to: the presence or absence of fluid, pressure within tubing 112, and/or other characteristic of the fluid in tubing 112. Similarly, sensor 816 can be the same or similar in type and/or function to sensors 804, 312, 320, 808, 812 and/or 284 previously described.

Loop exit tubing 112 may then flow into a plasma air detection sensor 284 before the saline and plasma tubing y-connector 280 separates the tubing 112 into saline tubing 116 and plasma tubing 120. The return pump 212 may interact with the loop exit tubing 112 and can cause fluid or air to flow through tubing 112 from either the flexible loop 524 or from a saline bag 118 and/or a plasma collection bottle 122.

The saline bag 118 and associated tubing can be as previously described and can provide saline through the system 200 back to the donor 102. A saline flow control valve 288 can isolate the saline bag 118 from the rest of the system 200. Further, a plasma collection bottle 122 can receive plasma from the flexible loop 524 when processed or separated from the whole blood. The plasma collection bottle 122 can be selectively isolated from the system by the plasma flow control valve 286.

Figure 9:
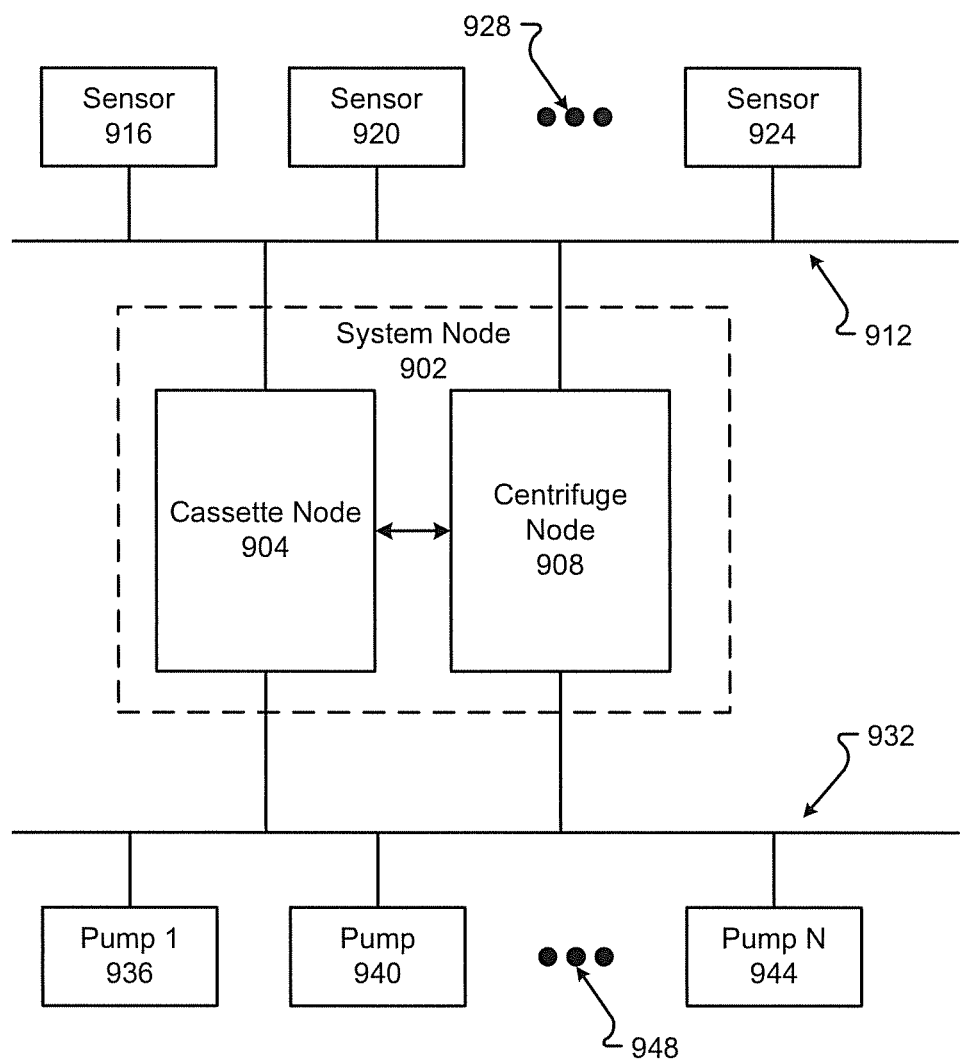
FIG. 9 is a block diagram of the electrical system of the apheresis system in accordance with embodiments of the present disclosure.

An embodiment of the electrical and control system 900 controlling the functions of the apheresis system 200 may be as shown in FIG. 9 in accordance with embodiments of the present disclosure. The control system 900 can include one or more nodes, which can include various hardware, firmware, and/or software configured to control and/or communicate with the mechanical, electromechanical, and electrical components of the apheresis system 200.

Each node may function to control a different part of the apheresis system 200. For example, the control system 900 can include a cassette node 904 and a centrifuge node 908, which may control or communicate with the components of the blood component collection set 500 (and the associated hardware or mechanical components interfacing with the soft cassette assembly 300) and the centrifuge assembly 400 (and the associated hardware or mechanical components associated therewith), respectively. The cassette node 904 and centrifuge node 908 may be in communication either wirelessly or through some other electrical or data connection. In some configurations, the separate nodes 904, 908 may be two portions of a single node 902. As such, each node 904, 908 may have the same physical hardware operating to control different functions. An example of the cassette node 904 may be as described in conjunction with FIG. 10; a centrifuge node 908 may be as described in conjunction with FIG. 11.

Each of the nodes 904, 908 may be in communication with one or more sensors 916, 920, and/or 924. There may be more or fewer sensors than those shown in FIG. 9, as represented by ellipsis 928. Each node 904, 908 can communicate directly to each sensor 916-924 or may communicate with the several sensors 916-924 via a bus 912. The bus 912 may communicate by any type of communication protocol, such as universal serial bus (USB), a universal asynchronous receive/transmit (UART), or other types of bus systems or parallel communication connections. Thus, the bus 912 may be optional, but is shown as a possible communication platform to communicate with the various sensors 916-924. The sensors 916-924 can be any type of sensor that can communicate information about light, fluid, the presence of air, color, pressure, etc., as described herein. Some of the sensors 916-924 can include sensors 312, 316, 804, 808, 812, 816, and/or 284. The function of these sensors 912-924 may be as described hereinafter.

The nodes 904, 908 may also communicate with one or more pump drives, pump motors, etc. 936, 940, 944, simply referred to as "pumps." There may be more or fewer pumps than are shown in FIG. 9, as represented by ellipsis 948. The nodes 904, 908 can communicate with the pumps 936-944 through direct wired or wireless communication or through a bus 932. The bus 932 can be a control area network (CAN) bus, USB, or other type of bus architecture to communicate with the pumps 936-944. The pumps 936-944 can include pumps 216, 208, and/or 212, as previously described. The function of the pumps 936-944 may be described as herein.

Figure 10:
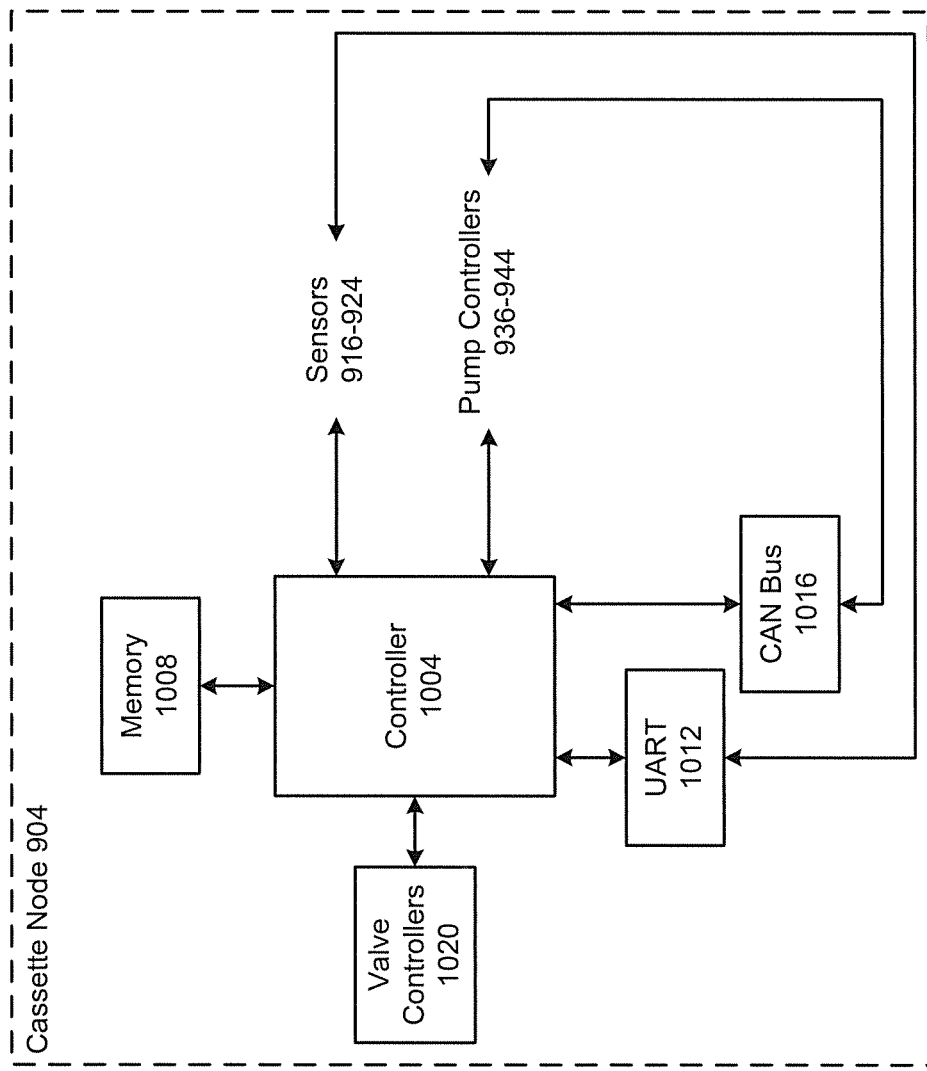
FIG. 10 is a further block diagram of the electrical system of the apheresis system in accordance with embodiments of the present disclosure.

An embodiment of the cassette node 904 may be as shown in FIG. 10 in accordance with embodiments of the present disclosure. The cassette node 904 can include one or more of a controller 1004, a memory 1008, a valve controller 1020, and/or communication interfaces for a CAN bus 1016, a UART 1012, or other types of buses. The cassette node 904 can include other hardware, firmware, and/or software that are not shown for clarity.

The controller 1004 can be any type of microcontroller, microprocessor, Field Programmable Gate Array (FPGA), Application Specific Integrated Circuit (ASIC), etc. An example controller 1004 may be the NK10DN512VOK10 microcontroller, made and sold by N9P USA, Incorporated, which is a microcontroller unit with a 32-bit architecture. Other types of controllers are possible. The controller 1004 can control other types of devices or direct the functions of other types of devices, such as valves 320A, 320B, 320C, 286, 288, pumps 936-944, etc. Further, the controller 1004 can communicate with various sensors 916-924 or other devices to receive or send information regarding the function of the apheresis system 200.

Other examples of the processors or microcontrollers 1004, as described herein, may include, but are not limited to, at least one of Qualcomm® Snapdragon® 800 and 801, Qualcomm® Snapdragon® 610 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, ARM® Cortex™-M processors, ARM® Cortex-A and ARM926EJ-S™ processors, other industry-equivalent processors, and may perform computational functions using any known or future-developed standard, instruction set, libraries, and/or architecture.

The memory 1008 can be any type of memory including random access memory (RAM), read only memory (ROM), electrically erasable programmable ROM (EEPROM), a portable compact disc read-only memory (CD-ROM), an optical storage device, a magnetic storage device, any suitable combination of the foregoing, or other type of storage or memory device that stores and provides instructions to program and control the controller 1004. The memory 1008 may provide all types of software or firmware that programs the functions of the controller 1004, as described hereinafter.

The controller 1004 can communicate with one or more valve controllers 1020. Each valve 320A, 320B, 320C, 286, 288, as described herein, may be controlled by a valve controller 1020 and may be associated with a component of the system 200, as described herein. The valve controller 1020 can provide the electrical signal, operational directive, or power to close or open any one of the valves described herein, for example, the saline and plasma valve housing 276, the plasma flow control valve 286, the saline flow control valve 288, the first fluid control valve 320A, the first fluid control valve 320A, and/or the draw fluid control valve 320C, etc.

The controller 1004 can also be connected to a bus 912, 932 (e.g., UART bus, CAN bus), or other busses through transceivers 1012, 1016 provided outside of the controller 1004 or integral to the controller 1004. The UART transceiver 1012 may communicate with one or more of the sensors 916-924 or other devices. Likewise, the CAN bus transceiver 1016 can communicate with one or more of the pump controllers 936-944 or other devices. UART transceivers 1012 and busses and CAN bus transceivers 1016 and busses are well known in the art and need not be explained further herein.

Figure 11:
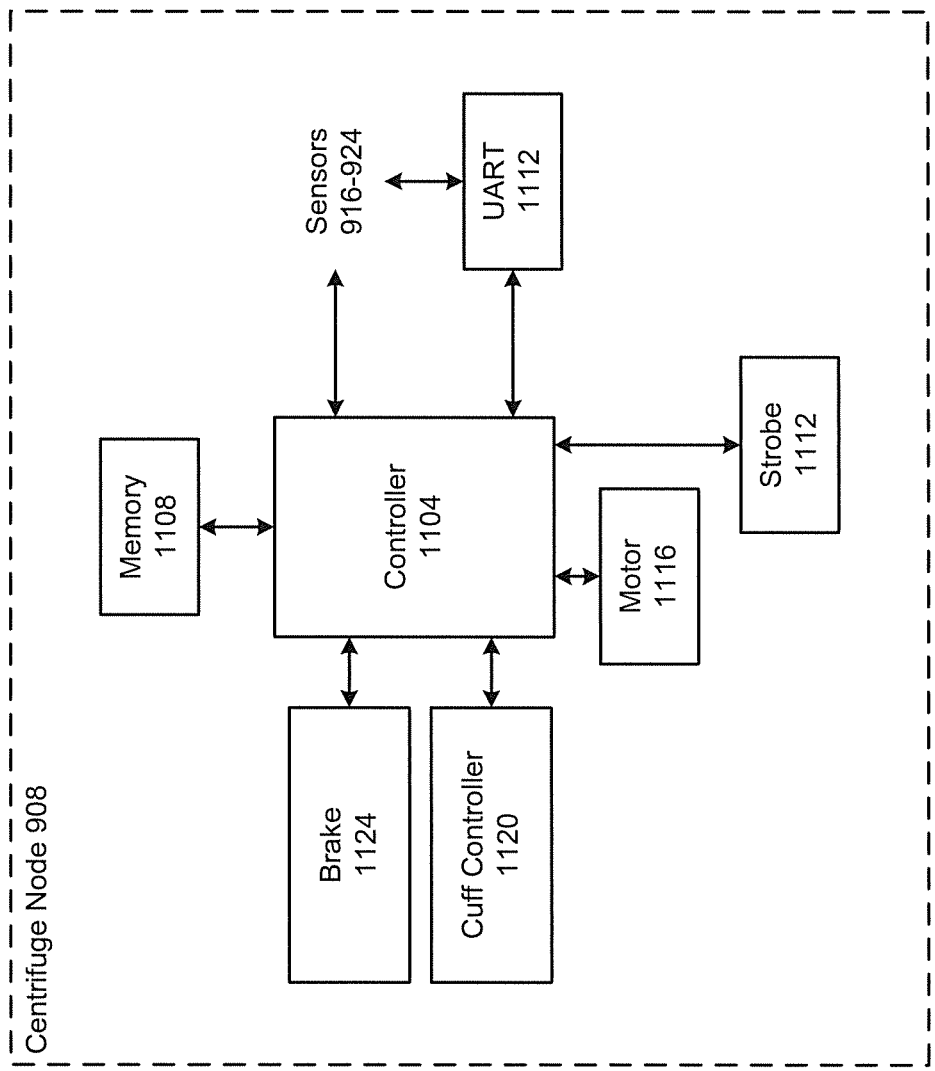
FIG. 11 is a further block diagram of the electrical system of the apheresis system in accordance with embodiments of the present disclosure.

An embodiment of the centrifuge node 908 may be as shown in FIG. 11, in accordance with embodiments of the present disclosure. The centrifuge node 908, can include the same or similar types of components as the cassette node 904. For example, the centrifuge node 908 can include a controller 1104, a UART transceiver 1112, etc. Similar to the controller 1004, the controller 1104 can be any type of processor or microcontroller, for example the NK10DN512VOK10 microcontroller unit with 32-bit architecture from N9P USA, Incorporated, as mentioned previously, or other controllers, processors, etc., for example, the devices mentioned previously.

The controller 1104 can communicate with the sensors 916-924 directly, through the UART transceiver 1112, or through other busses or systems. The controller 1104 can also communicate with a brake controller 1124 that can brake or slow and stop the centrifuge 400. Likewise, a controller 1104 can communicate with a motor transceiver 1116 that communicates with a motor power system or a motor controller that functions to spin up or rotate the centrifuge 400 or control the speed setting or other function of the centrifuge 400.

In some configurations, the controller 1104 can also communicate with a cuff controller 1122 that can change or set the pressure of a pressure cuff on a donor's arm during the apheresis process. Further, the controller 1104 can communicate with and/or control a strobe 1112, which can be any light that flashes at a periodicity in synchronicity with the rate of spin of the motor, such that an operator of the apheresis system 200 can see the operation of the filler 460, as described previously. Thus, the controller 1104 can communicate with the strobe 1112 to change the frequency of the flashing of the strobe light 1112, the intensity of the strobe light 1112, etc.

Figure 12:
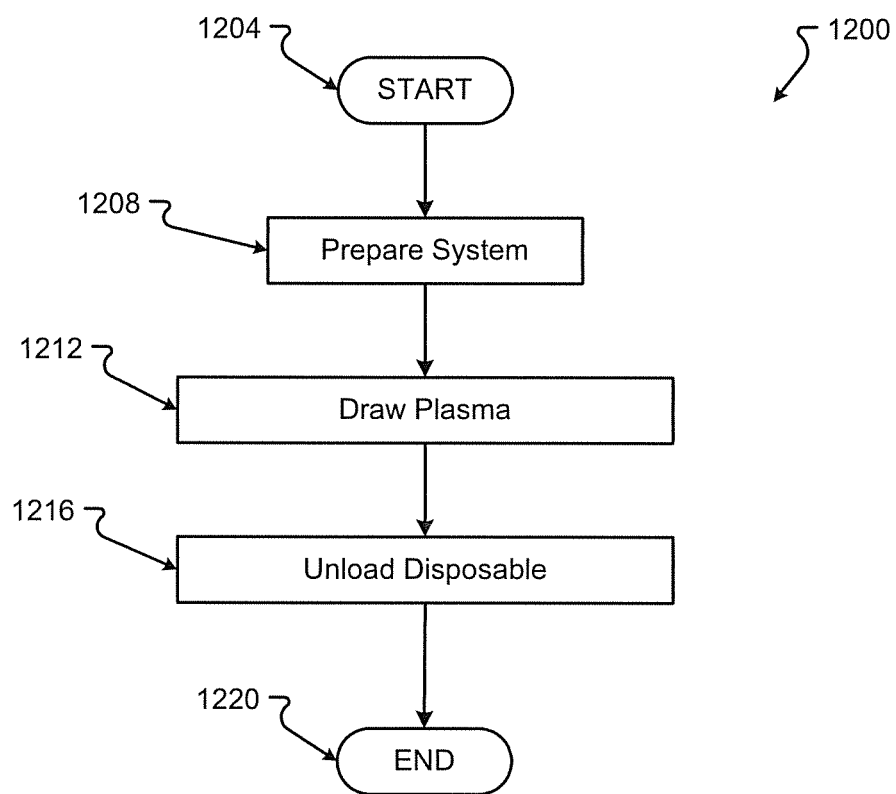
FIG. 12 is a process diagram of a method for conducting apheresis in accordance with embodiments of the present disclosure.

Embodiments of a method 1200 used to complete blood component (e.g., plasma) apheresis, with the system 200, may be as shown with FIG. 12, in accordance with embodiments of the present disclosure. The method 1200 may be described in conjunction with FIGS. 17A-17T. As such, the method 1200 will be described in relation or with reference to those figures. A general order for the steps of the method 1200 is shown in FIG. 12. Generally, the method 1200 starts with a start operation 1204 and ends with operation 1220. The method 1200 can include more or fewer steps or can arrange the order of the steps differently than those shown in FIG. 12. The method 1200 can be, at least partially, executed as a set of computer-executable instructions executed by a computer system, processor, cassette microcontroller 1004, centrifuge microcontroller 1104, and/or another device and encoded or stored on a computer readable medium. In other configurations, the method 1200 may be executed, at least partially, by a series of components, circuits, gates, etc. created in a hardware device, such as a System on Chip (SOC), Application Specific Integrated Circuit (ASIC), and/or a Field Programmable Gate Array (FPGA). Hereinafter, the method 1200 shall be explained with reference to the systems, devices, valves, pumps, sensors, components, circuits, modules, software, data structures, signaling processes, models, environments, apheresis systems, etc. described in conjunction with FIGS. 1-11.

The method 1200 can generally be separated into three phases, where each phase includes a series of steps or processes. Each of the three phases is described in FIG. 12 and with reference to FIGS. 13-16, which describe the steps or processes. The method 1200 can include a preparing the system phase, in step 1208. In this phase 1208, the operator can prepare the system 200 for apheresis, which might include steps to place the needle in the donor 102, conduct other operations to prepare for blood draw, insert the blood component collection set 500 into the system, etc. An example of the steps that may be included in the preparing the system phase 1208 may be as described in conjunction with FIG. 13.

The method 1200 may then enter a draw plasma phase, in step 1212. The draw plasma phase 1212 may be as described in conjunction with FIG. 14. The draw plasma phase 1212 can include the drawing of the blood, centrifuging of blood to extract plasma (and/or other blood components), pushing the high hematocrit blood (e.g., red blood cells), and/or other blood components, back to the donor 102 in various return cycles (until a full sample of plasma and/or other blood component is collected), etc. The start of the return cycles may be triggered based on the presence, at some predetermined position in the apheresis system, of one or more blood components, e.g., platelets, red blood cells, etc.

The final phase of the method 1200 can be an unload disposable phase, in step 1216. The unload disposable phase 1216 may be described in conjunction with FIG. 15. The unload disposable phase 1216 can include the completion of the apheresis process, the removing of the needle from the donor 102, unloading the blood component collection set 500, and completing the procedure. Each of the three phases 1208-1216, and the steps or process associated therewith, will now be described hereinafter.

Figure 13:
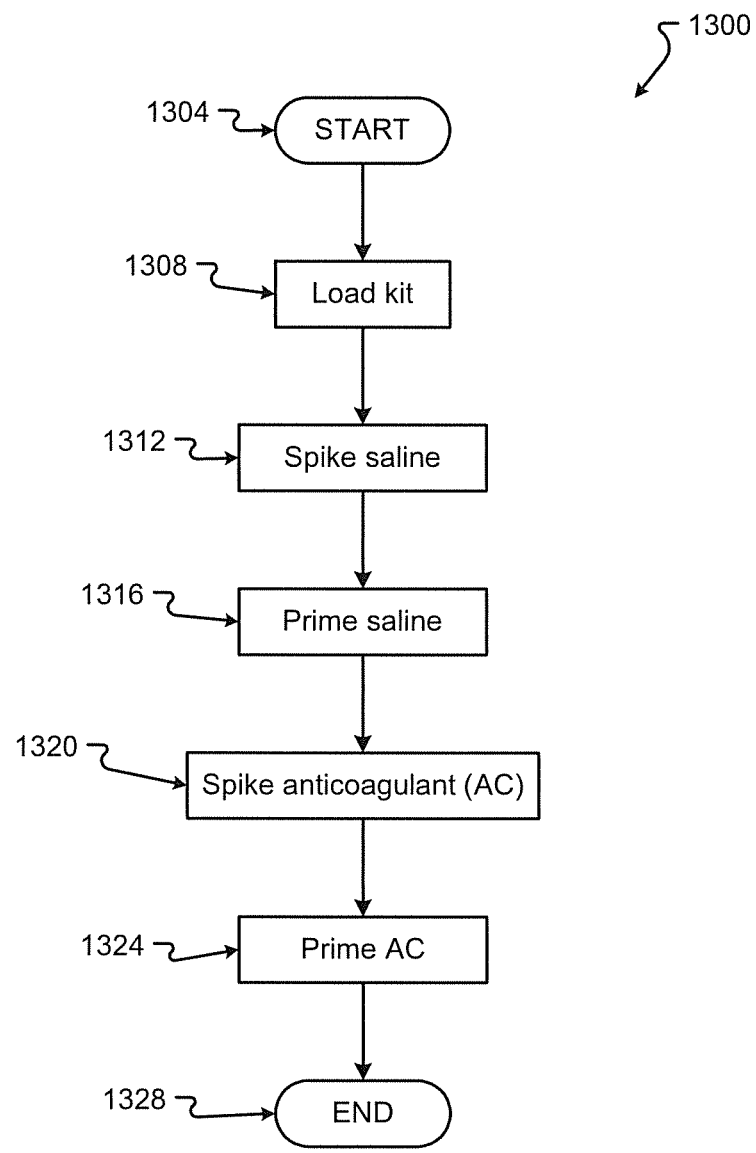
FIG. 13 is a process diagram of a method for conducting apheresis in accordance with embodiments of the present disclosure.

A method for prepping the apheresis system 200, as described in phase 1208, may be as shown in FIG. 13, in accordance with embodiments of the present disclosure. A general order for the steps of the method 1300 is shown in FIG. 13. Generally, the method 1300 starts with a start operation 1304 and ends with operation 1328. The method 1300 can include more or fewer steps or can arrange the order of the steps differently than those shown in FIG. 13. The method 1300 can be, at least partially, executed as a set of computer-executable instructions executed by a computer system, processor, cassette microcontroller 1004, centrifuge microcontroller 1104, and/or other devices and encoded or stored on a computer readable medium. In other configurations, the method 1300 may be executed, at least partially, by a series of components, circuits, gates, etc. created in a hardware device, such as a SOC, ASIC, and/or a FPGA. Hereinafter, the method 1300 shall be explained with reference to the systems, devices, valves, pumps, sensors, components, circuits, modules, software, data structures, signaling processes, models, environments, apheresis systems, methods, etc. described in conjunction with FIGS. 1-12.

A user, or operator, may load the blood component collection set 500, in step 1308. In this step 1308, the user can load the blood component collection set 500 into the system 200, including inserting the flexible loop 524 into the loop containment bracket 426 and the blood component collection bladder 536 into the filler 460 (which may both be as described in FIG. 16). Further, the soft cassette 340 may be mounted in the soft cassette assembly 300, as described in conjunction with FIGS. 1, 2A, 2B, 3A, and/or 3B. The loop inlet tubing 108B can be inserted into the lead tubing guide 244 and/or end tubing guide 252 to the draw pump 208 to cause fluid movement in the loop inlet tubing 108B and other parts of the blood component collection set 500. Similarly, the anticoagulant tubing 110 can be placed into tubing guides, similar to guides 244, 252, to allow the AC pump 216 to move anticoagulant into the anticoagulant tubing 110 or other parts of the blood component collection set 500. The loop exit tubing 112 can be inserted into similar guides 244, 252 to allow the return pump 212 to move blood components (e.g., plasma) into the plasma collection bottle 122 or move saline from the saline bag 118 into the loop exit tubing 112 or other portions of the blood component collection set 500.

Figure 17A:
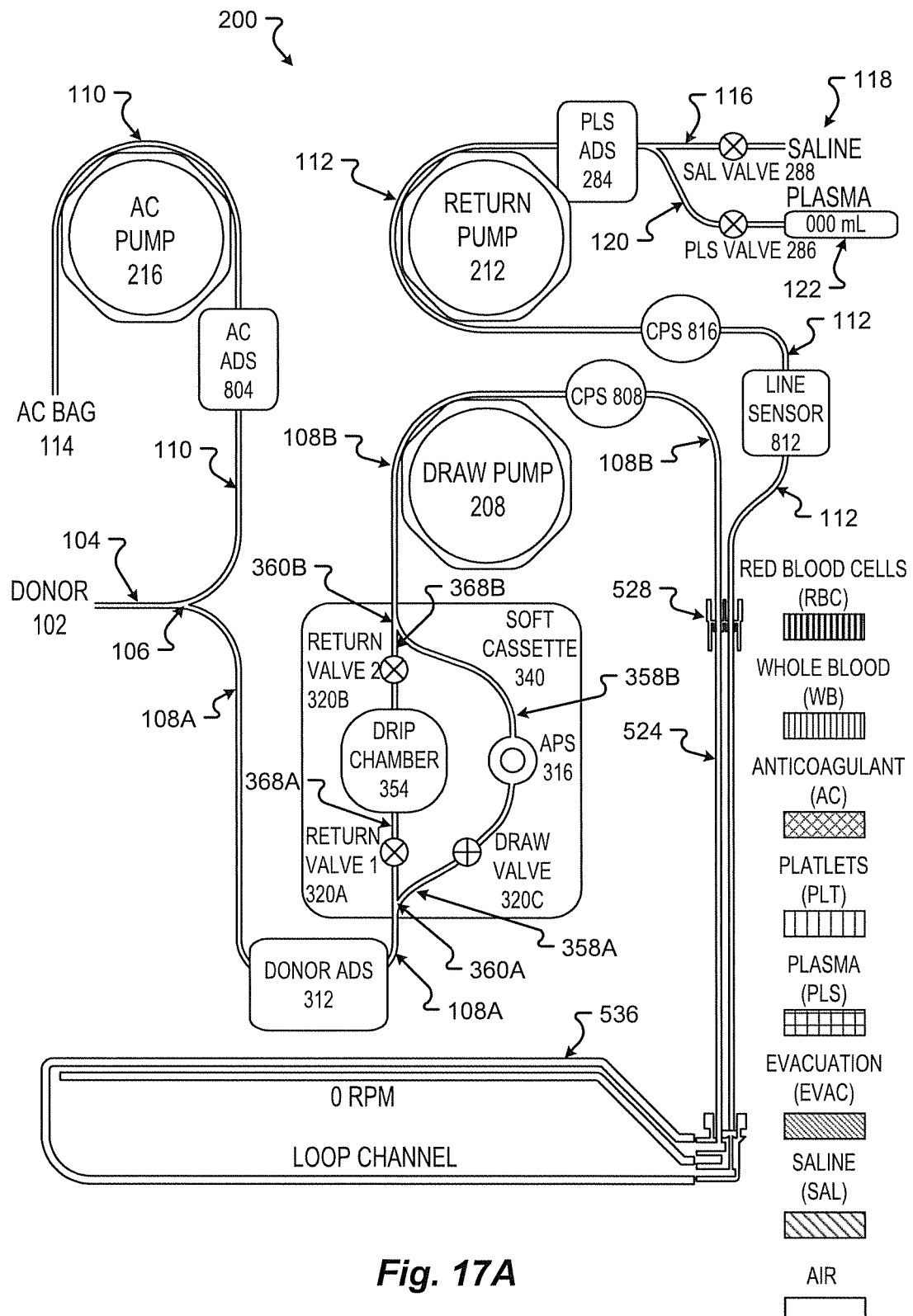
FIG. 17A is a functional diagram of the apheresis system during an apheresis procedure in accordance with embodiments of the present disclosure.
Figure 17B:
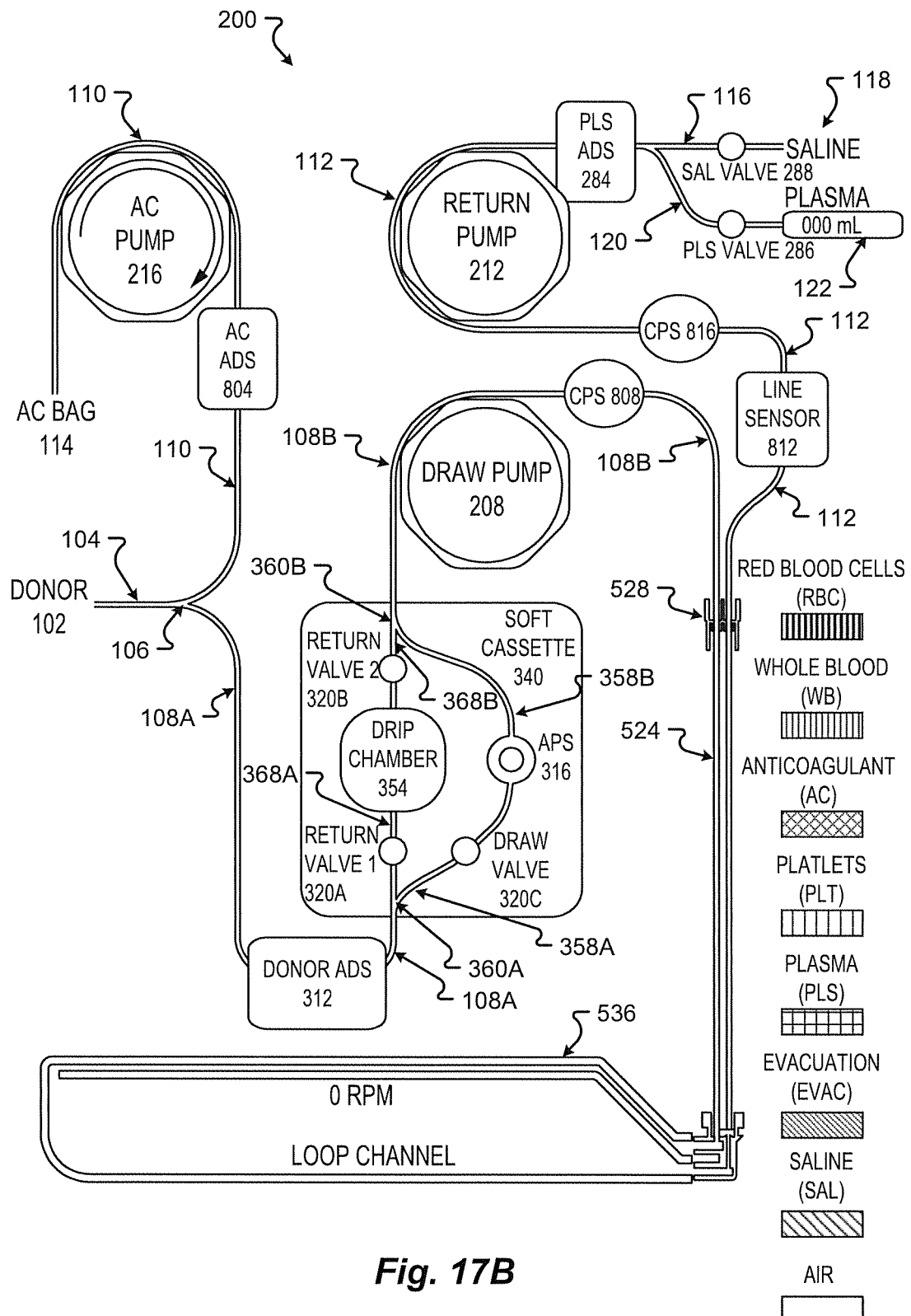
FIG. 17B is another functional diagram of the apheresis system during an apheresis procedure in accordance with embodiments of the present disclosure.
Figure 17C:
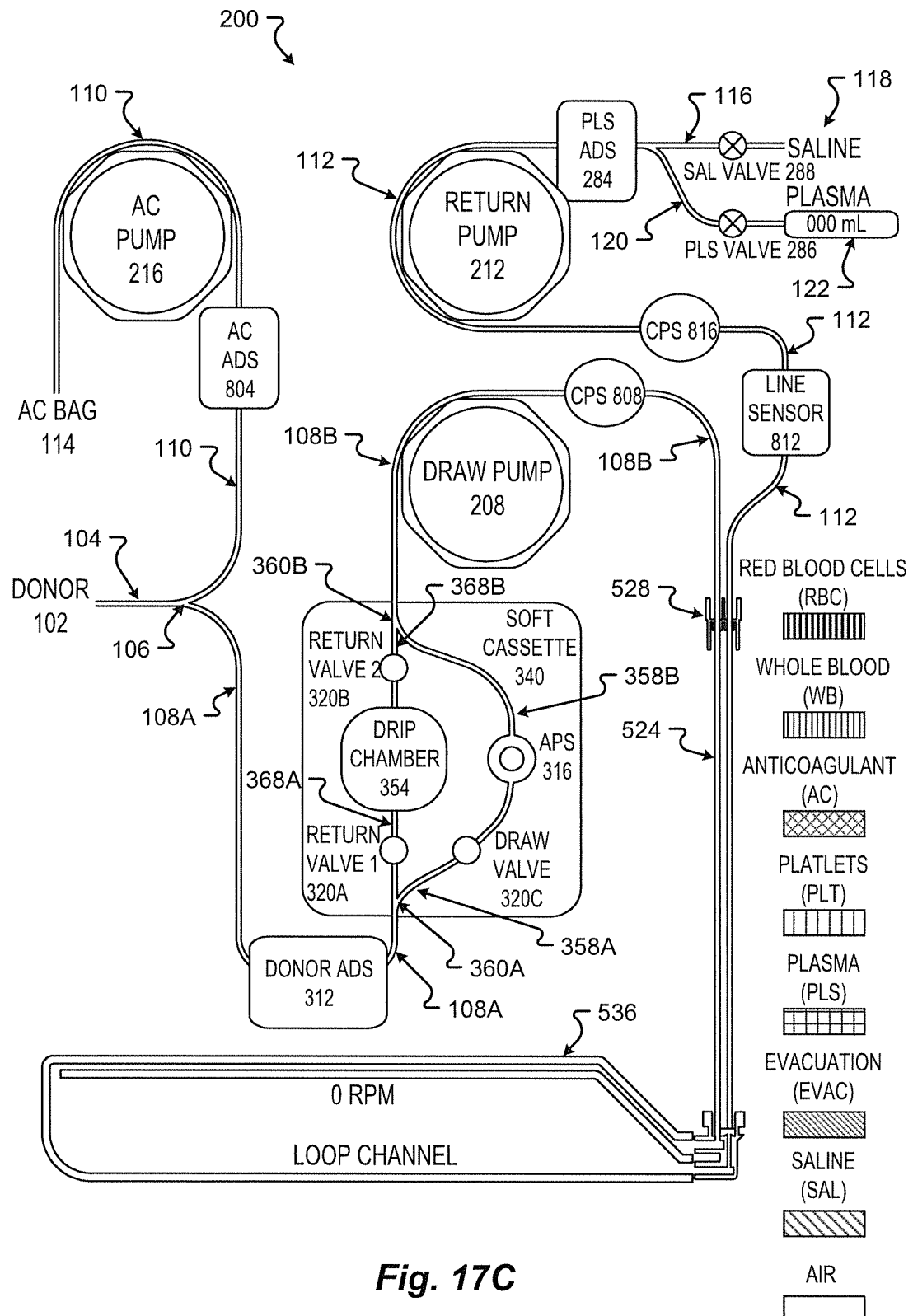
FIG. 17C is another functional diagram of the apheresis system during an apheresis procedure in accordance with embodiments of the present disclosure.

As shown in FIG. 2D, the saline and plasma tubing y-connector 280 can be mounted into a plasma and saline valve control system 228 to allow the valves 286, 288 to control fluid flow from and/or to the plasma collection bottle 122 and/or the saline bag 118. The AC bag 114 may be mounted onto an anticoagulant support 232A, the plasma collection bottle 122 can be placed in the plasma collection cradle 232C, and the saline bag 118 can be mounted onto the saline support 232B, as described in FIGS. 1-2B. With the blood component collection set 500 mounted in the apheresis system 200, the apheresis system 200 may appear as shown in FIGS. 17A and 17B. The status of the various components of the apheresis system 200, during this step, may be as shown below:

TABLE 1

| Load Kit Status Load Kit Status | | | | |
|---|---|---|---|---|
| Component Name | Flow Rate (mL/min) | Occlude? | Open/ Closed? | Spin Rate (RPM) |
| Draw pump 208 | 0 | No | | |
| Return pump 212 | 0 | No | | |
| Anticoagulant pump 216 | 0 | | | |
| Plasma flow control valve 286 | | | Open | |

TABLE 1-continued

| Load Kit Status Load Kit Status | | | | |
|---|---|---|---|---|
| Component Name | Flow Rate (mL/min) | Occlude? | Open/ Closed? | Spin Rate (RPM) |
| Saline flow control valve 288 | | | Open | |
| First fluid control valve 320A | | | Open | |
| Second fluid control valve 320B | | | Open | |
| Draw fluid control valve 320C | | | Open | |
| Filler 460 | | | | 0 |

As shown in the above table and in subsequent tables, the draw pump 208 and return pump 212 can occlude the loop inlet tubing 108B and the anticoagulant tubing 110, respectively. In this way, the draw pump 208 and return pump 212 function as "valves" that selectively allow or disallow fluid flow. A minus sign, "−", in the "Flow Rate" column represents that the pump is moving in a counterclockwise rotation. The abbreviation "AF" means "Auto-flow" and represents that the pump is functioning at the flowrate of the blood coming from the donor 102. This AF flowrate prevents the apheresis system 200 from syphoning blood from the donor 102 or backing the flow of blood into the donor 102 and/or AF optimizes draw and return flowrates while improving donor safety.

The saline bag 118 may be spiked, in step 1312. A user can remove any safety coverings from a bag spike fitting 512, at the distal end of the saline tubing 116, to puncture the saline bag 118, which contains the saline. In other configurations, the saline tubing 116 may be mechanically attached to the saline bag 118 (e.g., by a Luer connector) and a frangible device or other removable barrier may be modified, by a user, to allow for the flow of saline from the saline bag 118. Thus, spiking the saline bag 118 allows saline to flow into the blood component collection set 500 to or through the saline flow control valve 288. The status of the various components of the apheresis system 200, during this step, may be as shown below:

TABLE 2

| Spike Saline Status Spike Saline Status | | | | |
|---|---|---|---|---|
| Component Name | Flow Rate (mL/min) | Occlude? | Open/ Closed? | Spin Rate (RPM) |
| Draw pump 208 | 0 | No | | |
| Return pump 212 | 0 | Yes | | |
| Anticoagulant pump 216 | 0 | | | |
| Plasma flow control valve 286 | | | Closed | |
| Saline flow control valve 288 | | | Closed | |
| First fluid control valve 320A | | | Open | |
| Second fluid control valve 320B | | | Open | |
| Draw fluid control valve 320C | | | Open | |
| Filler 460 | | | | 0 |

Figure 17D:
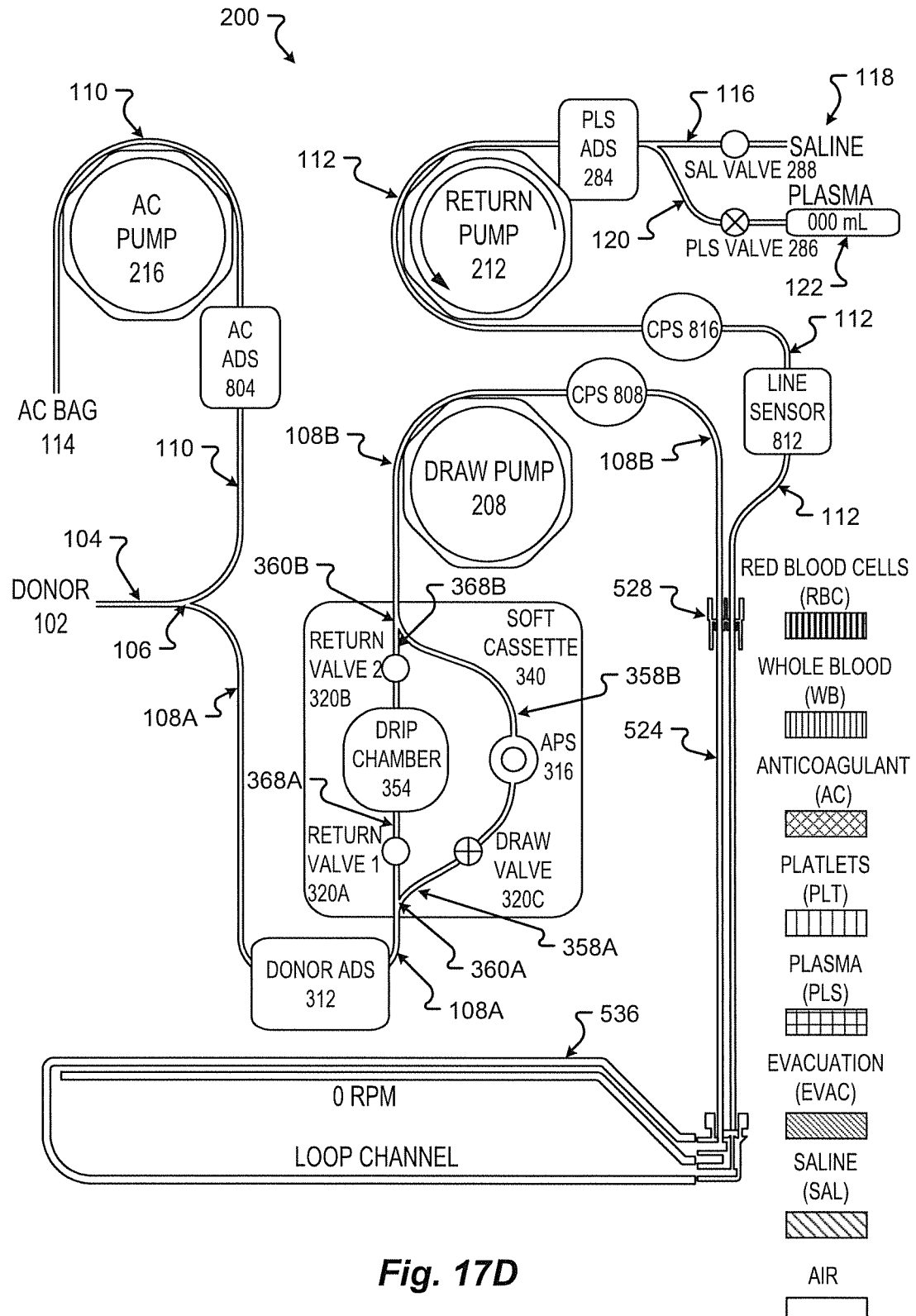
FIG. 17D is another functional diagram of the apheresis system during an apheresis procedure in accordance with embodiments of the present disclosure.
Figure 17E:
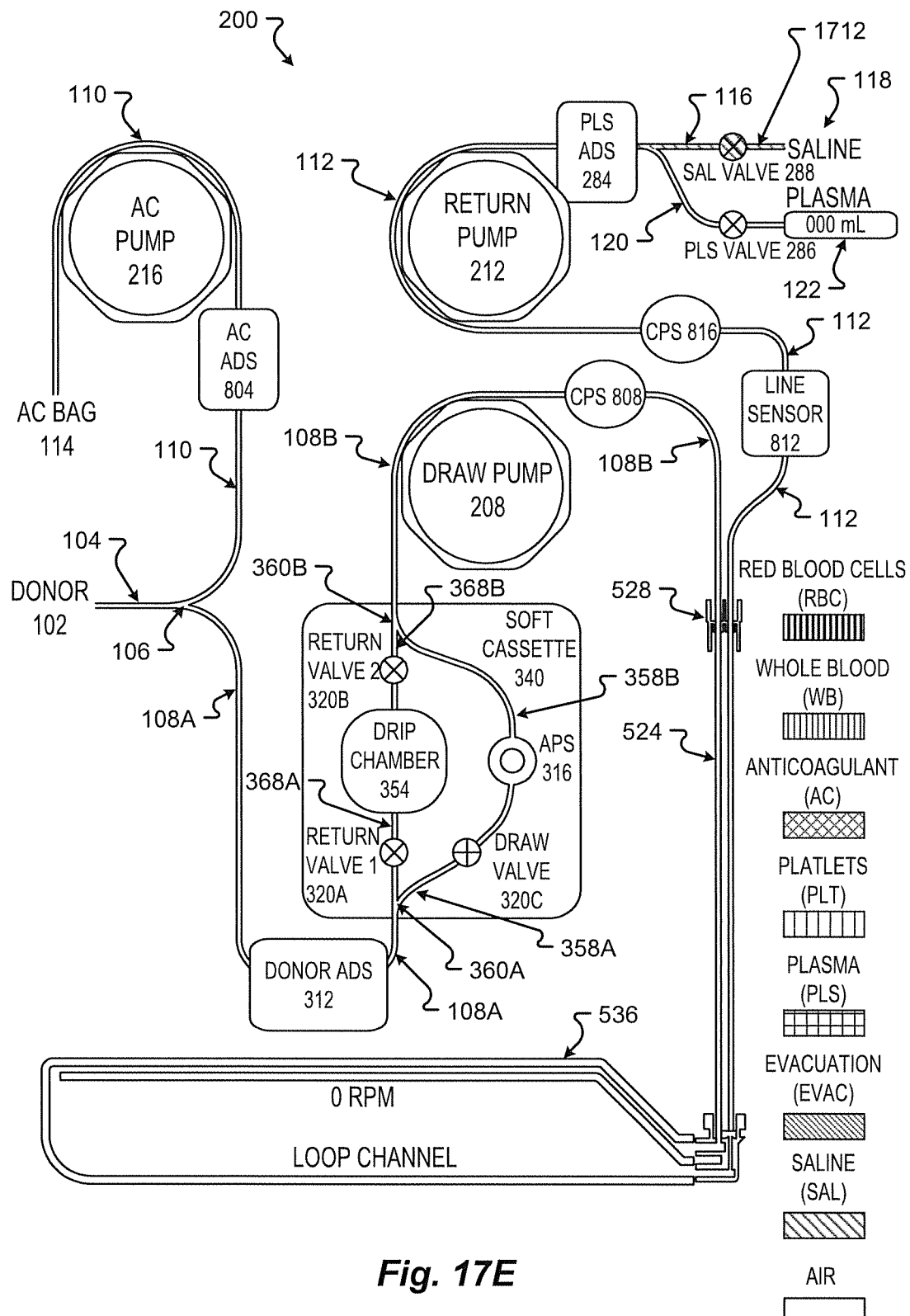
FIG. 17E is another functional diagram of the apheresis system during an apheresis procedure in accordance with embodiments of the present disclosure.

In step 1316, the saline 1712 is primed. Priming the saline 1712 includes the cassette microcontroller 1004 directing the opening of the saline flow control valve 288, as shown in FIG. 17D. The cassette microcontroller 1004 can receive instructions for a user interface or program to begin the apheresis process, which begins by priming the saline 1712. Thus, the saline 1712 moves from the saline bag 118, through the saline flow control valve 288 to the plasma air detection sensor 284. The cassette microcontroller 1004 directs the counterclockwise rotation of the return pump 212 to cause the volumetric flow of saline 1712 from the saline bag 118 and through saline tubing 116 and the saline and plasma tubing y-connector 280, mounted in the plasma and saline valve control system 228, to the plasma air detection sensor 284. Upon the plasma air detection sensor 284 detecting either the presence of liquid or the lack of air in the loop exit tubing 112, a signal is sent to the cassette microcontroller 1004. The cassette microcontroller 1004 may then direct the return pump 212 to stop rotations and direct the saline flow control valve 288 to close, which prevents saline 1712 from further entering the loop exit tubing 112 substantially beyond the plasma air detection sensor 284. At this point in the process, the apheresis system may appears as shown in FIG. 17E. The status of the various components of the apheresis system 200, during this step, may be as shown below:

TABLE 3

Prime Saline Status
Prime Saline Status

| Component Name | Flow Rate (mL/min) | Occlude? | Open/ Closed? | Spin Rate (RPM) |
|---|---|---|---|---|
| Draw pump 208 | 0 | No | | |
| Return pump 212 | −10 | Yes | | |
| Anticoagulant pump 216 | 0 | | | |
| Plasma flow control valve 286 | | | Closed | |
| Saline flow control valve 288 | | | Open | |
| First fluid control valve 320A | | | Open | |
| Second fluid control valve 320B | | | Open | |
| Draw fluid control valve 320C | | | Open | |
| Filler 460 | | | | 0 |

It should be noted that the return pump 212 is described as moving in the counterclockwise rotation. This direction of rotation is associated with the location of the return pump 212 in relation to the loop exit tubing 112. If the return pump 212 is mounted with the loop exit tubing 112 below the return pump 212, the return pump 212 would rotate in the clockwise direction to move the saline 1712 from the saline bag 118. Thus, throughout this description, the direction of pump rotation will be described for the return pump 212, the draw pump 208, and/or the AC pump 216, but those directions of rotations may be different if the pumps 208, 212, 216 are mounted or placed differently. Further, other types of pumps may be used, which would change how the pumps operate to move the various liquids or air in the system 200. One skilled in the art would understand how to make these modifications to accomplish similar results as described in the following processes and steps.

Further, the volumes moved and the rates of movement in the apheresis system 200 are mentioned or described in the Tables included herein. However, these volumes and rates depend on the size of the tubing, the size of the bags used, the desired volume of the collected blood component (e.g., 880 mL of plasma), and other considerations. State or country laws and other directives may govern the volumes and rates used in the apheresis system 200 or those volumes moved and the rates of movement can be predetermined based on the direction of a medical professional or based on the characteristics of the donor 102. As such, the volumes moved and the rates of movement are only exemplary, but one skilled in the art would know which volumes moved and the rates of movement to establish for the following steps and processes.

Thereinafter, the anticoagulant (AC) 1702 may be spiked, in step 1320. Spiking the anticoagulant 1702 can be a similar process to spiking the saline 1712. For example, a tubing fitting 508 can be attached to the AC bag 114 by a user. The user may then break a frangible, open a valve or other device, or modify some structure that will allow AC 1702 to flow into the anticoagulant tubing 110. In other configurations, a needle may be inserted into the AC bag 114 by the user. At this point in the process, the apheresis system 200 may appear as shown in FIG. 17E. The cassette microcontroller 1004 may be signaled by the user, through a user interface or other user input device, that the AC bag 114 has been connected or spiked. The status of the various components of the apheresis system 200, during this step, may be as shown below:

TABLE 4

Spike Anticoagulant Status
Spike Anticoagulant Status

| Component Name | Flow Rate (mL/min) | Occlude? | Open/ Closed? | Spin Rate (RPM) |
|---|---|---|---|---|
| Draw pump 208 | 0 | No | | |
| Return pump 212 | 0 | Yes | | |
| Anticoagulant pump 216 | 0 | | | |
| Plasma flow control valve 286 | | | Closed | |
| Saline flow control valve 288 | | | Closed | |
| First fluid control valve 320A | | | Open | |
| Second fluid control valve 320B | | | Open | |
| Draw fluid control valve 320C | | | Open | |
| Filler 460 | | | | 0 |

Figure 17F:
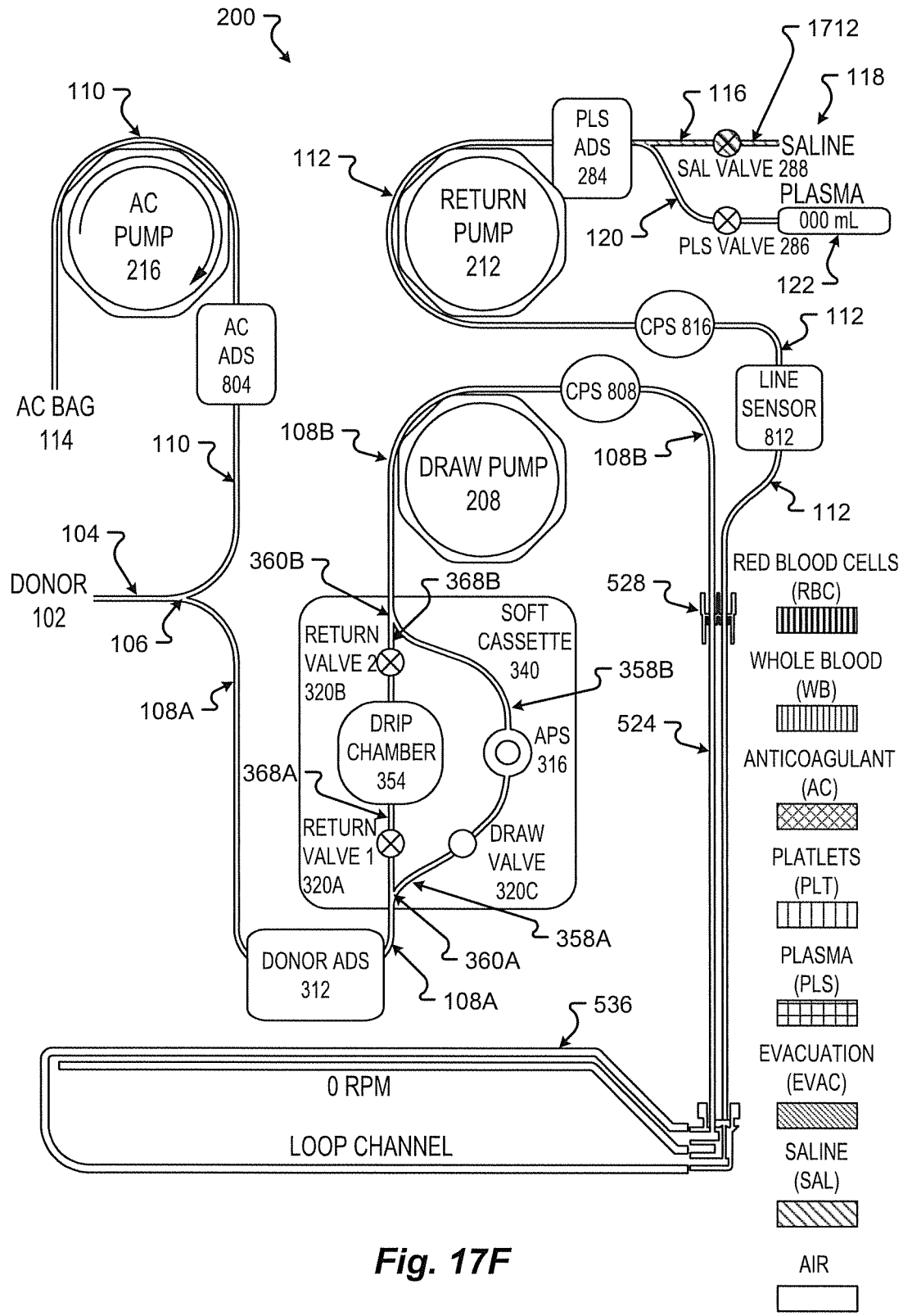
FIG. 17F is another functional diagram of the apheresis system during an apheresis procedure in accordance with embodiments of the present disclosure.
Figure 17G:
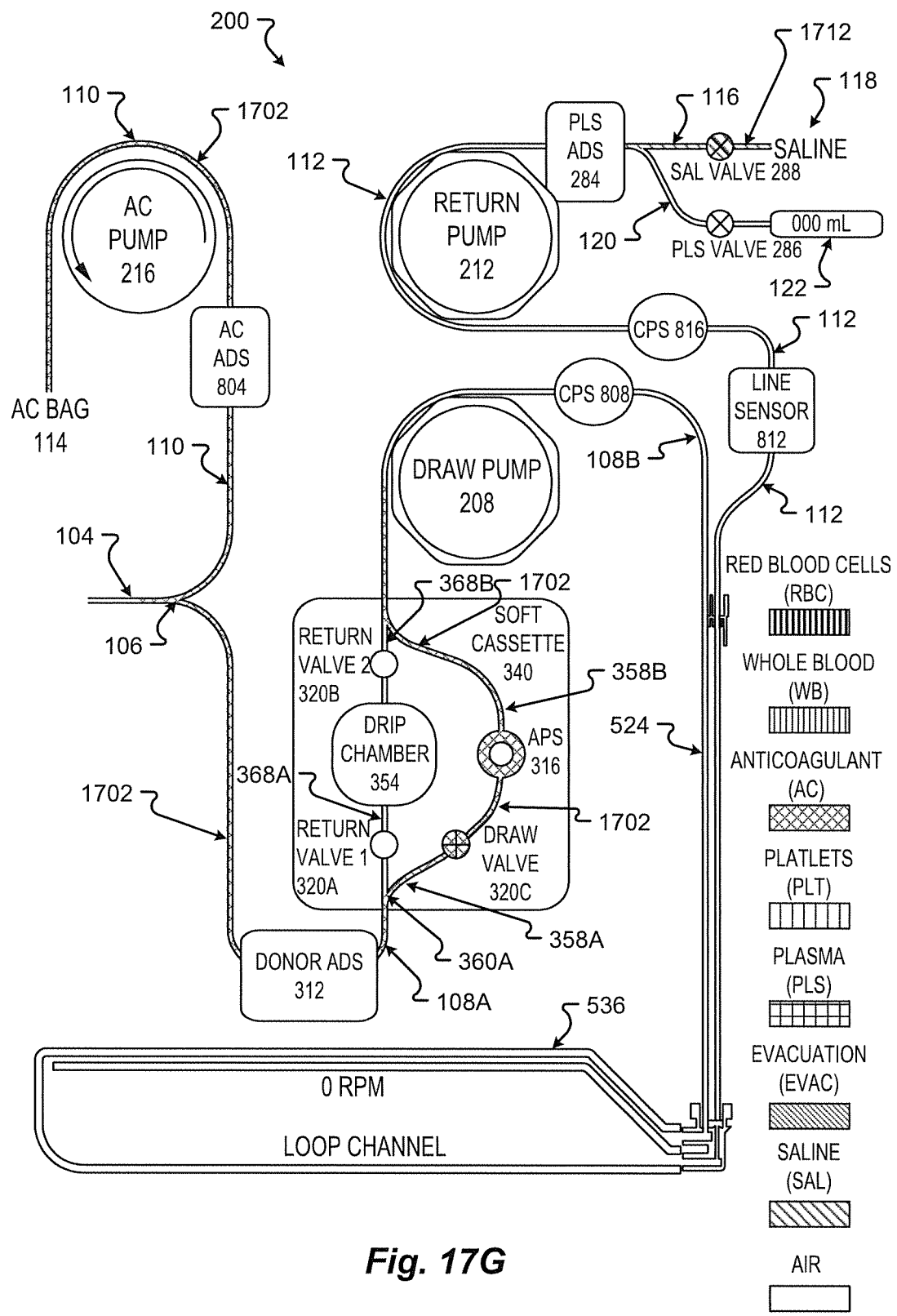
FIG. 17G is another functional diagram of the apheresis system during an apheresis procedure in accordance with embodiments of the present disclosure.

In response to the signal from the user, the cassette microcontroller 1004 may then prime the AC 1702, in step 1324. To prime the AC 1702, the cassette microcontroller 1004 can direct the AC pump 216 to operate or rotate in the clockwise direction to pump anticoagulant 1702 from the AC bag 114 into the anticoagulant tubing 110, as shown in FIGS. 17F and 17G. The donor feed tubing 104 may be blocked by a clamp, frangible device, or other structure. Thus, the AC 1702 does not flow from the donor feed tubing 104 to the donor 102. Rather, the AC pump 216 can push the anticoagulant 1702 into the cassette inlet tubing 108A, into the soft cassette 340, and partially into the loop inlet tubing 108B. In embodiments, the AC 1702 flows through the first bypass branch 358A, second bypass branch 358B, and/or the fluid sensor 316 but not necessarily into the first tubing section 368A or second tubing section 368B. Thus, the cassette microcontroller 1004 can close the first fluid control valve 320A to prevent the AC 1702 from flowing into the first tubing section 368A, drip chamber 354, or second tubing section 368B. Preplacing the AC 1702 into the first bypass branch 358A, second bypass branch 358B, and/or the fluid sensor 316 ensures proper flow of whole blood during the first draw of whole blood from the donor 102 and prevents a large volume of AC 1702 from being returned to the donor 102 from the drip chamber 354 when red blood cells are returned later in the process.

To determine when to stop the AC pump 216, cassette microcontroller 1004 can receive signals from the fluid sensor 316 and/or donor air detection sensor 312 that indicate fluid is at or is passing the sensors 312, 316. Upon the fluid sensor 316 providing indication to the cassette microcontroller 1004 that the AC 1702 has reached the sensor 316, the cassette microcontroller 1004 can continue to direct the AC pump 216 for a predetermined period of time until a known volume of AC 1702 is pumped through the second cassette port 360B and partially into the loop inlet tubing 108B. Thus, the priming of the AC 1702 leaves the apheresis system 200 in a state as shown in FIG. 17G. The status of the various components of the apheresis system 200, during this step, may be as shown below:

TABLE 5

Prime Anticoagulant Status
Prime Anticoagulant Status

| Component Name | Flow Rate (mL/min) | Occlude? | Open/ Closed? | Spin Rate (RPM) |
|---|---|---|---|---|
| Draw pump 208 | 0 | No | | |
| Return pump 212 | 0 | Yes | | |
| Anticoagulant pump 216 | 30 | | | |
| Plasma flow control valve 286 | | | Closed | |
| Saline flow control valve 288 | | | Closed | |
| First fluid control valve 320A | | | Closed | |
| Second fluid control valve 320B | | | Closed | |
| Draw fluid control valve 320C | | | Open | |
| Filler 460 | | | | 0 |

Figure 17H:
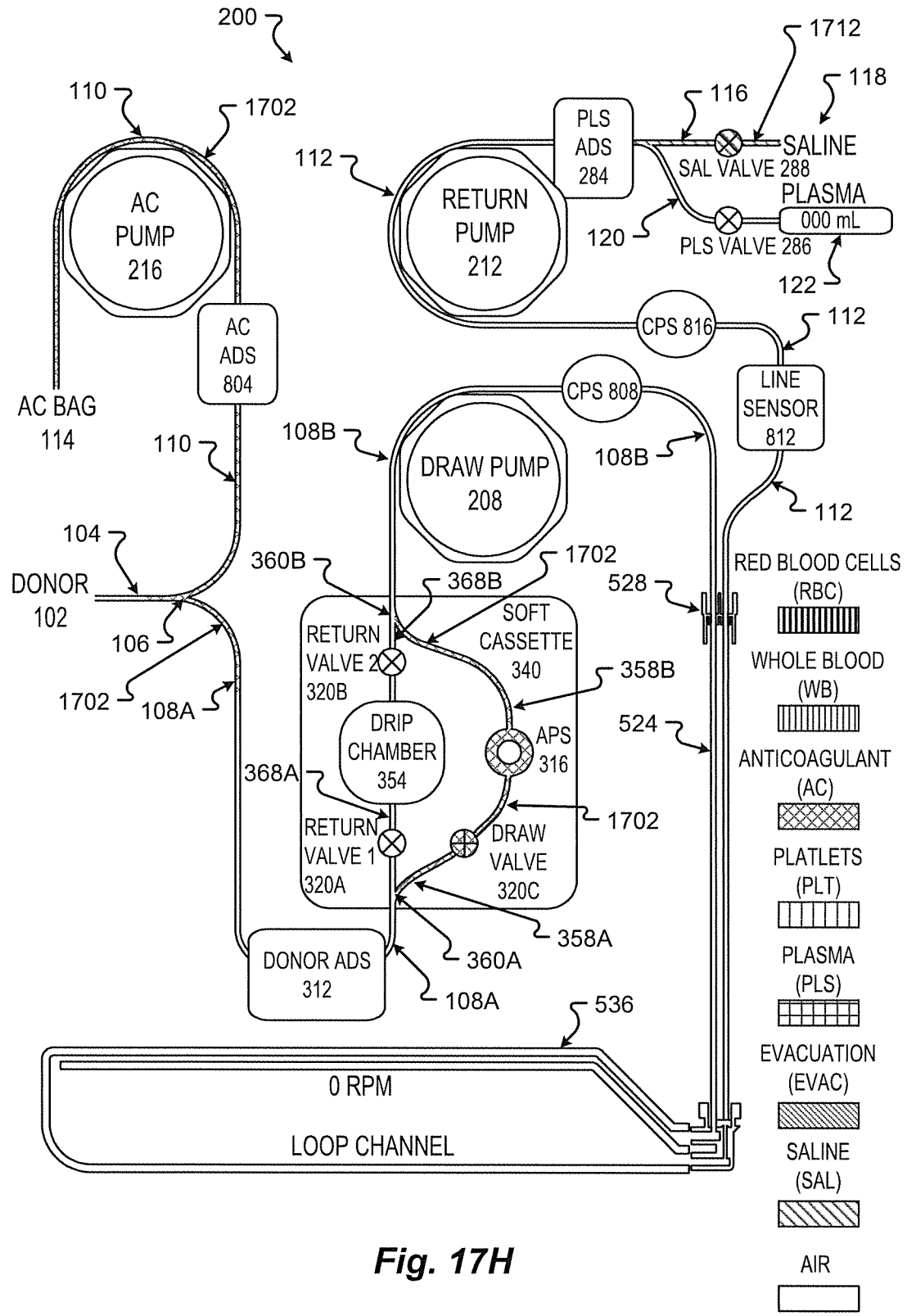
FIG. 17H is another functional diagram of the apheresis system during an apheresis procedure in accordance with embodiments of the present disclosure.

In some configurations, the direction of the AC pump 216 may be reversed, as shown in FIG. 17G. At least a portion of the anticoagulant 1702 may then be pumped back to the AC bag 114 and/or to a portion of the cassette inlet tubing 108A and/or anticoagulant tubing 110. In embodiments, the cassette microcontroller 1004 can direct the draw fluid control valve 320C to close to maintain the AC in the first bypass branch 358A, second bypass branch 358B, and/or the fluid sensor 316. The donor air detection sensor 312 can determine when the AC 1702 stops passing the sensor 312 and send a signal to the cassette microcontroller 1004. Again, the cassette microcontroller 1004 can continue to direct the AC pump 216 for a predetermined period of time until a known volume of AC 1702 is pumped back through the cassette inlet tubing 108A. Thus, the AC 1702 leaves the apheresis system 200 in a state as shown in FIG. 17H. The amount of anticoagulant left in the cassette inlet tubing 108A, the tubing connector 106, and/or the anticoagulant tubing 110 may be determined by the cassette microcontroller 1004 by an amount of time after the anticoagulant 1702 passes the donor air detection sensor 312. This process leaves some anticoagulant in cassette inlet tubing 108A but decreases the amount of AC used to prevent issues with too much AC being mixed with the incoming whole blood. At this point, the apheresis system 200 is prepared and ready to draw whole blood, in phase 1212 (FIG. 12). The status of the various components of the apheresis system 200, during this step, may be as shown below:

TABLE 6

Prime AC Finish Status
Prime AC Finish Status

| Component Name | Flow Rate (mL/min) | Occlude? | Open/ Closed? | Spin Rate (RPM) |
|---|---|---|---|---|
| Draw pump 208 | 0 | No | | |
| Return pump 212 | 0 | No | | |
| Anticoagulant pump 216 | −30 | | | |
| Plasma flow control valve 286 | | | Closed | |
| Saline flow control valve 288 | | | Closed | |
| First fluid control valve 320A | | | Open | |
| Second fluid control valve 320B | | | Open | |
| Draw fluid control valve 320C | | | Closed | |
| Filler 460 | | | | 0 |

Figure 14:
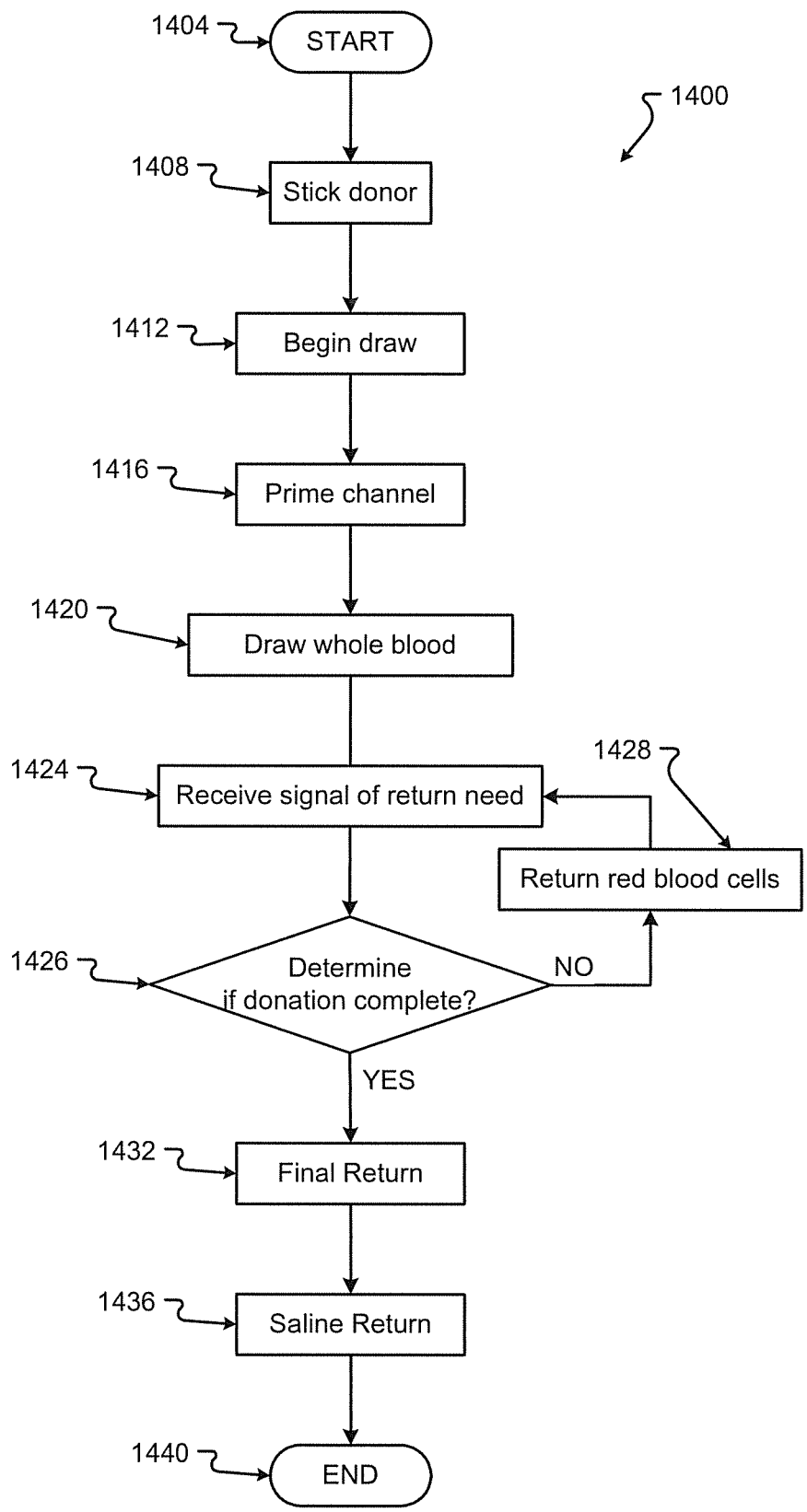
FIG. 14 is a process diagram of a method for conducting apheresis in accordance with embodiments of the present disclosure.

An embodiment of a method 1400, representing the drawing plasma phase 1212, may be as shown in FIG. 14 in accordance with embodiments of the present disclosure. A general order for the steps of the method 1400 is shown in FIG. 14. Generally, the method 1400 starts with a start operation 1404 and ends with operation 1440. The method 1400 can include more or fewer steps or can arrange the order of the steps differently than those shown in FIG. 14. The method 1400 can be, at least partially, executed as a set of computer-executable instructions executed by a computer system, processor, cassette microcontroller 1004, centrifuge microcontroller 1104, and/or other devices and encoded or stored on a computer readable medium. In other configurations, the method 1400 may be executed, at least partially, by a series of components, circuits, gates, etc. created in a hardware device, such as a SOC, ASIC, and/or a FPGA. Hereinafter, the method 1400 shall be explained with reference to the systems, devices, valves, pumps, sensors, components, circuits, modules, software, data structures, signaling processes, models, environments, apheresis systems, methods, etc. described in conjunction with FIGS. 1-13.

In step 1408, the donor 102 may be stuck with a needle. A phlebotomist, apheresis technician, or other medical professional can attach a needle, having a lumen, to the tubing fitting 504 and place the needle into a blood vessel (e.g., a vein) of the donor 102. Thus, the apheresis system 200 may be fluidly connected to the donor 102 and be ready to draw whole blood. Thus, the apheresis system 200 starts the draw plasma phase 1212 in a state with the donor 102 ready to provide whole blood as shown in FIG. 17H. The status of the various components of the apheresis system 200, during this step, may be as shown below:

TABLE 7

Stick Donor Status
Stick Donor Status

| Component Name | Flow Rate (mL/min) | Occlude? | Open/ Closed? | Spin Rate (RPM) |
|---|---|---|---|---|
| Draw pump 208 | 0 | Yes | | |
| Return pump 212 | 0 | Yes | | |
| Anticoagulant pump 216 | 0 | | | |
| Plasma flow control valve 286 | | | Closed | |
| Saline flow control valve 288 | | | Closed | |
| First fluid control valve 320A | | | Closed | |
| Second fluid control valve 320B | | | Closed | |
| Draw fluid control valve 320C | | | Closed | |
| Filler 460 | | | | 0 |

Figure 17I:
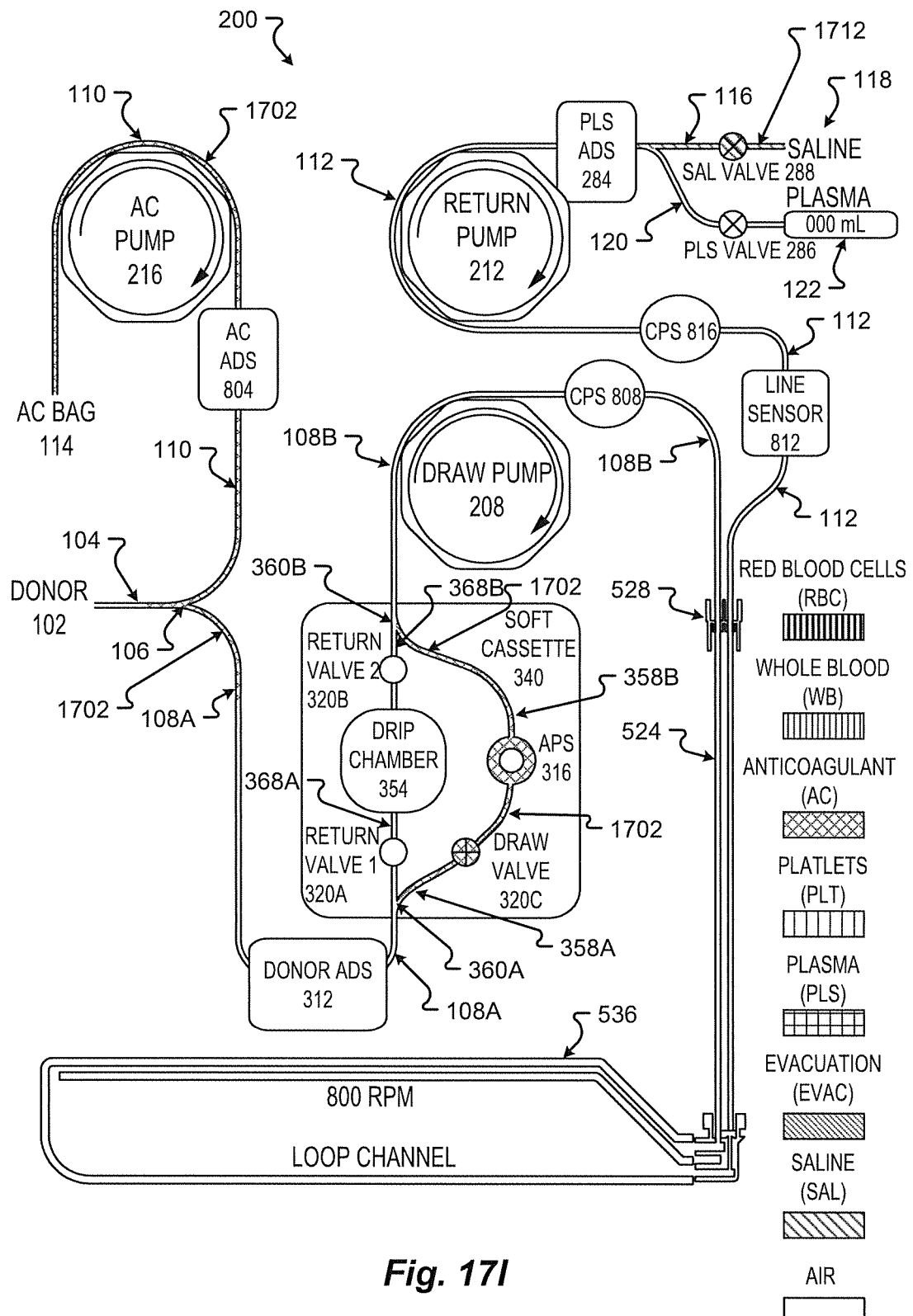
FIG. 17I is another functional diagram of the apheresis system during an apheresis procedure in accordance with embodiments of the present disclosure.

The cassette microcontroller 1004 of the apheresis system 200 can begin to draw whole blood 1706, in step 1412. The cassette microcontroller 1004 can direct the AC pump 216, the draw pump 208, and/or the return pump 212 to operate by rotating in a clockwise rotation. The AC pump 216 pushes anticoagulant 1702 towards the plasma collection bottle 122 so that the AC 1702 mixes with the whole blood 1706 being drawn from the donor 102 in the tubing connector 106 (and possibly in the donor feed tubing 104) and the other components distal to the tubing connector 106. The draw pump 208 and/or return pump 212 draws whole blood 1706 from the donor 102 (and AC) into the soft cassette 340, flexible loop 524, and/or blood component collection bladder 536. During this process 1412, the cassette microcontroller 1004 and the centrifuge microcontroller 1008 can communicate to inform the centrifuge microcontroller 1008 that the draw has begun. In response to the indication of the draw beginning, the centrifuge microcontroller 1008 can instruct the rotor and motor assembly 414 of the centrifuge assembly 400 to begin to rotate or spin. The initial rate of rotation may be slower to allow the blood component collection bladder 536 to become seated in the filler insert chamber 492 and to draw the whole blood 1706 into the blood component collection bladder 536. The state of the apheresis system 200, during this step 1412, may appear as in FIG. 17I. The status of the various components of the apheresis system 200, during this step, may be as shown below:

TABLE 8

Begin Draw Status
Begin Draw Status

| Component Name | Flow Rate (mL/min) | Occlude? | Open/ Closed? | Spin Rate (RPM) |
|---|---|---|---|---|
| Draw pump 208 | AF | Yes | | |
| Return pump 212 | (AF + 50) | Yes | | |
| Anticoagulant pump 216 | AF/15 | | | |
| Plasma flow control valve 286 | | | Open | |
| Saline flow control valve 288 | | | Closed | |
| First fluid control valve 320A | | | Open | |
| Second fluid control valve 320B | | | Open | |
| Draw fluid control valve 320C | | | Closed | |
| Filler 460 | | | | 800 |

Figure 17J:
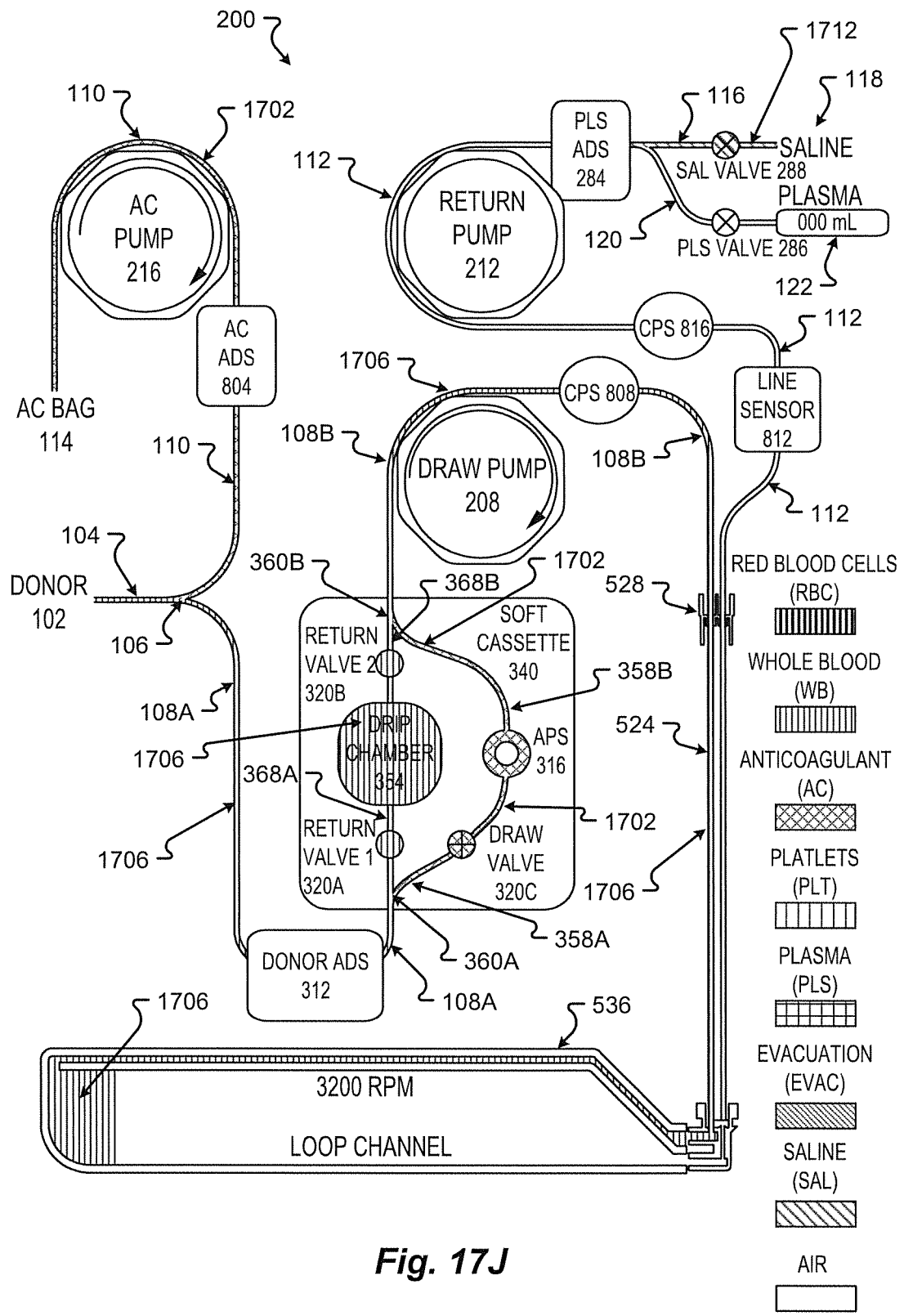
FIG. 17J is another functional diagram of the apheresis system during an apheresis procedure in accordance with embodiments of the present disclosure.

In step 1416, the areas of the blood component collection bladder 536 adjacent to the channel entrance 468, channel end 472, and/or channel path jog 476 are primed with whole blood 1706. The cassette microcontroller 1004 stops operation of the return pump 212 but continues to operate the AC pump 216 and draw pump 208. Whole blood 1706 is pushed through the first tubing section 368A, the drip chamber 354, and/or the second tubing section 368B. From the soft cassette 340, the whole blood 1706 is pushed through the flexible loop 524 and into the blood component collection bladder 536 to the bladder free end 540B. The anticoagulant pump 216 continues to operate to mix anticoagulant 1702 from the anticoagulant bag 114 with the whole blood 1706 drawn from the donor 102. The apheresis system 200 may appear as shown in FIG. 17J during step 1416. The status of the various components of the apheresis system 200, during this step, may be as shown below:

TABLE 9

Prime Channel Status
Prime Channel Status

| Component Name | Flow Rate (mL/min) | Occlude? | Open/ Closed? | Spin Rate (RPM) |
|---|---|---|---|---|
| Draw pump 208 | AF | Yes | | |
| Return pump 212 | 0 | Yes | | |
| Anticoagulant pump 216 | AF/15 | | | |
| Plasma flow control valve 286 | | | Open | |
| Saline flow control valve 288 | | | Closed | |
| First fluid control valve 320A | | | Open | |
| Second fluid control valve 320B | | | Open | |
| Draw fluid control valve 320C | | | Closed | |
| Filler 460 | | | | 3200 |

Further communication occurs between the cassette microcontroller 1004 and the centrifuge microcontroller 1008 to indicate the priming of the channel. In response to these communications, the centrifuge microcontroller 1008 directs the rotor and motor assembly 414 of the centrifuge assembly 400 to begin to rotate or spin at higher revolutions per minute (RPM).

Figure 17K:
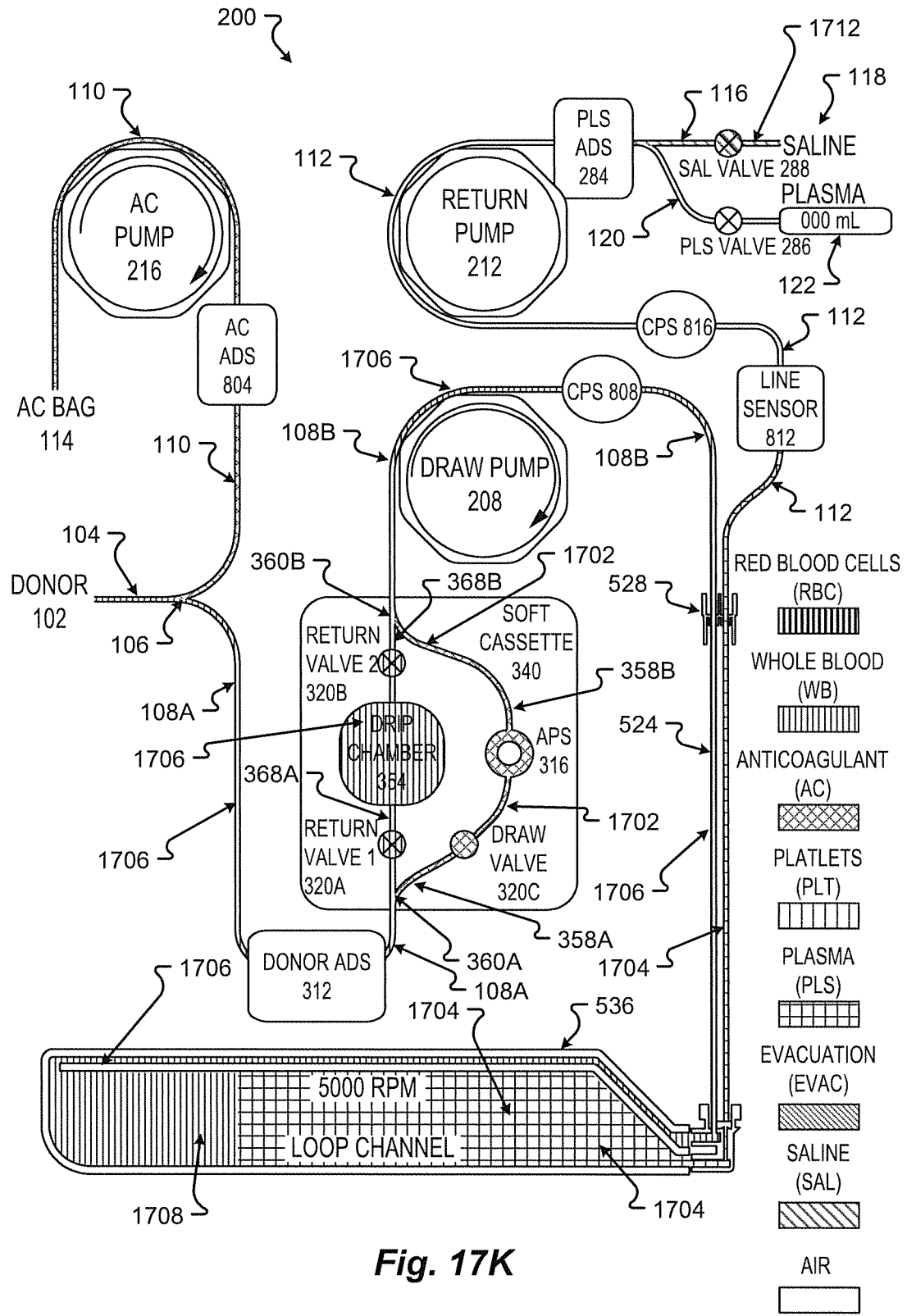
FIG. 17K is another functional diagram of the apheresis system during an apheresis procedure in accordance with embodiments of the present disclosure.
Figure 17L:
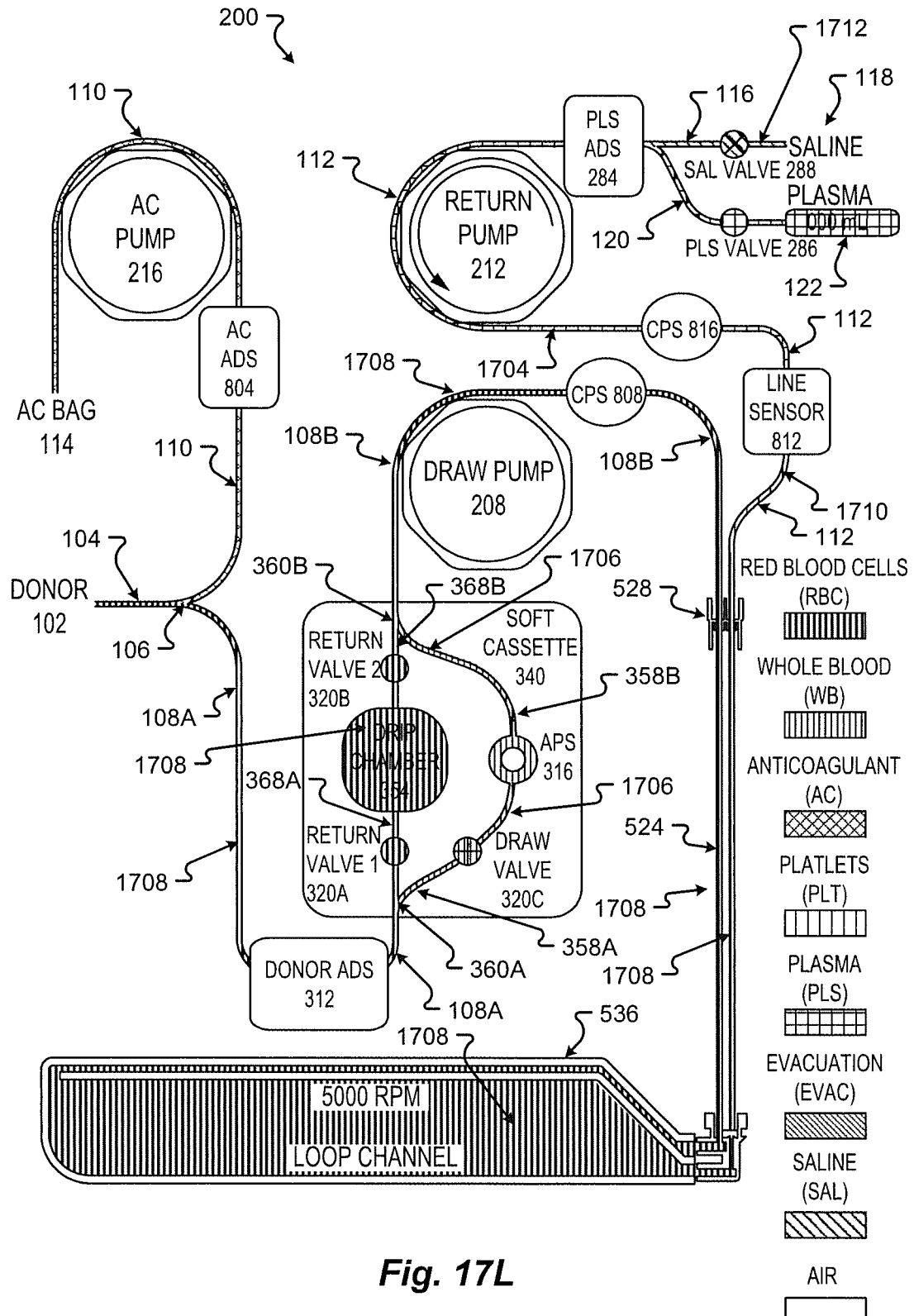
FIG. 17L is another functional diagram of the apheresis system during an apheresis procedure in accordance with embodiments of the present disclosure.

Referring now to step 1420, the cassette microcontroller 1004 begins to execute the first draw of plasma 1704 or other blood component from the whole blood 1706. The cassette microcontroller 1004 continues to operate the AC pump 216 to provide anticoagulant 1702 into the cassette inlet tubing 108A to mix with the whole blood 1706 from the donor 102. Further, the cassette microcontroller 1004 continues to operate the draw pump 208 to move whole blood 1706 into the blood component collection bladder 536 to separate the plasma 1704 from the whole blood 1706. To generate the separation of the plasma 1704, the cassette microcontroller 1004 informs the centrifuge microcontroller 1008 that the draw step has begun. In response to these communications, the centrifuge microcontroller 1008 directs the rotor and motor assembly 414 of the centrifuge assembly 400 to begin to rotate or spin at even higher revolutions per minute (RPM), e.g., substantially 5,000 RPM, to begin to separate the red blood cells 1708 from the plasma 1704, as shown in FIG. 17K. The draw pump 208 continues to push the plasma 1704 through the flexible loop 524, the system static loop connector 528, and into loop exit tubing 112. The draw process 1420 continues until, at some point, as shown in FIG. 17L, the platelets 1710, separated from the whole blood 1706, reach line sensor 812, which signals the cassette microcontroller 1004 that the total amount of plasma 1704 from the whole blood 1706 pushed into the blood component collection bladder 536 has been extracted and the cassette microcontroller 1004 moves to step 1424. The status of the various components of the apheresis system 200, during this step, may be as shown below:

TABLE 10

Draw Status
Draw Status

| Component Name | Flow Rate (mL/min) | Occlude? | Open/ Closed? | Spin Rate (RPM) |
|---|---|---|---|---|
| Draw pump 208 | AF | Yes | | |
| Return pump 212 | 0 | No | | |
| Anticoagulant pump 216 | AF/15 | | | |
| Plasma flow control valve 286 | | | Open | |
| Saline flow control valve 288 | | | Closed | |
| First fluid control valve 320A | | | Closed | |
| Second fluid control valve 320B | | | Closed | |
| Draw fluid control valve 320C | | | Open | |
| Filler 460 | | | | 5000 |

When platelets 1710, red blood cells, high hematocrit blood, and/or other blood component reach the line sensor 812, determined by the sensor 812 observing a change in color or other characteristic of the fluid, the cassette microcontroller 1004 then determines whether the donation is complete, in step 1426. A complete donation means the entire amount of plasma 1704 required or desired has been drawn and put into the plasma collection bottle 122. In embodiments, the cassette microcontroller 1004 can determine, whether by weight or volume, if a complete donation (e.g., 880 mL) has been extracted. This situation may be as shown in FIG. 17L, where the plasma 1704 has been extracted and is still present in loop exit tubing 112 and provided to the plasma collection bottle 122 through plasma tubing 120. If it is an incomplete donation, meaning the plasma collection bottle 122 has not reached its desired weight or volume limit, the process 1400 may proceed NO to return step 1428. If it is a complete donation, the method 1400 may proceed YES to the final return step 1432.

Figure 17M:
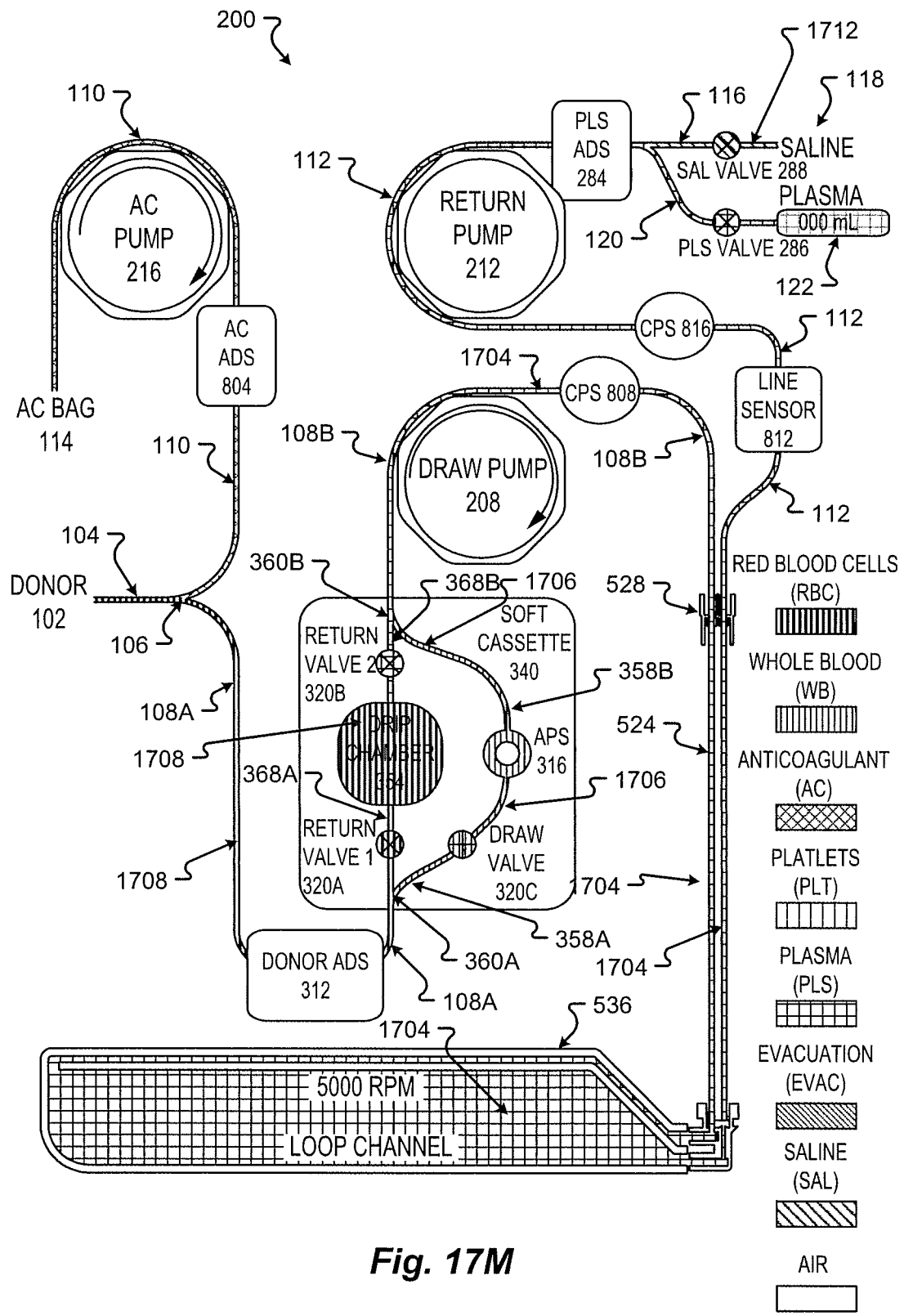
FIG. 17M is another functional diagram of the apheresis system during an apheresis procedure in accordance with embodiments of the present disclosure.

In the return step 1428, as depicted in FIG. 17L, the cassette microcontroller 1004 instructs the draw pump 208 to stop and reverses the direction of the return pump 212 to operate in a counterclockwise motion to push the plasma 1704 from plasma collection bottle 122 through the plasma tubing 120, into the loop exit tubing 112, and toward the soft cassette 340. The cassette microcontroller 1004 further directs the draw fluid control valve 320C to close and to open both the first fluid control valve 320A and the second fluid control valve 320B. These configuration changes cause the plasma 1704 to push the red blood cells 1708 and the platelets 1710 out of the loop exit tubing 112, the flexible loop 524, the blood component collection bladder 536, through the drip chamber 354, and to the donor 102. Importantly, as can be seen in FIG. 17L, the filler 460 continues to rotate at the extraction speed, e.g. 5,000 RPM, during this return step 1428. The system 200 continues to push red blood cells 1708 back into the donor 102 until the color/pressure sensor 808 determines that plasma 1704 has passed through sensor 808 and may have reached the drip chamber 354, as shown in FIG. 17M. At that point, valves 320B and 320A are closed again and the whole blood 1706 can flow again through the first bypass branch 358A, the second bypass branch 358B, and/or the fluid sensor 316. The status of the various components of the apheresis system 200, during this step 1428, may be as shown below:

TABLE 11

Return Status
Return Status

| Component Name | Flow Rate (mL/min) | Occlude? | Open/ Closed? | Spin Rate (RPM) |
|---|---|---|---|---|
| Draw pump 208 | 0 | No | | |
| Return pump 212 | AF | Yes | | |
| Anticoagulant pump 216 | 0 | | | |
| Plasma flow control valve 286 | | | Open | |
| Saline flow control valve 288 | | | Closed | |
| First fluid control valve 320A | | | Open | |
| Second fluid control valve 320B | | | Open | |
| Draw fluid control valve 320C | | | Closed | |
| Filler 460 | | | | 5000 |

The return step 1428 then moves to a second draw step 1420. The new draw proceeds in a similar fashion to step 1420 described above. However, there is a section of high hematocrit blood that remains in the drip chamber 354. By moving the new flow of whole blood 1706 through the first bypass branch 358A, second bypass branch 358B, and/or the fluid sensor 316, less high hematocrit blood is returned to blood component collection bladder 536, which red blood cells cannot have more plasma 1704 extracted therefrom. Thus, the bypass provided by the soft cassette 340 makes the removal of plasma 1704 from whole blood 1706 in the second draw step 1420 and subsequent draw steps more efficient.

Figure 17N:
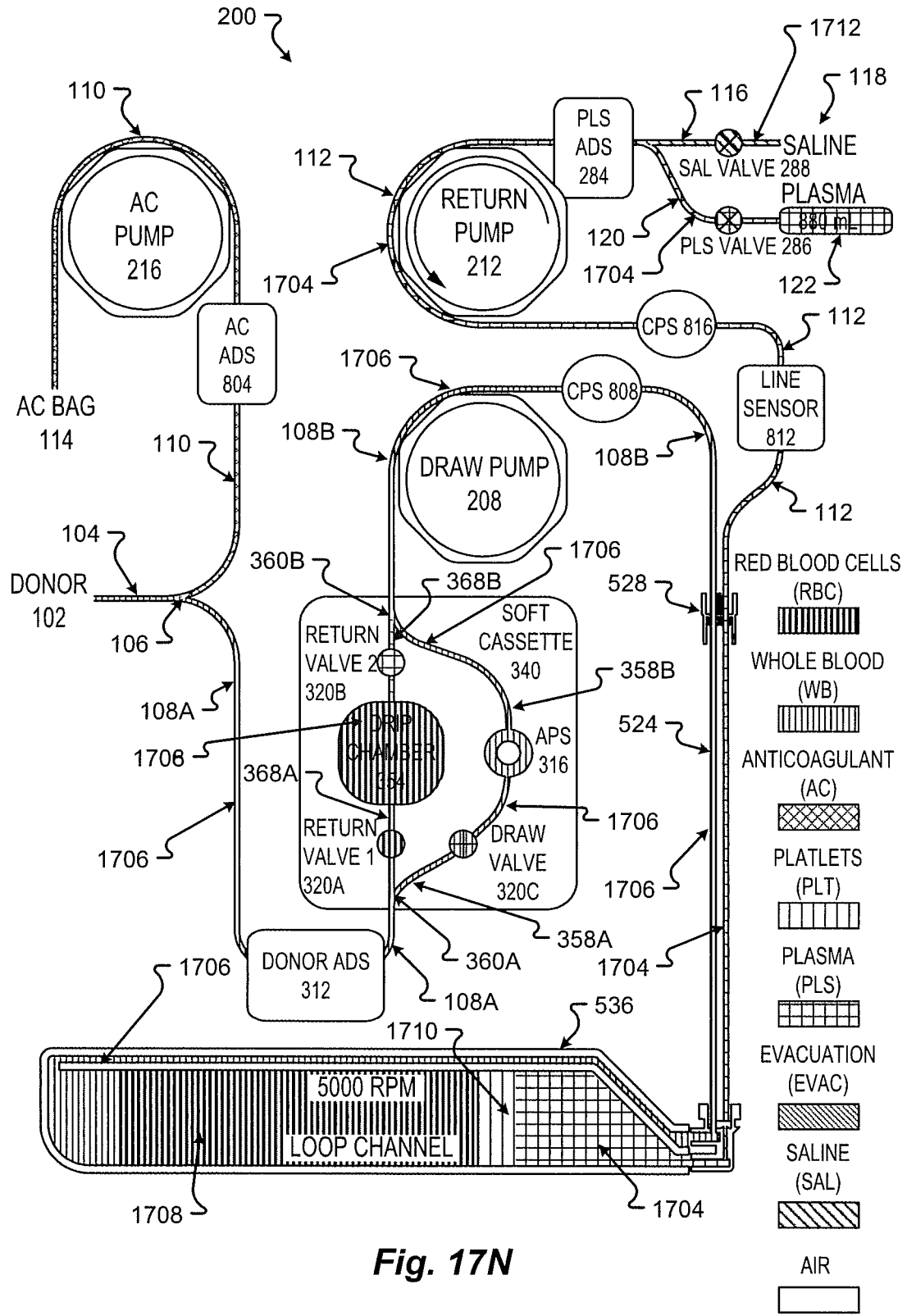
FIG. 17N is another functional diagram of the apheresis system during an apheresis procedure in accordance with embodiments of the present disclosure.

The return step 1428 and the continued draw step 1420 will repeat for some number of cycles. The final draw step 1420 may be as shown in FIG. 17N. The plasma 1704, within the plasma collection bottle 122, has reached a desired and/or maximum amount, for example 880 mL, as is shown in FIG. 17N. At this point, a final return is required, in step 1432. The status of the various components of the apheresis system 200, during this return step, may be as shown below:

TABLE 12

Final Return Status
Final Return Status

| Component Name | Flow Rate (mL/min) | Occlude? | Open/ Closed? | Spin Rate (RPM) |
|---|---|---|---|---|
| Draw pump 208 | 0 | No | | |
| Return pump 212 | AF | Yes | | |
| Anticoagulant pump 216 | 0 | | | |
| Plasma flow control valve 286 | | | Closed | |
| Saline flow control valve 288 | | | Open | |
| First fluid control valve 320A | | | Open | |
| Second fluid control valve 320B | | | Open | |
| Draw fluid control valve 320C | | | Closed | |
| Filler 460 | | | | 5000 |

In step 1432, the total amount of plasma 1704 extracted from the donor 102 is now in the plasma collection bottle 122, and the apheresis system 200 can now push through remaining plasma 1704, red blood cells 1708, and any other blood component into the donor 102. The cassette microcontroller 1004 can instruct the plasma flow control valve 286 to close to maintain the plasma donation in the plasma collection bottle 122. The return pump 212 can continue to operate in the counterclockwise rotation to push the red blood cells 1708 and any plasma 1704 or other blood components back to the donor 102.

Figure 17O:
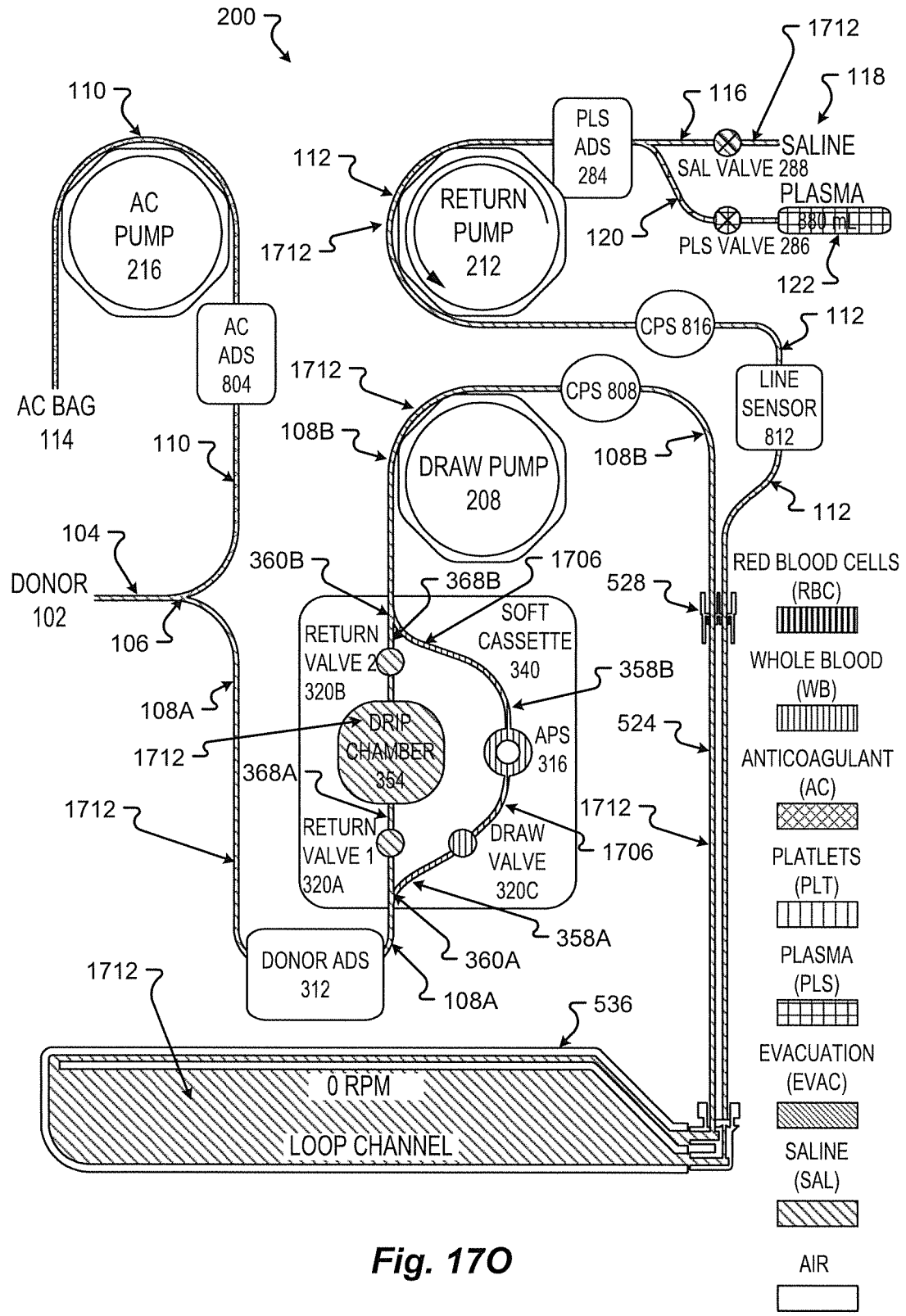
FIG. 17O is another functional diagram of the apheresis system during an apheresis procedure in accordance with embodiments of the present disclosure.

After or as part of the final return 1432, the saline 1712 may also be returned to the donor 102, as shown in FIG. 17O, in step 1436. In this step 1436, the cassette microcontroller 1004 opens the saline flow control valve 288 and leaves the first fluid control valve 320A and the second fluid control valve 320A open. The return pump 212 continues to operate in the counterclockwise direction. The centrifuge microcontroller 1008 stops the filler 460 from rotating. The saline 1712 from the saline bag 118 is pushed through the blood component collection bladder 536, the drip chamber 354, and the various tubing back to the donor 102. The various blood components left in the blood component collection set 500 are pushed back into the donor 102 along with some amount of saline 1712. The saline 1712 helps replenish fluids for the donor 102 and is required in some jurisdictions. This saline 1712 return continues until a predetermined amount of saline 1712 is provided to the user as determined by the weight or volume of saline 1712 that has left the saline bag 118. At this point, as shown in FIG. 17O, the plasma donation is complete. The status of the various components of the apheresis system 200, during this step, may be as shown below:

TABLE 13

Saline Return Status
Saline Return Status

| Component Name | Flow Rate (mL/min) | Occlude? | Open/ Closed? | Spin Rate (RPM) |
|---|---|---|---|---|
| Draw pump 208 | 0 | No | | |
| Return pump 212 | AF (300) | Yes | | |
| Anticoagulant pump 216 | 0 | | | |
| Plasma flow control valve 286 | | | Closed | |
| Saline flow control valve 288 | | | Open | |
| First fluid control valve 320A | | | Open | |
| Second fluid control valve 320B | | | Open | |
| Draw fluid control valve 320C | | | Open | |
| Filler 460 | | | | 0 |

Figure 15:
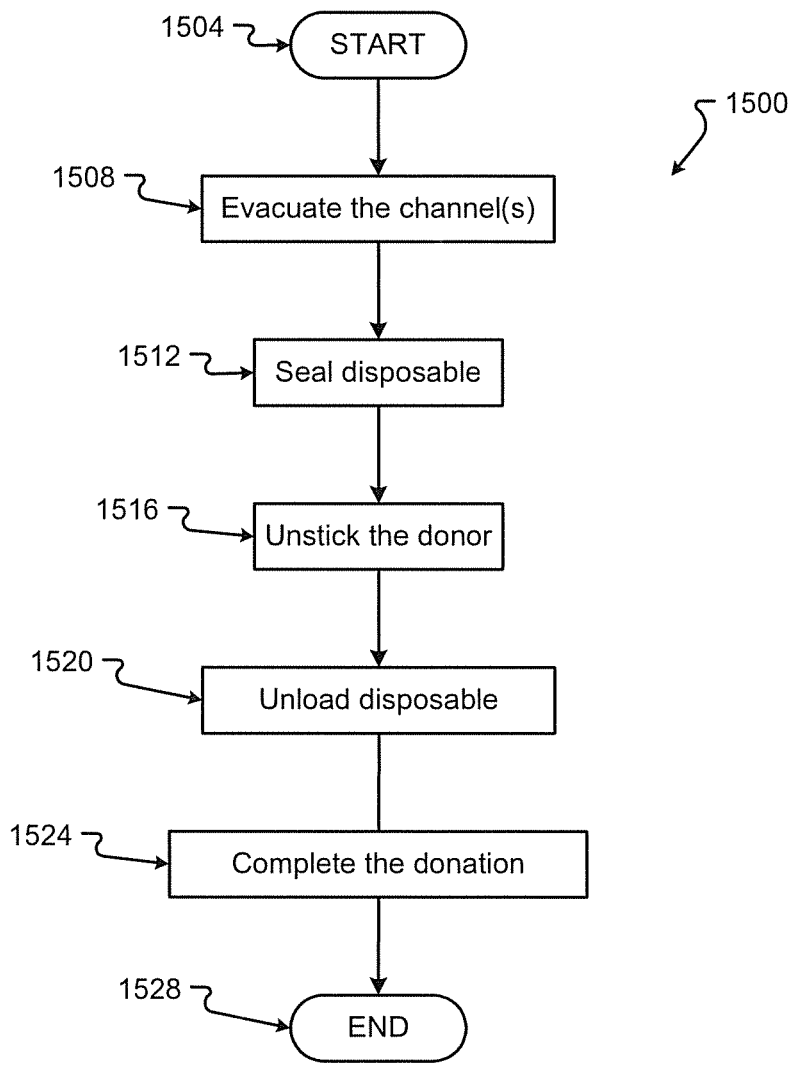
FIG. 15 is a process diagram of a method for conducting apheresis in accordance with embodiments of the present disclosure.

An embodiment of a method for unloading the plasma and blood component collection set 500 from the apheresis system 200, as described in unloading phase 1216, may be as shown in FIG. 15, in accordance with embodiments of the present disclosure. A general order for the steps of the method 1500 is shown in FIG. 15. Generally, the method 1500 starts with a start operation 1504 and ends with operation 1528. The method 1500 can include more or fewer steps or can arrange the order of the steps differently than those shown in FIG. 15. The method 1500 can be, at least partially, executed as a set of computer-executable instructions executed by a computer system, processor, cassette microcontroller 1004, centrifuge microcontroller 1104, and/or other devices and encoded or stored on a computer readable medium. In other configurations, the method 1500 may be executed, at least partially, by a series of components, circuits, gates, etc. created in a hardware device, such as a SOC, ASIC, and/or a FPGA. Hereinafter, the method 1500 shall be explained with reference to the systems, devices, valves, pumps, sensors, components, circuits, modules, software, data structures, signaling processes, models, environments, apheresis systems, methods, etc. described in conjunction with FIGS. 1-14.

Figure 17P:
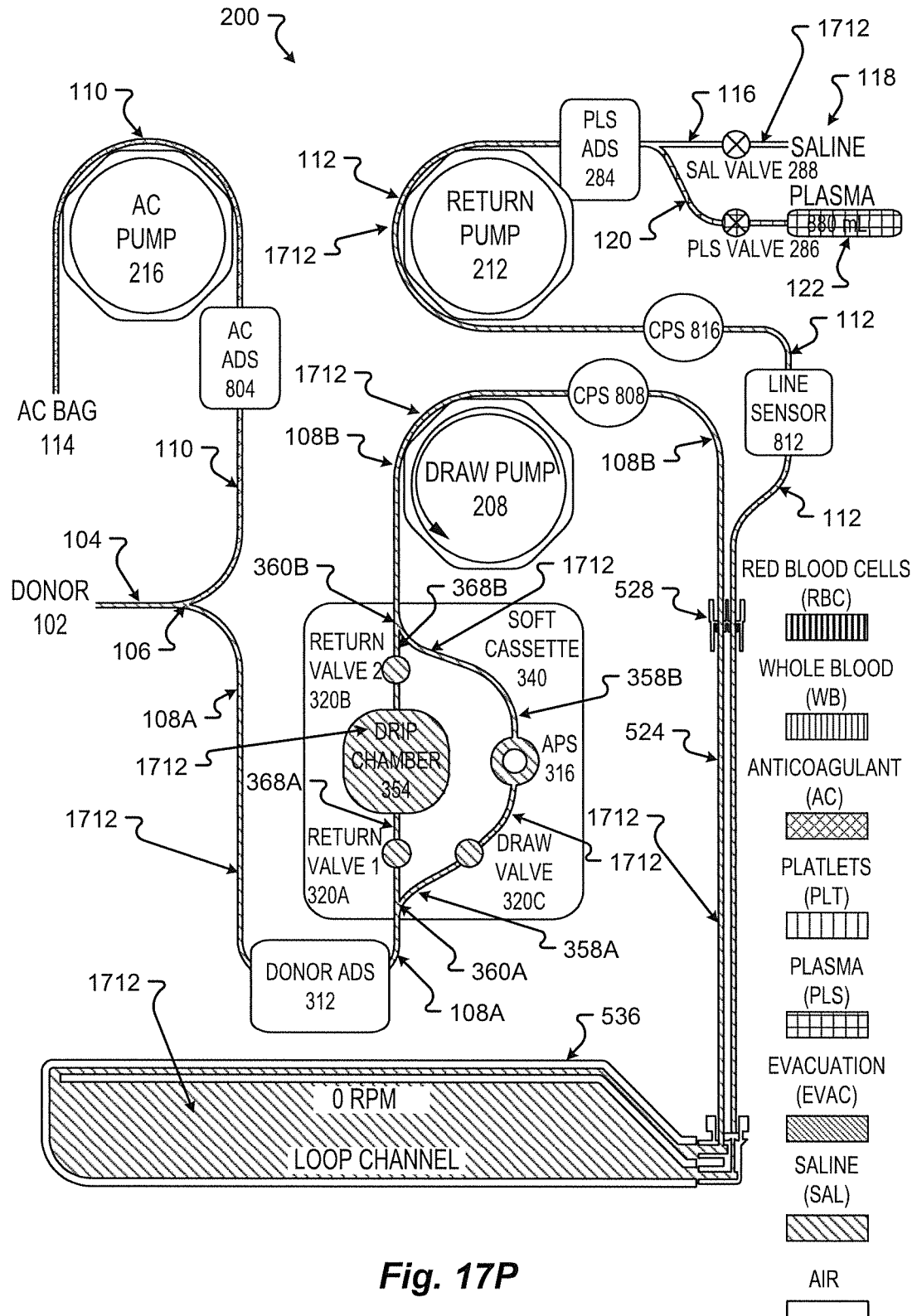
FIG. 17P is another functional diagram of the apheresis system during an apheresis procedure in accordance with embodiments of the present disclosure.
Figure 17Q:
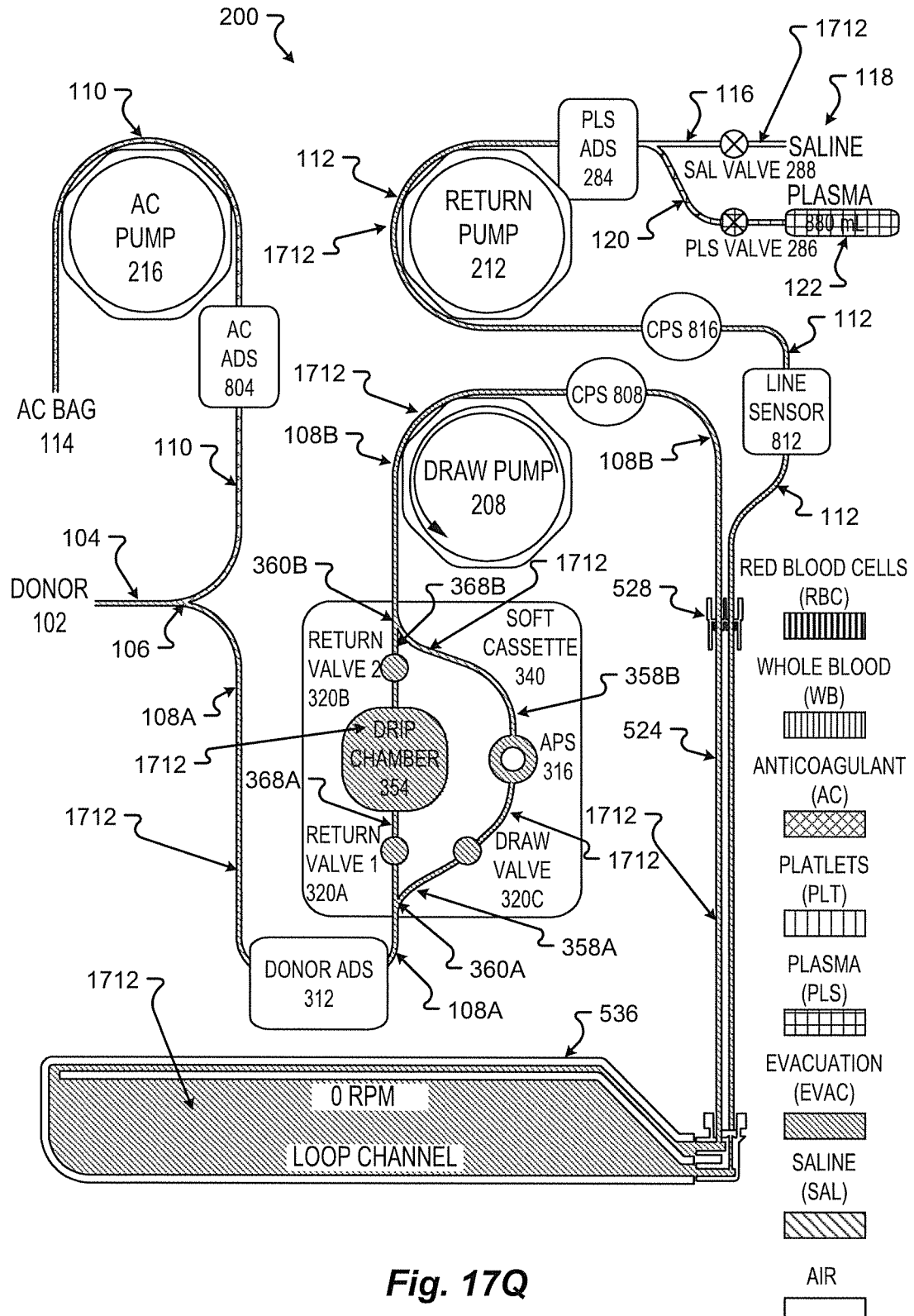
FIG. 17Q is another functional diagram of the apheresis system during an apheresis procedure in accordance with embodiments of the present disclosure.

The channels are evacuated, in step 1508. In embodiments, the cassette microcontroller 1004 operates the draw pump 208 in a counterclockwise direction to continue to drive saline 1712 substantially completely out of the blood component collection bladder 536 and the rest of the blood component collection set 500, as shown in FIG. 17P. At some point, substantially the total amount of blood components and/or saline 1712 gets pushed back into the donor 102, in which case all pumps 216, 208, and 212 cease operation. The fluid control valve 320A, first fluid control valve 320A, saline flow control valve 288, and any other valve can then be shut by the cassette microcontroller 1004. At this point, only a minute amount of saline 1712 or no saline at all should remain within the blood component collection set 500. The state of the apheresis system 200 may be as shown in FIG. 17Q. The status of the various components of the apheresis system 200, during this step, may be as shown below:

TABLE 14

Channel Evacuation Status
Channel Evacuation Status

| Component Name | Flow Rate (mL/min) | Occlude? | Open/ Closed? | Spin Rate (RPM) |
| --- | --- | --- | --- | --- |
| Draw pump 208 | −AF | Yes | | |
| Return pump 212 | 0 | Yes | | |
| Anticoagulant pump 216 | 0 | | | |
| Plasma flow control valve 286 | | | Closed | |
| Saline flow control valve 288 | | | Closed | |
| First fluid control valve 320A | | | Open | |
| Second fluid control valve 320B | | | Open | |
| Draw fluid control valve 320C | | | Open | |
| Filler 460 | | | | 0 |

Figure 17R:
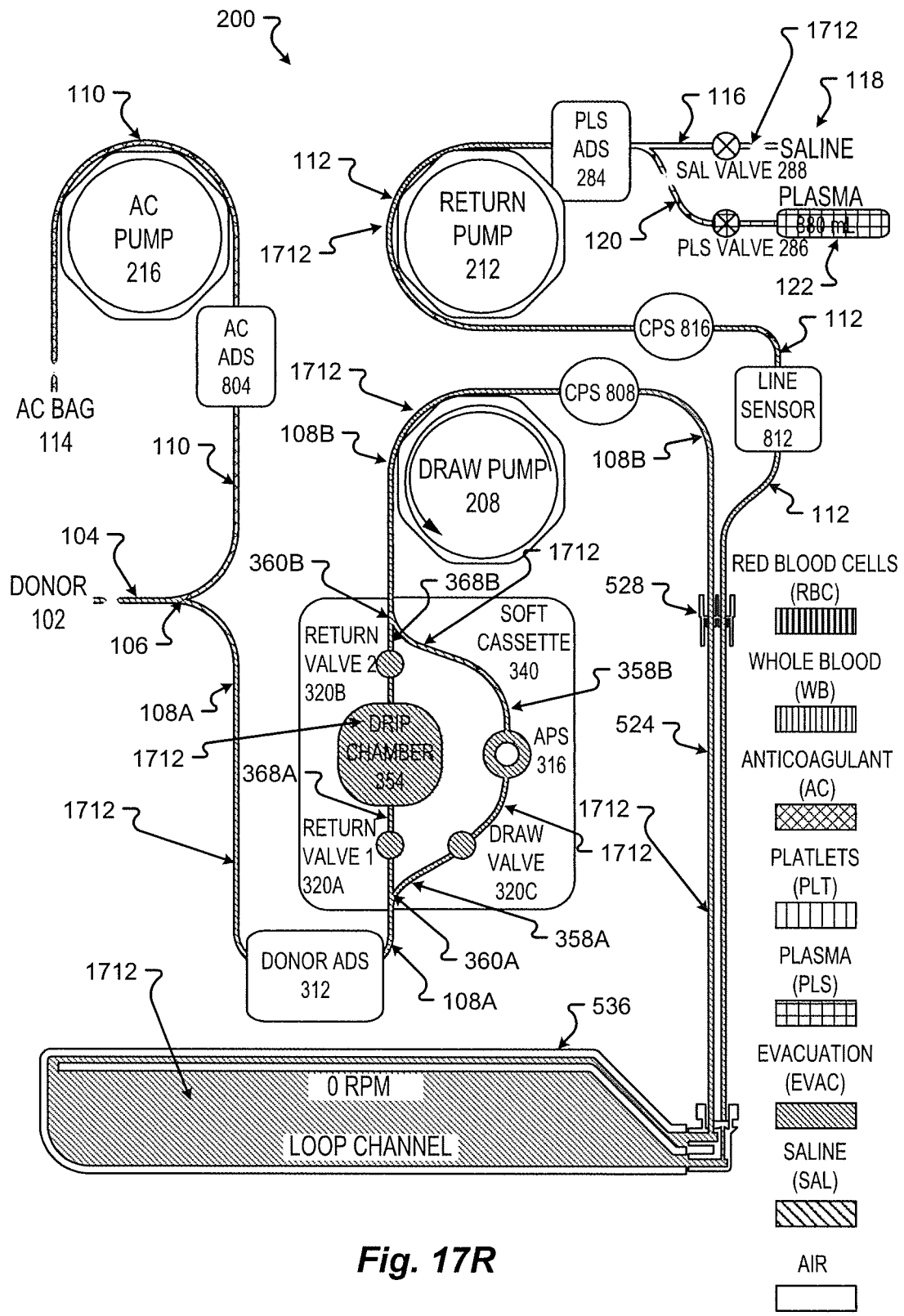
FIG. 17R is another functional diagram of the apheresis system during an apheresis procedure in accordance with embodiments of the present disclosure.

At this point, the blood component collection set 500 can be sealed, in step 1512, as shown in FIG. 17R. The sealing of blood component collection set 500 can include clamping the donor feed tubing 104 that leads to the donor 102 and fusion sealing the tubing at various places. The sealing can be a fusion of the tubes, as the tubes may be thermoplastic, as shown in FIG. 17R. For example, the anticoagulant tubing 110, the saline tubing 116, the plasma tubing 120 (above the plasma flow control valve 286), and the donor feed tubing 104 are all heat fused to separate the AC bag 114, the plasma collection bottle 122, the saline bag 118, and the donor 102 from the rest of the blood component collection set 500. The status of the various components of the apheresis system 200, during this step, may be as shown below:

TABLE 15

Seal Kit Status
Seal Kit Status

| Component Name | Flow Rate (mL/min) | Occlude? | Open/ Closed? | Spin Rate (RPM) |
| --- | --- | --- | --- | --- |
| Draw pump 208 | 0 | Yes | | |
| Return pump 212 | 0 | Yes | | |
| Anticoagulant pump 216 | 0 | | | |
| Plasma flow control valve 286 | | | Closed | |
| Saline flow control valve 288 | | | Closed | |
| First fluid control valve 320A | | | Closed | |
| Second fluid control valve 320B | | | Closed | |
| Draw fluid control valve 320C | | | Closed | |
| Filler 460 | | | | 0 |

At this point, the needle may be taken out of the donor 102, in step 1516, as shown in 17R. The status of the various components of the apheresis system 200, during this step, may be as shown below:

TABLE 16

Unstick Donor Status
Unstick Donor Status

| Component Name | Flow Rate (mL/min) | Occlude? | Open/ Closed? | Spin Rate (RPM) |
| --- | --- | --- | --- | --- |
| Draw pump 208 | 0 | Yes | | |
| Return pump 212 | 0 | Yes | | |
| Anticoagulant pump 216 | 0 | | | |
| Plasma flow control valve 286 | | | Closed | |
| Saline flow control valve 288 | | | Closed | |
| First fluid control valve 320A | | | Closed | |
| Second fluid control valve 320B | | | Closed | |
| Draw fluid control valve 320C | | | Closed | |
| Filler 460 | | | | 0 |

Figure 16:
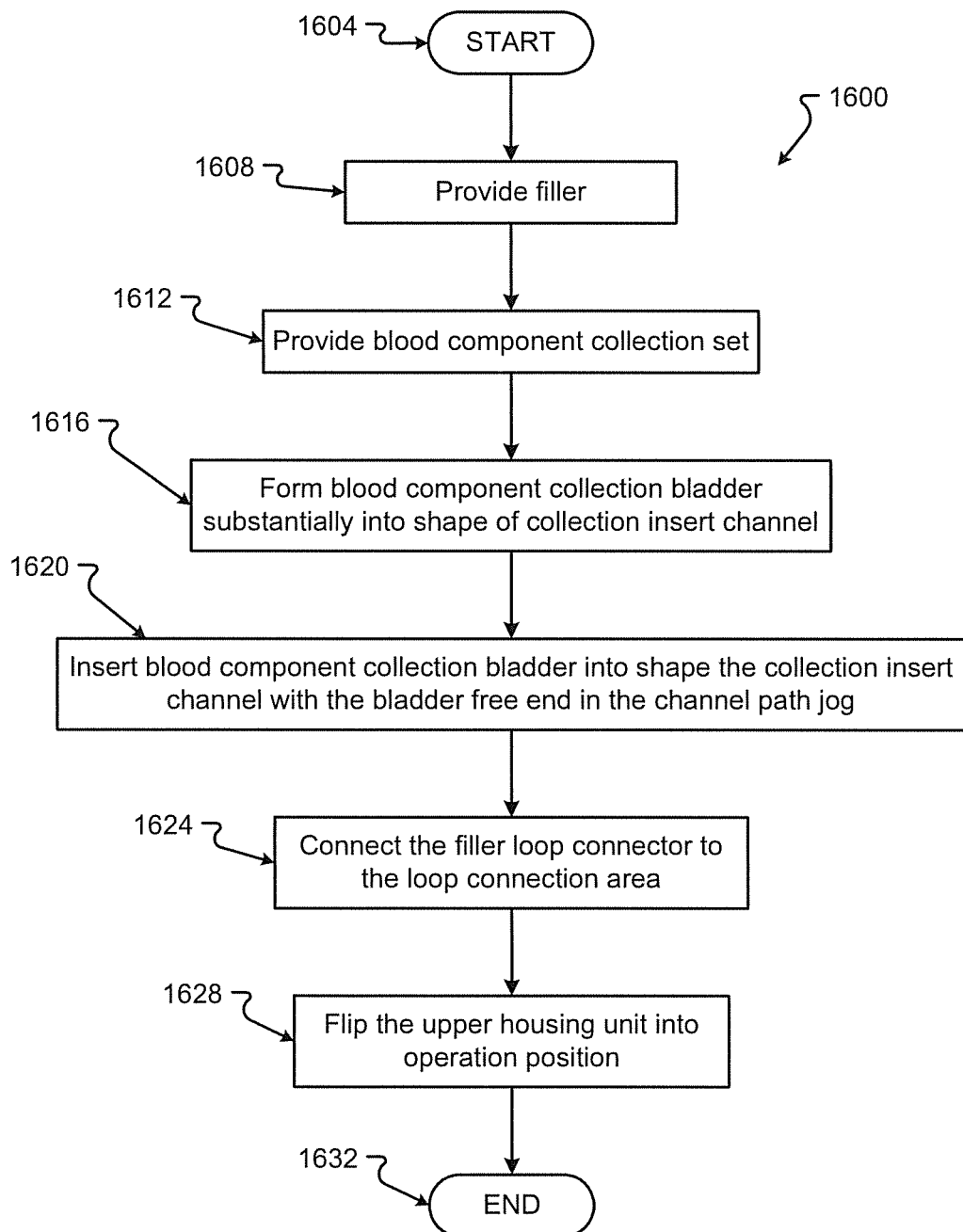
FIG. 16 is a process diagram of a method for inserting a disposable into the filler of the apheresis system in accordance with embodiments of the present disclosure.

The blood component collection set 500 may be unloaded from the apheresis system 200, in step 1520, which entails reversing at least some of the procedures described in conjunction with FIGS. 13 and 16. The status of the various components of the apheresis system 200, during this step, may be as shown below:

TABLE 17

Unload Status
Unload Status

| Component Name | Flow Rate (mL/min) | Occlude? | Open/ Closed? | Spin Rate (RPM) |
| --- | --- | --- | --- | --- |
| Draw pump 208 | 0 | No | | |
| Return pump 212 | 0 | No | | |
| Anticoagulant pump 216 | 0 | | | |
| Plasma flow control valve 286 | | | Open | |
| Saline flow control valve 288 | | | Open | |
| First fluid control valve 320A | | | Open | |
| Second fluid control valve 320B | | | Open | |
| Draw fluid control valve 320C | | | Open | |
| Filler 460 | | | | 0 |

Figure 17S:
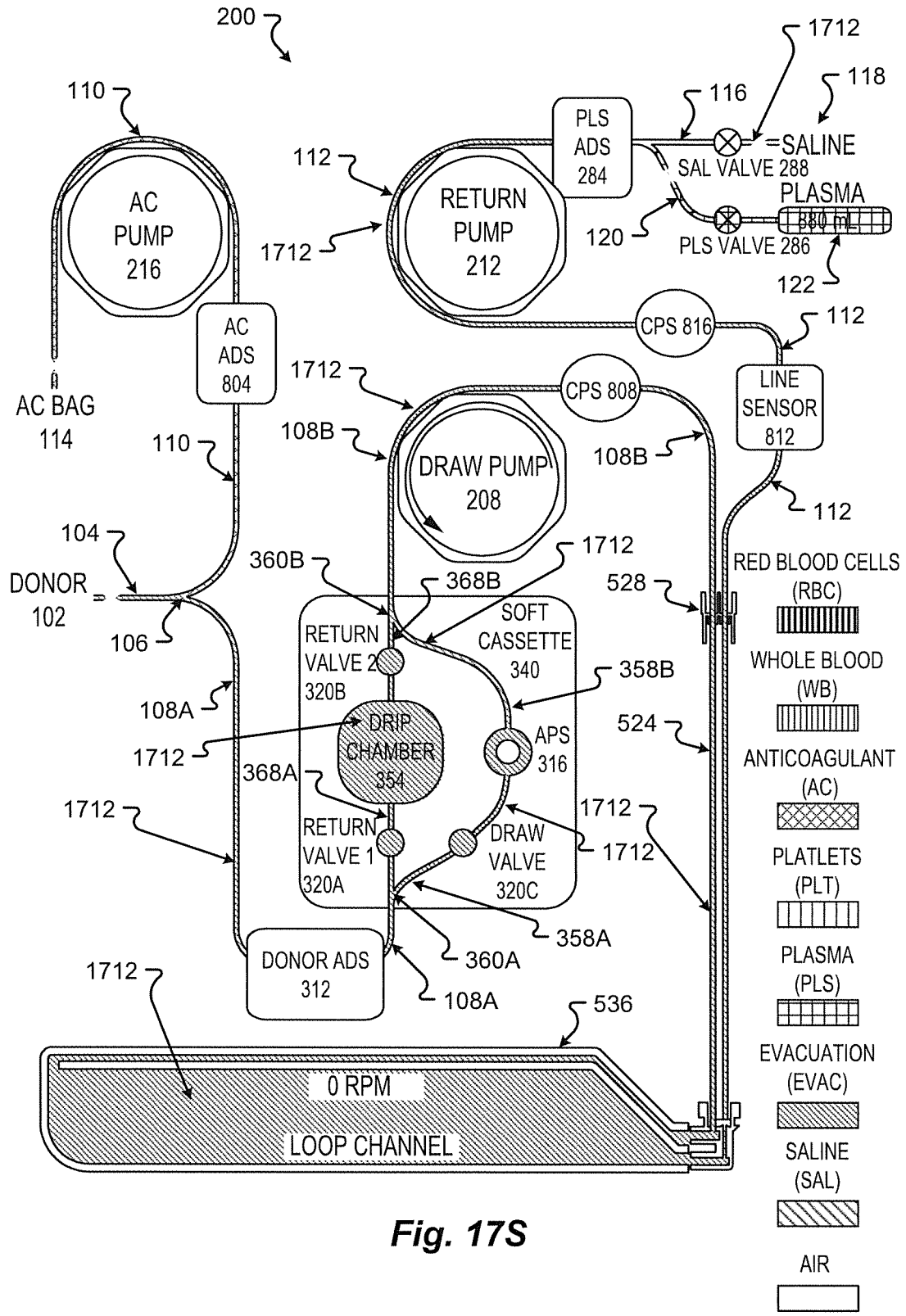
FIG. 17S is another functional diagram of the apheresis system during an apheresis procedure in accordance with embodiments of the present disclosure.
Figure 17T:
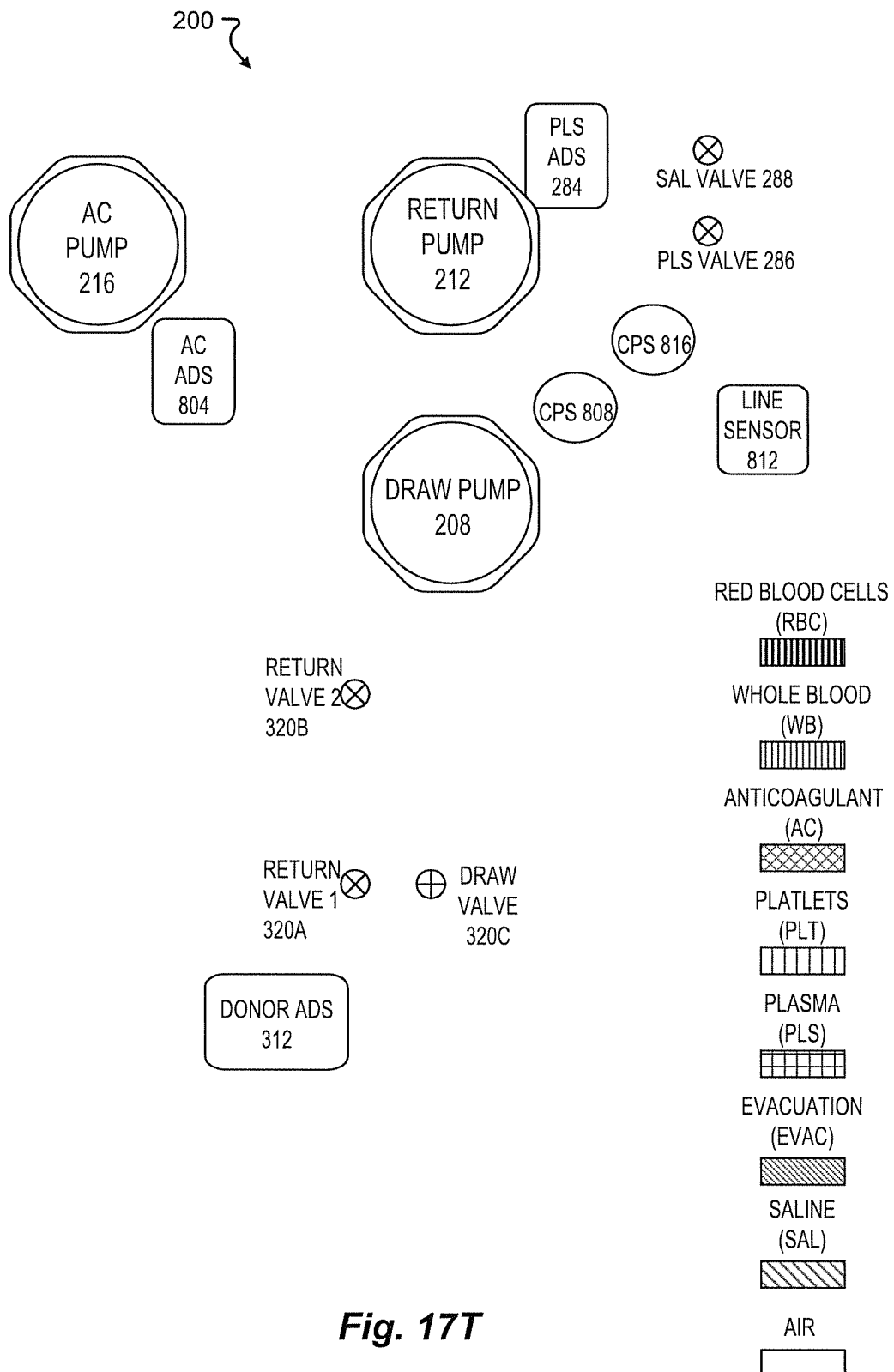
FIG. 17T is another functional diagram of the apheresis system during an apheresis procedure in accordance with embodiments of the present disclosure.

Once unloaded, the used blood component collection set 500 can be disposed of as medical waste. The plasma collection bottle 122 may be sealed on plasma tubing 120, as shown in FIG. 17S. The sealed areas may then prevent any liquid from seeping from the plasma collection bottle 122, the saline bag 118, or the anticoagulant bag 114. The plasma collection bottle 122 may be then be removed and used in whatever procedure the plasma is required. The rest of the items may be discarded as medical waste and the procedure is completed, in step 1524, as shown in FIG. 17T. The status of the various components of the apheresis system 200, at the end of the procedure, may be as shown below:

TABLE 18

Complete Procedure Status
Complete Procedure Status

| Component Name | Flow Rate (mL/min) | Occlude? | Open/ Closed? | Spin Rate (RPM) |
|---|---|---|---|---|
| Draw pump 208 | 0 | No | | |
| Return pump 212 | 0 | No | | |
| Anticoagulant pump 216 | 0 | | | |
| Plasma flow control valve 286 | | | Open | |
| Saline flow control valve 288 | | | Open | |
| First fluid control valve 320A | | | Open | |
| Second fluid control valve 320B | | | Open | |
| Draw fluid control valve 320C | | | Open | |
| Filler 460 | | | | 0 |

An embodiment of a method 1600 for inserting a disposable into the filler of the apheresis system 200 may be as shown in FIG. 16, in accordance with embodiments of the present disclosure. A general order for the steps of the method 1600 is shown in FIG. 16. Generally, the method 1600 starts with a start operation 1604 and ends with operation 1632. The method 1600 can include more or fewer steps or can arrange the order of the steps differently than those shown in FIG. 16. The method 1600 can be, at least partially, executed as a set of computer-executable instructions executed by a computer system, processor, cassette microcontroller 1004, centrifuge microcontroller 1104, and/or other devices and encoded or stored on a computer readable medium. In other configurations, the method 1600 may be executed, at least partially, by a series of components, circuits, gates, etc. created in a hardware device, such as a SOC, ASIC, and/or a FPGA. Hereinafter, the method 1600 shall be explained with reference to the systems, devices, valves, pumps, sensors, components, circuits, modules, software, data structures, signaling processes, models, environments, apheresis systems, methods, etc. described in conjunction with FIGS. 1-15.

A filler 460 of an apheresis system 200 may be provided, in step 1608. The filler 460 can be a component of the apheresis system 200 and configured to receive at least a portion of the blood component collection set 500. In embodiments, the filler 460 is mounted on a split-housing pivot axis 406 that pivots to expose an internal portion of the upper housing 404B, including the filler 460. A user may pivot the upper housing 404B to expose the collection insert channel 466 or, in some embodiments, the filler 460 may be automatically pivoted by a motor or other mechanical device. This pivoting and/or loading may be as described in conjunction with FIGS. 4D-4F and/or FIGS. 6A-6C above.

A blood component collection set 500, including a blood component collection bladder 536, may be provided, in step 1612. The blood component collection set 500 may be prepackaged and extracted from the packaging. A user can expose the blood component collection bladder 536 for insertion into the collection insert channel 466, including ensuring that the bladder free end 540B is positioned at the channel path jog 476 of the collection insert channel 466 and the filler loop connector 532 is positioned at the loop connection area 454. With the blood component collection bladder 536 positioned properly, the user can form the blood component collection bladder 536 substantially into the shape of collection insert channel 466 and the channel path jog 476, in step 1616, as shown in FIGS. 5F-5H. Thus, the user can form the blood component collection bladder 536 generally into a circular shape or any other shape the generally matches the shape of the collection insert channel 466.

The user may then insert the formed blood component collection bladder 536 into the collection insert channel 466 of the filler 460, as shown in FIGS. 5G and 5H, with the bladder free end 540B of the blood component collection bladder 536 inset into the channel path jog 476 of the collection insert channel 466, in step 1620. The user can insert the blood component collection bladder 536 into the collection insert channel 466 generally at a central position within filler insert chamber 492. Centrifugal forces will generally align the blood component collection bladder 536 automatically into the correct position within the filler insert chamber 492. However, if not positioned where centrifugal forces may act on the blood component collection bladder 536, the blood component collection bladder 536 can be ejected from the collection insert channel 466. Once positioned, the blood component collection bladder 536 can be fixed in place.

In step 1624, the user can connect the filler loop connector 532 of the blood component collection bladder 536 to the loop connection area 454 of the collection insert channel 466. A mechanical connection may be made by the user snapping the filler loop connector 532 into the loop connection area 454. The dimensions and physical features of the filler insert chamber 492 can then hold blood component collection bladder 536, with the filler loop connector 532 stable in the loop connection area 454, in a stable position allowing the blood component collection bladder 536 to migrate into the center of the filler insert chamber 492 during operation of the centrifuge 400. The portion of the flexible loop 524, remaining outside or outboard of the filler 460 can be mounted to the loop capture arm 416. This mounting of the flexible loop 524 allows for the 1ω/2ω action of the centrifuge 400.

After the flexible loop 524 is mounted, the upper housing 404B may be flipped into position, in step 1628. Thus, the filler 460 may be pivoted by the hinge axis 406 (e.g., hinge, etc.) into the interior of the system housing 204. The centrifuge housing 404 may then be rotated with blood component collection loop 520 passing through a loop access clearance 436 in the centrifuge split-housing 404. When the blood component collection loop 520 is loaded in the loop loading position 520A, a portion of the blood component collection loop 520 may be partially contained, held, and/or supported by a loop containment bracket 426, as described in conjunction with FIGS. 4A-4C. The access panel 224 may be pivoted into the closed position allowing for the operation of the system 200.

The exemplary systems and methods of this disclosure have been described in relation to apheresis methods and systems. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Furthermore, while the exemplary aspects, embodiments, and/or configurations illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as the cassette node 904 and the centrifuge node 908, or collocated on a particular node of a distributed network, such as an analog and/or digital telecommunications network, a packet-switch network, or a circuit-switched network. It will be appreciated from the preceding description, and for reasons of computational efficiency, that the components of the system can be arranged at any location within a distributed network of components without affecting the operation of the system. For example, the various components can be located in a switch such as a PBX and media server, gateway, in one or more communications devices, at one or more users' premises, or some combination thereof. Similarly, one or more functional portions of the system could be distributed between a telecommunications device(s) and an associated computing device.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

Also, while the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and\or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A filler for holding a separation bladder in which a component is separated from a composite fluid, the filler comprising:
   a channel for holding a separation bladder during separation of the component from the composite fluid, the channel comprising:
   a first wall; and
   a second wall opposite the first wall; and
   wherein a first end of the channel is adjacent a central portion of the filler, the channel spirals toward an outside perimeter of the filler to a second end, and the channel jogs outwardly towards the outside perimeter of the filler near the second end of the channel.

2. The filler of claim 1, wherein a top portion of the channel is narrower than a middle portion of the channel.

3. The filler of claim 2, wherein the top portion of the channel provides reinforcement to the separation bladder during separation.

4. The filler of claim 1, wherein at least a portion of the second wall has a concave surface.

5. The filler of claim 1, wherein the second end of the channel is located so that it experiences a higher gravitational force during separation than the first end.

* * * * *